United States Patent
Binder et al.

(10) Patent No.: US 9,695,217 B2
(45) Date of Patent: Jul. 4, 2017

(54) PEPTIDE DOMAINS THAT BIND SMALL MOLECULES

(71) Applicants: Iowa State University Research Foundation, Inc., Ames, IA (US); Archer-Daniels-Midland Company, Decatur, IL (US)

(72) Inventors: Thomas P. Binder, Decatur, IL (US); Aragula Gururaj Rao, Urbandale, IA (US); Yasufumi Yamamoto, Ames, IA (US); Paul D. Hanke, Urbana, IL (US)

(73) Assignees: Iowa State University Research Foundation, Inc., Ames, IA (US); Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 14/968,386

(22) Filed: Dec. 14, 2015

(65) Prior Publication Data

US 2016/0376310 A1 Dec. 29, 2016

Related U.S. Application Data

(62) Division of application No. 13/575,834, filed as application No. PCT/US2011/023030 on Jan. 28, 2011, now Pat. No. 9,447,150.

(60) Provisional application No. 61/299,449, filed on Jan. 29, 2010.

(51) Int. Cl.
C07K 7/06 (2006.01)
C40B 30/06 (2006.01)
C07K 5/08 (2006.01)

(52) U.S. Cl.
CPC . *C07K 7/06* (2013.01); *C07K 5/08* (2013.01)

(58) Field of Classification Search
None
See application file for complete search history.

(56) References Cited

U.S. PATENT DOCUMENTS

| | | | |
|---|---|---|---|
| 6,015,783 A | 1/2000 | von der Osten et al. | |
| 7,846,445 B2 | 12/2010 | Schellenberger | |
| 2002/0072587 A1 | 6/2002 | Somers | |
| 2002/0164718 A1 | 11/2002 | Tchaga et al. | |
| 2004/0034888 A1* | 2/2004 | Liu | C07K 14/415 800/289 |
| 2005/0042684 A1 | 2/2005 | Aehle et al. | |
| 2005/0058996 A1 | 3/2005 | Wolfgang et al. | |
| 2006/0135433 A1 | 6/2006 | Murray et al. | |
| 2006/0257927 A1 | 11/2006 | Mehigh et al. | |
| 2007/0281333 A1 | 12/2007 | Yeh et al. | |
| 2008/0254512 A1 | 10/2008 | Capon et al. | |
| 2009/0099031 A1 | 4/2009 | Stemmer et al. | |
| 2013/0116138 A1 | 5/2013 | Binder et al. | |
| 2013/0326723 A1 | 12/2013 | La Rosa et al. | |

FOREIGN PATENT DOCUMENTS

| | | |
|---|---|---|
| CN | 101616685 A | 12/2009 |
| CN | 102947324 A | 2/2013 |
| EP | 2402754 A2 | 1/2012 |
| GB | 2328209 A | 2/1999 |
| GB | 2429457 A | 2/2007 |
| WO | WO-92/10576 A1 | 6/1992 |
| WO | WO-02/090544 A2 | 11/2002 |
| WO | WO-03/023067 A1 | 3/2003 |
| WO | WO-2009/067191 A2 | 5/2009 |
| WO | WO-2011/094617 A2 | 8/2011 |
| WO | WO-2011/094617 A3 | 8/2011 |

OTHER PUBLICATIONS

"U.S. Appl. No. 13/575,834, Final Office Action mailed May 21, 2015", 8 pgs.
"U.S. Appl. No. 13/575,834, Final Office Action mailed Jun. 5, 2014", 7 pgs.
"U.S. Appl. No. 13/575,834, Non Final Office Action mailed Feb. 12, 2014", 7 pgs.
"U.S. Appl. No. 13/575,834, Non Final Office Action mailed Sep. 24, 2014", 8 pgs.
"U.S. Appl. No. 13/575,834, Notice of Allowability mailed Jun. 24, 2016", 4 pgs.
"U.S. Appl. No. 13/575,834, Notice of Allowability mailed Aug. 24, 2016", 2 pgs.
"U.S. Appl. No. 13/575,834, Notice of Allowability mailed Sep. 14, 2015", 4 pgs.
"U.S. Appl. No. 13/575,834, Notice of Allowance mailed Jul. 20, 2015", 7 pgs.
"U.S. Appl. No. 13/575,834, Preliminary Amendment filed Jul. 27, 2012", 3 pgs.
"U.S. Appl. No. 13/575,834, PTO Response to Rule 312 Communication mailed Jul. 14, 2016", 2 pgs.
"U.S. Appl. No. 13/575,834, PTO Response to Rule 312 Communication mailed Oct. 2, 2015", 2 pgs.
"U.S. Appl. No. 13/575,834, Response filed Jan. 26, 2015 to Non Final Office Action mailed Sep. 24, 2014", 11 pgs.
"U.S. Appl. No. 13/575,834, Response filed May 12, 2014 to Non Final Office Action mailed Feb. 12, 2014", 9 pgs.

(Continued)

*Primary Examiner* — Amber D Steele
*Assistant Examiner* — Schuyler Milton
(74) *Attorney, Agent, or Firm* — Schwegman Lundberg & Woessner, P.A.

(57) ABSTRACT

Described herein are small peptide domains and consensus sequences that bind small target molecules of industrial importance, e.g., metals such as nickel, β carotene, and isoflavones such as genistein. Also described are fusion proteins containing such binding domains fused to proteins or to peptide domains like GST or CBD that bind other ligands and can be used to immobilize the target binding domain on a support. One class of fusion proteins that is useful in industrial settings are fusions that contain concatemers of target binding domains, which increases the binding equivalents per molecule.

6 Claims, 22 Drawing Sheets

(56) References Cited

OTHER PUBLICATIONS

"U.S. Appl. No. 13/575,834, Response filed Jun. 19, 2015 to Final Office Action mailed May 21, 2015", 10 pgs.
"U.S. Appl. No. 13/575,834, Response filed Aug. 5, 2014 to Final Office Action mailed Jun. 5, 2014", 9 pgs.
"U.S. Appl. No. 13/575,834, Response filed Nov. 25, 2013 to Restriction Requirement mailed Sep. 5, 2013", 10 pgs.
"U.S. Appl. No. 13/575,834, Restriction Requirement mailed Sep. 5, 2013", 9 pgs.
"U.S. Appl. No. 14/968,406, Notice of Allowance mailed Aug. 16, 2016", 7 pgs.
"U.S. Appl. No. 14/968,406, Preliminary Amendment filed Dec. 14, 2015", 4 pgs.
"Chinese Application Serial No. 201180016922,6, Decision on Rejection mailed Mar. 1, 2016", (w/ English Translation), 15 pgs.
"Chinese Application Serial No. 201180016922.6, Office Action mailed Jan. 13, 2014", (w/ English Translation), 21 pgs.
"Chinese Application Serial No. 201180016922.6, Office Action mailed Feb. 10, 2015", (w/ English Translation), 11 pgs.
"Chinese Application Serial No. 201180016922.6, Office Action mailed Jul. 23, 2015", (w/ English Translation), 18 pgs.
"Chinese Application Serial No. 201180016922.6, Office Action mailed Aug. 21, 2014", (w/ English Translation), 11 pgs.
"Chinese Application Serial No. 201180016922.6, Request for Reexamination filed Jun. 15, 2016", (English Translation of Claims), 13 pgs.
"Chinese Application Serial No. 201180016922.6, Response filed Jan. 4, 2015 to Office Action mailed Aug. 21, 2014", (w/ English Translation of Claims), 11 pgs.
"Chinese Application Serial No. 201180016922.6, Response filed Apr. 21, 2015 to Office Action mailed Feb. 10, 2015", (w/ English Summary), 4 pgs.
"Chinese Application Serial No. 201180016922.6, Response filed May 27, 2014 to Office Action mailed Jan. 13, 2014", (w/ English Translation of Claims), 17 pgs.
"Chinese Application Serial No. 201180016922.6, Response filed Nov. 6, 2015 to Office Action mailed Jul. 23, 2015", (w/English Translation of Claims), 13 pgs.
"European Application Serial No. 11704507.0, Response filed Dec. 15, 2014 to Examination Notification Art. 94(3) mailed Jun. 6, 2014", 12 pgs.
"European Application Serial No. 11704507.0, Communication Pursuant to Article 94(3) EPC mailed May 4, 2016", 3 pgs.
"European Application Serial No. 11704507.0, Examination Notification Art. 94(3) mailed Jun. 6, 2014", 4 pgs.
"European Application Serial No. 12187018.2, Communication Pursuant to Article 94(3) EPC, mailed May 19, 2016", 3 pgs.
"European Application Serial No. 12187018.2, Examination Notification Art. 94(3) mailed Jun. 6, 2014", 4 pgs.
"European Application Serial No. 12187018.2, Extended European Search Report mailed Feb. 22, 2013", 6 pgs.
"European Application Serial No. 12187018.2, Response filed Dec. 15, 2014 to Examination Notification Art. 94(3) mailed Jun. 6, 2014", 9 pgs.
"European Application Serial No. 12187018.2, Response filed Dec. 21, 2012 Invitation to Remedy Deficiencies mailed Oct. 17, 2012", 7 pgs.
"European Application Serial No. 12187020.8, Examination Notification Art. 94(3) mailed Jun. 12, 2014", 3 pgs.
"European Application Serial No. 12187020.8, Extended European Search Report mailed Feb. 22, 2013", 6 pgs.
"European Application Serial No. 12187020.8, Office Action mailed Jun. 14, 2016", 182 pgs.
"European Application Serial No. 12187020.8, Response filed Dec. 17, 2014 to Examination Notification Art. 94(3) mailed Jun. 12, 2014", 105 pgs.
"European Application Serial No. 12187020.8, Response field Dec. 21, 2012 to Remedy Deficiencies mailed Oct. 17, 2012", 7 pgs.
"GPMAW lite", [online]. [retrieved on May 14, 2015]. Retrieved from the Internet: <lhttp://www.alphalyse.com/gpmaw_lite.html>, (2015), 1 pg.
"International Application Serial No. PCT/US2011/023030, International Preliminary Report on Patentability mailed Jul. 3, 2012", 28 pgs.
"International Application Serial No. PCT/US2011/023030, International Search Report mailed Jul. 28, 2011", 9 pgs.
"International Application Serial No. PCT/US2011/023030, Invitation to Pay Additional Fee mailed May 10, 2011", 10 pgs.
"International Application Serial No. PCT/US2011/023030, Response filed Apr. 13, 2012 to Written Opinion mailed Feb. 13, 2012", 18 pgs.
"International Application Serial No. PCT/US2011/023030, Written Opinion mailed Feb. 13, 2012", 9 pgs.
"International Application Serial No. PCT/US2011/023030, Witten Opinion mailed Jul. 28, 2011", 12 pgs.
Ambevich, Victor I, et al., "Improved design of stable and fast-folding model proteins", *Folding and Design*, vol. 1(3), (1996), 221-230.
Battistoni, Andrea, et al., "A Histidine-rich Metal Binding Domain at the N Terminus of Cu,Zn-Superoxide Dismutases from Pathogenic Bacteria", *J Biological Chemistry*, vol. 276, No. 32, (2001), 30315-30325.
Dexter, Annette F., et al., "Interfacial and Emulsifying Properties of Designed β-Strand Peptides", Langmuir, 26(23), (Dec. 7, 2010), 17997-8007.
Dexter, Annette F., "Interacial and Emulsifying Properties of Designed Beta-Strand Peptides", *Langmuir:The ACS Journal of Surfaces and Colloids*, vol. 26, No. 23, (2010), 17997-18007.
Dong, Jie, et al., "Selection of Novel Nickel-Binding Peptides from Flagella Displayed Secondary Peptide Library", *Chem Biol Drug Des*., 68(2), (Aug. 2006), 107-112.
Gojobori, Takashi, "Curated genome annotation of *Oryza sativa* ssp. *japonica* and comparative genome analysis with *Arabidopsis thaiiana*", *Genome Research*, 17(2), (Feb. 2007), 175-183.
Hulsbergen, F B, et al., "Coordination compounds of tripeptides and pentapeptides containing $_L$-histidyl residues. Studies towards structural models for the active site of cooper proteins", *Recueil des Travaus Chimiques des Pays-Bas*, 112(5), (Jan. 1993), 278-286.
Janssen, G. G, et al., "Selective targeting of a laccase from *Stachybotrys chartarum* covalently linked to a carotenoid-binding peptide", *Journal of Peptide Research*, 64(1), (Jul. 2004), 10-24.
Lui, Feng, et al., "New Perspectives on Host-Parasite Interplay by Comparative Transcriptomic and Proteomic Analyses of *Schistosoma japonicum*", *PLOS Pathogens*, 2(4), (2006), 268-281.
Pike, Ashley C, et al., "Crystal structures of guinea-pig, goat and bovine alpha-lactalbumin highlight the enhanced conformational flexibility of regions that are significant for its action in lactose synthase", *Structure*, 4(6), (Jun. 15, 1996), 691-703.
Roh, Hyun C., et al., "*ttm*--1 Encodes CDF Transporters That Excrete Zinc from Intestinal Cells of *C. elegans* and Act in a Parrallel Negative Feedback Circuit That Promotes Homeostasis"*PLOS Genetics*, vol. 9, (2013), 1-17.
Stover, C. K., et al., "Complete Genome Sequence of Pseudomonas aeruginosa PA01, an Opportunistic Pathogen", *Nature*, vol. 406, (2000), 959-964.
Yanaihara, Noboru, et al., "Synthesis of Polypeptides Related to Porcine Proinsulin", *Diabetes*, vol. 21, No. Suppl 2, (1972), 476-485.
You, L. L, et al., "Recovery of palm carotene from palm oil and hydrolyzed palm oil by adsorption column chromatography", *Journal of Food Lipids*, 9(2), (Jun. 2002), 87-93.
European Application Serial No. 11704507.0, Invitation pursuant to Article 94(3) and Rule 71(1) EPC mailed Feb. 3, 2017, 5 pgs.
European Application Serial No. 12187018.2, Invitation pursuant to Article 94(3) and Rule 71(1) EPC mailed Mar. 6, 2017, 5 pgs.

\* cited by examiner

CONCATAMER CONSTRUCT DESIGN

```
      EcoRI SmaI                             NdeI
  1   GAATTCCCCG GGTTTAAGAA GGAGATATAC ATATGGGTCT GAACTCAGGC
                            [RBS]      [M   G   L   N   S   G

51   CTCACGACAA ATCCTGGTGT ATCCGCTTGG CAGGTCAACA CAGCTTATAC
       L   T   T   N   P   G   V   S   A   W   Q   V   A   T   A   Y   T

101   TGCGGGACAA TTGGTCACAT ATAACGGCAA GACGTATAAA TGTTTGCAGC
       A   G   Q   L   V   T   Y   N   G   K   T   Y   K   C   L   Q   P

151   CCCACACCTC CTTGGCAGGA TGGGAACCAT CCAACGTTCC TGCCTTGTGG
       H   T   S   L   A   G   W   E   P   S   N   V   P   A   L   W]
                                                              SfiI
                                                           PspOMI
201   CAGCTTCAAG GTGGCTCTGG TGGCCTGGAA GTTCTGTTCC AGGGGCCCGG
       Q   L   Q] [G   G   S   G] [G   L   E   V   L   F   Q   G   P] G
                                                              SphI
251   CCCAGCCGGC CGTTATACGC GTACACCTCA TGTGCACTGG CATGCGCACG
       P   A   G   R [Y   T   R   T   P   H   V   H   W   H   A   H   G

301   GCGGTTCTTG GGGCGGATGG CGACACGTAC ACGGTCATCG TCATCCCGGA
       G   S] [W   G   G   W   R   H   V   H   G   H   R   H   P   G

351   GGATCATACA CCCGGACTCC GCACGTACAT TGGCACGCAC ATGGAGGCTC
       G   S] [Y   T   R   T   P   H   V   H   W   H   A   H   G | G   S]
                            NcoI                              BamHI
401   GTGGGGTGGG TGGCGCCATG TCCATGGCCA CCGACACCCT GGGGGATCCT
       W   G   G   W   R   H   V   H   G   H   R   H   P   G   S] [Y
                                                              NotI
451   ACACACGCAC GCCACATGTC CATTGGCACG CTCACGGGGG CGGCCGCGAC
       T   R   T   P   H   V   H   W   H   A   H   G] G   G   R [D
                                       SacI
                              HindIII  XhoI
501   TACAAGGATG ACGATGACAA GTAATAGAAG CTTGAGCTCG AG
       Y   K   D   D   D   D   K] *1 *2
```

| CBD | LINKER | PRECISION | A15 | B16 | FLAG |
|---|---|---|---|---|---|

*FIG. 5*

SEQUENCES RECOGNIZING BETA-CAROTENE FROM PRIMARY SCREENING

```
V S H Y I P R F R I L H G P F S G V G W S
* V S Y E E T L F Y S G W P W Y V D M P R
  W S Y W L Y P F G G F W F S S T N D L H A
S                 Y G W M W S W D L S P R M R E H I A
N N H L R D D S L L A T G W V

Sequences recognizing beta-carotene from secondary screening

Secondary library

-X  X  G  W  X  Hy  X  X  X-

Clones from Secondary library

| | | | | | | | | |
|---|---|---|---|---|---|---|---|---|
| V | A | G | W | W | W | W | G | T | x4 |
| W | A | G | W | M | W | W | W | G | x4 |
| L | A | G | W | G | W | W | G | W | x3 |
| V | A | G | W | W | W | W | G | A | x3 |
| W | A | G | W | G | W | W | S | W | x3 |
| Q | A | G | W | G | W | W | W | G | x3 |
| S | A | G | W | G | W | M | W | W | x2 |
| W | G | G | W | G | W | W | W | G | x2 |
| W | C | G | W | W | W | W | G | W | |
| Y | A | G | W | F | W | G | W | M | |
| L | A | G | W | L | W | W | W | G | |
| F | A | G | W | F | W | W | G | T | |
| T | A | G | W | W | W | G | P | W | |
| A | C | G | W | Y | F | P | S | N | |
| F | G | G | W | W | W | T | W | W | |
| A | I | G | W | P | W | W | L | V | |
| I | A | G | W | L | Y | W | W | A | |
| W | W | G | W | G | W | G | Q | W | |
| L | G | G | W | S | W | H | A | G | |
| T | A | G | W | W | W | G | P | W | |
| F | C | G | W | L | W | P | W | W | |
| A | V | G | W | G | W | W | W | G | |

*FIG. 7*

Peptides binding to Genistein pH 4.0 elution

| | | | | | | | | | | | | | | | | | | | |
|---|---|---|---|---|---|---|---|---|---|---|---|---|---|---|---|---|---|---|---|
| S | L | G | L | W | H | S | Q | R | H | F | D | V | H | R | E | H | S | R | H | Q | T(10) |
| E | F | A | A | I | D | R | V | R | L | F | V | D | K | L | D | N | I | A | Q | V |
| F | H | I | G | K | L | V | S | G | V | A | E | L | L | D | S | G | A | R | W | H |
| Q | R | L | P | W | G | E | W | L | G | K | V | L | S | L | S | E | S | P | W | H | H |
| D | S | R | V | Q | G | L | G | L | A | S | F | W | T | D | G | V | F | V | G | T | A |
| P | A | S | L | S | S | P | A | I | T | P | L | K | S | S | W | W | S | T | I | G | A |
| T | A | G | V | S | Y | F | R | E | P | V | M | L | T | T | W | V | L | R | A | W | A |
| T | T | G | G | L | G | G | P | I | G | H | S | L | H | Q | H | G | L | K | F | R | A |
| M | R | H | Q | R | V | T | F | P | A | H | I | C | Y | I | C | A | F | W | Q | P | A | pH 3.0 elution

| I | T | F | F | P | Y | K | L | L | H | G | L | T | N | Y | V | I | G | L | Q | R | N(2) |
|---|---|---|---|---|---|---|---|---|---|---|---|---|---|---|---|---|---|---|---|---|---|
| H | L | V | R | V | G | M | E | N | L | H | A | A | S | N | F | L | F | G | S | L | F |
| H | V | A | S | H | P | F | G | A | L | S | R | V | M | L | F | L | L | D | K | L | N |
| N | E | A | Y | N | E | K | A | N | E | T | P | T | L | N | G | K | V | D | K | C | P |
| I | P | L | G | L | A | F | A | A | M | P | G | T | L | A | D | Q | I | L | R | H | H |
| L | D | Y | M | L | E | A | L | L | H | Y | T | F | P | R | A | T | Q | H | P | H | I | pH 1.0 elution

| R | P | L | M | F | T | P | P | S | A | I | S | R | L | M | H | H | G | N | H | M | S(2) |
|---|---|---|---|---|---|---|---|---|---|---|---|---|---|---|---|---|---|---|---|---|---|
| K | V | F | P | F | V | N | H | V | V | D | T | A | G | W | F | I | T | L | F | K | Y |
| T | N | G | L | A | Q | L | L | N | L | S | F | L | T | N | F | I | T | L | L | R | S |
| R | D | L | C | S | S | I | S | H | S | D | R | V | K | G | C | I | R | P | L | S | P |
| Y | Q | W | L | I | L | S | M | K | S | I | A | P | N | I | A | P | S | K | Q | H | S |
| D | V | N | D | E | F | V | W | R | F | R | S | Y | I | H | P | I | V | A | N | F | L |
| I | L | P | G | F | H | G | L | I | Q | N | L | T | H | Y | L | W | K | T | I | G | F |

*FIG. 8*

| ID | Sequence | # Histidines | ka | kd | Kd (M) |
|---|---|---|---|---|---|
| C29 | IPHRHQFHHTAHA | 5 | 2.3x10$^3$ | 4.6x10$^{-9}$ | 2.0x10$^{-12}$ |
| A15 | YTRTPHVHWHAHG | 4 | 1.1x10$^5$ | 9.9x10$^{-8}$ | 9.1x10$^{-13}$ |
| A8 | IGGWSHHHLGRTA | 3 | 7.7x10$^4$ | 3.8x10$^{-7}$ | 5.0x10$^{-12}$ |
| B16 | WGGWRHVHGHRHP | 4 | 3.0x10$^4$ | 7.0x10$^{-8}$ | 2.3x10$^{-12}$ |
| C10 | EWHRHIRHPEVLA | 4 | 2.4 x 10$^4$ | 2.6x10$^{-8}$ | 1.1x10$^{-12}$ |
| A18 | PHPPRHHHGLRAP | 4 | 3.1x10$^4$ | 1.7x10$^{-7}$ | 5.5x10$^{-12}$ |
| B4 | HAAGHHHHGWWRP | 5 | 2.7x10$^4$ | 7.0x10$^{-8}$ | 2.6x10$^{-12}$ |
| C11 | WGGGKHHHRGPG | 4 | 2.2x10$^4$ | 1.2x10$^{-6}$ | 5.2x10$^{-12}$ |
| C28 | IRHHGHDKLTHA | 4 | 4.2x10$^3$ | 4.0x10$^{-6}$ | 9.4x10$^{-12}$ |
| B17 | HGHWRJTHTGDRG | 4 | 3.3x10$^4$ | 3.1x10$^{-6}$ | 9.5x10$^{-11}$ |
| C26 | YSHHHHHLAGTA | 6 | 2.1x10$^4$ | 4.8x10$^{-7}$ | 2.3x10$^{-11}$ |
| A10 | HYHYMHRHSGSSP | 4 | 3.7x10$^4$ | 3.8x10$^{-7}$ | 1.0x10$^{-11}$ |
| C31 | PHHVHTHGARGGG | 4 | 2.2x10$^4$ | 3.2x10$^{-7}$ | 1.5x10$^{-11}$ |
| C22 | HNHGLHLHGGERG | 4 | 2.2x10$^4$ | 9.8x10$^{-6}$ | 4.4x10$^{-10}$ |
| A12 | IGHLMHGHRSSYT | 3 | 8.6x10$^4$ | 8.6x10$^{-4}$ | 7.1x10$^{-9}$ |
| B6 | LAYRWHHHWGPA | 4 | 2.9x10$^5$ | 3.7x10$^{-3}$ | 1.3x10$^{-8}$ |
| C46 | LAIVRHSHSLGIG | 2 | 8.3 x 10$^5$ | 4.5x10$^{-4}$ | 5.4x10$^{-7}$ |
| C23 | TVVHKHGHHVRGG | 4 | n/a | | |
| C30 | RHHHHDPRGGGWP | 4 | n/a | | |

FIG. 9

| Peptide | ALA* | ARG* | ASN | ASP | CYS | GLN | GLU | GLY* | HIS* | ILEU* | LEU | LYS | MET | PHE | PRO* | SER | THR | TRP | TYR | VAL | # (+ive) residues | # (-ive) residues | pI |
|---|---|---|---|---|---|---|---|---|---|---|---|---|---|---|---|---|---|---|---|---|---|---|---|
| C29 | 2 | 1 | | | | | | | 5 | 1 | | | | | 1 | | | | | | 1 | | 9.78 |
| A15 | 1 | 1 | | | | | | 1 | 4 | | | | | | | | 2 | 1 | 1 | 1 | 1 | | 8.78 |
| A8 | 1 | 1 | | | | | | 3 | 3 | 1 | 1 | | | | 1 | | 1 | 1 | | | 1 | | 9.77 |
| B16 | | 2 | | | | | | 3 | 4 | | | | | | | 1 | | 2 | | 1 | 2 | | 12 |
| C10 | 1 | 2 | | | | | 2 | | 4 | | 1 | | | | 1 | | | 1 | | | 2 | 2 | 7.19 |
| A18 | 1 | 2 | | | | | | 1 | 4 | | | | | 1 | 3 | | | | | | 2 | | 12 |
| B4 | 2 | 1 | | | | | | 2 | 5 | | | | | | 1 | | | 2 | | | 1 | | 9.78 |
| C11 | 1 | 1 | | | | | | 5 | 4 | 2 | 1 | 1 | | | 1 | | 1 | 1 | | | 2 | | 11 |
| C28 | | 1 | 1 | | | | | | 4 | | 1 | 1 | 1 | | | | | | | | 2 | 1 | 8.78 |
| B17 | | 1 | 1 | | | | | 3 | 4 | | | | | | | | 2 | 1 | | | 2 | 1 | 9.62 |
| C26 | 2 | | | | | | | 1 | 6 | | 1 | | | | 1 | 1 | 1 | 1 | 1 | | | | 7.2 |
| A10 | | 1 | | | | | | 1 | 4 | | | | 1 | | 1 | 3 | | | 2 | | 1 | | 8.62 |
| C31 | 1 | 1 | | | | | | 4 | 4 | | | | | | 1 | | 1 | | | 1 | 1 | | 10.18 |
| C22 | | 1 | 1 | | | | 1 | 4 | 4 | 1 | 2 | | 1 | | | 2 | 1 | | | | 1 | 1 | 7.1 |
| A12 | | 1 | | | | | | 2 | 3 | | 1 | | | | 1 | | 1 | | | 1 | 1 | | 9.77 |
| B6 | 2 | 1 | | | | | | 1 | 4 | | 1 | | | | 1 | | | 2 | 1 | | 1 | | 8.78 |
| C46 | 1 | 1 | | | | | | 2 | 2 | 1 | 2 | | | | | 2 | | | | 1 | 1 | | 9.76 |
| | 65% | 94% | 5.80% | 12.00% | 0% | 0% | 6.00% | 82% | 100% | 29% | 47% | 12% | 12% | 12% | 59% | 29% | 41% | 47% | 24% | 35% | | | |

FIG. 10

SUMO-CBD-5x Ni binding motif concatamer (expressed in pE-
SUMO vector from Lifesensors but with the N-terminal His-tag removed)

```
  1 ATGGGGTCCC TGCAGGACTC AGAAGTCAAT CAAGAAGCTA AGCCAGAGGT
    M    G    S    L    Q    D    S    E    V    N    Q    E    A    K    P    E    V

51 CAAGCCAGAA GTCAAGCCTG AGACTCACAT CAATTTAAAG GTGTCCGATG
    K    P    E    V    K    P    E    T    H    I    N    L    K    V    S    D    G

101 GATCTTCAGA GATCTTCTTC AAGATCAAAA AGACCACTCC TTTAAGAAGG
    S    S    E    I    F    F    K    I    K    K    T    T    P    L    R    R

151 CTGATGGAAG CGTTCGCTAA AAGACAGGGT AAGGAAATGG ACTCCTTAAG
    L    M    E    A    F    A    K    R    Q    G    K    E    M    D    S    L    R

201 ATTCTTGTAC GACGGTATTA GAATTCAAGC TGATCAGGCC CCTGAAGATT
    F    L    Y    D    G    I    R    I    Q    A    D    Q    A    P    E    D    L

251 TGGACATGGA GGATAACGAT ATTATTGAGG CTCACCGCGA ACAGATTGGA
    D    M    E    D    N    D    I    I    E    A    H    R    E    Q    I    G

301 GGTGGAGACC GCGAGAACCT GTACTTTCAG GGCGGTCTGA ACTCAGGCCT
    G    G    D    R    E    N    L    Y    F    Q    G    G    L    N    S    G    L

351 CACGACAAAT CCTGGTGTAT CCGCTTGGCA GGTCAACACA GCTTATACTG
    T    T    N    P    G    V    S    A    W    Q    V    N    T    A    Y    T    A

401 CGGGACAATT GGTCACATAT AACGGCAAGA CGTATAAATG TTTGCAGCCC
    G    Q    L    V    T    Y    N    G    K    T    Y    K    C    L    Q    P

451 CACACCTCCT TGGCAGGATG GGAACCATCC AACGTTCCTG CCTTGTGGCA
    H    T    S    L    A    G    W    E    P    S    N    V    P    A    L    W    Q

501 GCTTCAAGGT GGCTCTGGTG GCCTGGAAGT TCTGTTCCAG GGGCCCGGCC
    L    Q    G    G    S    G    G    L    E    V    L    F    Q    G    P    G    P

551 CAGCCGGCCG TTATACGCGT ACACCTCATG TGCACTGGCA TGCGCACGGC
    A    G    R    Y    T    R    T    P    H    V    H    W    H    A    H    G

601 GGTTCTTGGG GCGGATGGCG ACACGTACAC GGTCATCGTC ATCCCGGAGG
    G    S    W    G    G    W    R    H    V    H    G    H    R    H    P    G    G

651 ATCATACACC CGGACTCCGC ACGTACATTG GCACGCACAT GGAGGCTCGT
    S    Y    T    R    T    P    H    V    H    W    H    A    H    G    G    S    W

701 GGGGTGGGTG GCGCCATGTC CATGGCCACC GACACCCTGG GGGTTCCTAC
    G    G    W    R    H    V    H    G    H    R    H    P    G    G    S    Y

751 ACACGCACGC CACATGTCCA TTGGCACGCT CACGGGGGCG GCCGCGACTA
    T    R    T    P    H    V    H    W    H    A    H    G    G    G    R    D    Y

801 CAAGGATGAC GATGACAAGT AATAG
    K    D    D    D    D    K    *    *
```

FIG. 12F

6xHis-SUMO-CBD fusion 2x concatenated Beta-Carotene binding motifs

```
  1 ATGGGTCATC ACCATCATCA TCACGGGTCC CTGCAGGACT CAGAAGTCAA
    M  G  H  H  H  H  H  G  S  L  Q  D  S  E  V  N

51 TCAAGAAGCT AAGCCAGAGG TCAAGCCAGA AGTCAAGCCT GAGACTCACA
    Q  E  A  K  P  E  V  K  P  E  V  K  P  E  T  H  I

101 TCAATTTAAA GGTGTCCGAT GGATCTTCAG AGATCTTCTT CAAGATCAAA
    N  L  K  V  S  D  G  S  S  E  I  F  F  K  I  K

151 AAGACCACTC CTTTAAGAAG GCTGATGGAA GCGTTCGCTA AAAGACAGGG
    K  T  T  P  L  R  R  L  M  E  A  F  A  K  R  Q  G

201 TAAGGAAATG GACTCCTTAA GATTCTTGTA CGACGGTATT AGAATTCAAG
    K  E  M  D  S  L  R  F  L  Y  D  G  I  R  I  Q  A

251 CTGATCAGGC CCCTGAAGAT TTGGACATGG AGGATAACGA TATTATTGAG
    D  Q  A  P  E  D  L  D  M  E  D  N  D  I  I  E

301 GCTCACCGCG AACAGATTGG AGGTGGAGAC CGCGAGAACC TGTACTTTCA
    A  H  R  E  Q  I  G  G  G  D  R  E  N  L  Y  F  Q

351 GGGCGGTCTG AACTCAGGCC TCACGACAAA TCCTGGTGTA TCCGCTTGGC
    G  G  L  N  S  G  L  T  T  N  P  G  V  S  A  W  Q

401 AGGTCAACAC AGCTTATACT GCGGGACAAT TGGTCACATA TAACGGCAAG
    V  N  T  A  Y  T  A  G  Q  L  V  T  Y  N  G  K

451 ACGTATAAAT GTTTGCAGCC CCACACCTCC TTGGCAGGAT GGGAACCATC
    T  Y  K  C  L  Q  P  H  T  S  L  A  G  W  E  P  S

501 CAACGTTCCT GCCTTGTGGC AGCTTCAAGG TGGCTCTGGT GGCCTGGAAG
    N  V  P  A  L  W  Q  L  Q  G  G  S  G  G  L  E  V

551 TTCTGTTCCA GGGGCCCGGC CCAGCCGGCC AACAGGCGGG CTGGGGTTGG
    L  F  Q  G  P  G  P  A  G  Q  Q  A  G  W  G  W

601 TGGTGGGGTG GTAGCGGCCA GGCGGGCTGG GGTTGGTGGT GGGGTGGCGG
    W  W  G  G  S  G  Q  A  G  W  G  W  W  G  G

651 CCGCGACTAC AAGGATGACG ATGACAAGTA ATAG
    R  D  Y  K  D  D  D  D  K  *  *
```

*FIG. 12G*

MBP fused 2x Beta-Carotene binding motifs (using pMALc5E vector from New England Biolabs)

```
  1 ATGAAAATCG AAGAAGGTAA ACTGGTAATC TGGATTAACG GCGATAAAGG
    M   K   I   E   E   G   K   L   V   I   W   I   N   G   D   K   G

51 CTATAACGGT CTCGCTGAAG TCGGTAAGAA ATTCGAGAAA GATACCGGAA
    Y   N   G   L   A   E   V   G   K   K   F   E   K   D   T   G   I

101 TTAAAGTCAC CGTTGAGCAT CCGGATAAAC TGGAAGAGAA ATTCCCACAG
    K   V   T   V   E   H   P   D   K   L   E   E   K   F   P   Q

151 GTTGCGGCAA CTGGCGATGG CCCTGACATT ATCTTCTGGG CACACGACCG
    V   A   A   T   G   D   G   P   D   I   I   F   W   A   H   D   R

201 CTTTGGTGGC TACGCTCAAT CTGGCCTGTT GGCTGAAATC ACCCCGGACA
    F   G   G   Y   A   Q   S   G   L   L   A   E   I   T   P   D   K

251 AAGCGTTCCA GGACAAGCTG TATCCGTTTA CCTGGGATGC CGTACGTTAC
    A   F   Q   D   K   L   Y   P   F   T   W   D   A   V   R   Y

301 AACGGCAAGC TGATTGCTTA CCCGATCGCT GTTGAAGCGT TATCGCTGAT
    N   G   K   L   I   A   Y   P   I   A   V   E   A   L   S   L   I

351 TTATAACAAA GATCTGCTGC CGAACCCGCC AAAAACCTGG GAAGAGATCC
    Y   N   K   D   L   L   P   N   P   P   K   T   W   E   E   I   P

401 CGGCGCTGGA TAAAGAACTG AAAGCGAAAG GTAAGAGCGC GCTGATGTTC
    A   L   D   K   E   L   K   A   K   G   K   S   A   L   M   F

451 AACCTGCAAG AACCGTACTT CACCTGGCCG CTGATTGCTG CTGACGGGGG
    N   L   Q   E   P   Y   F   T   W   P   L   I   A   A   D   G   G

501 TTATGCGTTC AAGTATGAAA ACGGCAAGTA CGACATTAAA GACGTGGGCG
    Y   A   F   K   Y   E   N   G   K   Y   D   I   K   D   V   G   V

551 TGGATAACGC TGGCGCGAAA GCGGGTCTGA CCTTCCTGGT TGACCTGATT
    D   N   A   G   A   K   A   G   L   T   F   L   V   D   L   I

601 AAAAACAAAC ACATGAATGC AGACACCGAT TACTCCATCG CAGAAGCTGC
    K   N   K   H   M   N   A   D   T   D   Y   S   I   A   E   A   A

651 CTTTAATAAA GGCGAAACAG CGATGACCAT CAACGGCCCG TGGGCATGGT
    F   N   K   G   E   T   A   M   T   I   N   G   P   W   A   W   S

701 CCAACATCGA CACCAGCAAA GTGAATTATG GTGTAACGGT ACTGCCGACC
    N   I   D   T   S   K   V   N   Y   G   V   T   V   L   P   T

751 TTCAAGGGTC AACCATCCAA ACCGTTCGTT GGCGTGCTGA GCGCAGGTAT
    F   K   G   Q   P   S   K   P   F   V   G   V   L   S   A   G   I

801 TAACGCCGCC AGTCCGAACA AAGAGCTGGC AAAAGAGTTC CTCGAAAACT
```

FIG. 12H

```
             N   A   A    S   P   N   K    E   L   A   K   E   F    L   E   N   Y
 851 ATCTGCTGAC TGATGAAGGT CTGGAAGCGG TTAATAAAGA CAAACCGCTG
       L   L   T    D   E   G    L   E   A   V    N   K   D    K   P   L

901 GGTGCCGTAG CGCTGAAGTC TTACGAGGAA GAGTTGGTGA AAGATCCGCG
       G   A   V    A    L   K   S    Y   E   E    E   L   V   K    D   P   R

951 TATTGCCGCC ACTATGGAAA ACGCCCAGAA AGGTGAAATC ATGCCGAACA
       I   A   A    T   M   E   N    A   Q   K    G   E   I    M   P   N   I

1001 TCCCGCAGAT GTCCGCTTTC TGGTATGCCG TGCGTACTGC GGTGATCAAC
       P   Q   M    S   A   F    W   Y   A   V    R   T   A    V   I   N

1051 GCCGCCAGCG GTCGTCAGAC TGTCGATGAA GCCCTGAAAG ACGCGCAGAC
       A   A   S   G    R   Q   T    V   D   E    A   L   K   D    A   Q   T

1101 TAATTCGAGC TCGAACAACA ACAACAATAA CAATAACAAC AACCTCGGGG
       N   S   S    S   N   N    N   N   N    N   N   N    N   L   G   D

1151 ATGACGATGA CAAGGTACCG CATATGCCAG CCGGCCAACA GGCGGGCTGG
       D   D   D    K   V   P    H   M   P    A   G   Q   Q    A   G   W

1201 GGTTGGTGGT GGGGTGGTAG CGGCCAGGCG GGCTGGGGTT GGTGGTGGGG
       G   W   W   W    G   G   S    G   Q   A    G   W   G   W    W   G

1251 TGGCGGCCGC GACTACAAGG ATGACGATGA CAAGTAATAG AAGCTT
       G   G   R    D   Y   K   D    D   D   D    K   *
```

*FIG. 12I*

MBP-CBD fusion 2x concatenated Beta-Carotene binding motif

```
  1 ATGAAAATCG AAGAAGGTAA ACTGGTAATC TGGATTAACG GCGATAAAGG
      M  K  I  E  E  G  K  L  V  I  W  I  N  G  D  K  G

51 CTATAACGGT CTCGCTGAAG TCGGTAAGAA ATTCGAGAAA GATACCGGAA
      Y  N  G  L  A  E  V  G  K  K  F  E  K  D  T  G  I

101 TTAAAGTCAC CGTTGAGCAT CCGGATAAAC TGGAAGAGAA ATTCCCACAG
      K  V  T  V  E  H  P  D  K  L  E  E  K  F  P  Q

151 GTTGCGGCAA CTGGCGATGG CCCTGACATT ATCTTCTGGG CACACGACCG
      V  A  A  T  G  D  G  P  D  I  I  F  W  A  H  D  R

201 CTTTGGTGGC TACGCTCAAT CTGGCCTGTT GGCTGAAATC ACCCCGGACA
      F  G  G  Y  A  Q  S  G  L  L  A  E  I  T  P  D  K

251 AAGCGTTCCA GGACAAGCTG TATCCGTTTA CCTGGGATGC CGTACGTTAC
      A  F  Q  D  K  L  Y  P  F  T  W  D  A  V  R  Y

301 AACGGCAAGC TGATTGCTTA CCCGATCGCT GTTGAAGCGT TATCGCTGAT
      N  G  K  L  I  A  Y  P  I  A  V  E  A  L  S  L  I

351 TTATAACAAA GATCTGCTGC CGAACCCGCC AAAAACCTGG GAAGAGATCC
      Y  N  K  D  L  L  P  N  P  P  K  T  W  E  E  I  P

401 CGGCGCTGGA TAAAGAACTG AAAGCGAAAG GTAAGAGCGC GCTGATGTTC
      A  L  D  K  E  L  K  A  K  G  K  S  A  L  M  F

451 AACCTGCAAG AACCGTACTT CACCTGGCCG CTGATTGCTG CTGACGGGGG
      N  L  Q  E  P  Y  F  T  W  P  L  I  A  A  D  G  G

501 TTATGCGTTC AAGTATGAAA ACGGCAAGTA CGACATTAAA GACGTGGGCG
      Y  A  F  K  Y  E  N  G  K  Y  D  I  K  D  V  G  V

551 TGGATAACGC TGGCGCGAAA GCGGGTCTGA CCTTCCTGGT TGACCTGATT
      D  N  A  G  A  K  A  G  L  T  F  L  V  D  L  I

601 AAAAACAAAC ACATGAATGC AGACACCGAT TACTCCATCG CAGAAGCTGC
      K  N  K  H  M  N  A  D  T  D  Y  S  I  A  E  A  A

651 CTTTAATAAA GGCGAAACAG CGATGACCAT CAACGGCCCG TGGGCATGGT
      F  N  K  G  E  T  A  M  T  I  N  G  P  W  A  W  S

701 CCAACATCGA CACCAGCAAA GTGAATTATG GTGTAACGGT ACTGCCGACC
      N  I  D  T  S  K  V  N  Y  G  V  T  V  L  P  T

751 TTCAAGGGTC AACCATCCAA ACCGTTCGTT GGCGTGCTGA GCGCAGGTAT
      F  K  G  Q  P  S  K  P  F  V  G  V  L  S  A  G  I
```

*FIG. 12J*

```
 801 TAACGCCGCC AGTCCGAACA AAGAGCTGGC AAAAGAGTTC CTCGAAAACT
      N  A  A   S  P  N  K   E  L  A   K  E  F    L  E  N  Y

851 ATCTGCTGAC TGATGAAGGT CTGGAAGCGG TTAATAAAGA CAAACCGCTG
      L  L  T   D  E  G    L  E  A    V  N  K  D  K  P  L

901 GGTGCCGTAG CGCTGAAGTC TTACGAGGAA GAGTTGGTGA AAGATCCGCG
      G  A  V   A  L  K  S  Y  E  E   E  L  V  K  D  P  R

951 TATTGCCGCC ACTATGGAAA ACGCCCAGAA AGGTGAAATC ATGCCGAACA
      I  A  A   T  M  E   N  A  Q  K  G  E  I    M  P  N  I

1001 TCCCGCAGAT GTCCGCTTTC TGGTATGCCG TGCGTACTGC GGTGATCAAC
      P  Q  M   S  A  F    W  Y  A    V  R  T  A  V  I  N

1051 GCCGCCAGCG GTCGTCAGAC TGTCGATGAA GCCCTGAAAG ACGCGCAGAC
      A  A  S   G  R  Q  T  V  D  E  A  L  K    D  A  Q  T

1101 TAATTCGAGC TCGAACAACA ACAACAATAA CAATAACAAC AACCTCGGGG
      N  S  S   S  N  N    N  N  N   N  N  N    N  L  G  D

1151 ATGACGATGA CAAGGTACCG CATATGGGCG GTCTGAACTC AGGCCTCACG
      D  D  D   K  V  P   H  M  G    G  L  N  S  G  L  T

1201 ACAAATCCTG GTGTATCCGC TTGGCAGGTC AACACAGCTT ATACTGCGGG
      T  N  P   G  V  S  A  W  Q  V  N  T  A  Y  T  A  G

1251 ACAATTGGTC ACATATAACG GCAAGACGTA TAAATGTTTG CAGCCCCACA
      Q  L  V   T  Y  N   G  K  T  Y  K  C  L    Q  P  H  T

1301 CCTCCTTGGC AGGATGGGAA CCATCCAACG TTCCTGCCTT GTGGCAGCTT
      S  L  A   G  W  E   P  S  N  V  P  A  L    W  Q  L

1351 CAAGGTGGCT CTGGTGGCCT GGAAGTTCTG TTCCAGGGGC CCGGCCCAGC
      Q  G  S   G  G  L   E  V  L    F  Q  G  P  G  P  A

1401 CGGCCAACAG GCGGGCTGGG GTTGGTGGTG GGGTGGTAGC GGCCAGGCGG
      G  Q  Q   A  G  W   G  W  W    G  G  S    G  Q  A  G

1451 GCTGGGGTTG GTGGTGGGGT GGCGGCCGCG ACTACAAGGA TGACGATGAC
      W  G  W   W  G      G  G  R  D  Y  K  D   D  D  D

1501 AAGTAATAG
      K  *  *
```

*FIG. 12K*

… # PEPTIDE DOMAINS THAT BIND SMALL MOLECULES

CROSS-REFERENCE TO RELATED APPLICATIONS

This application is a divisional of and claims the benefit of priority under 35 U.S.C. §120 to U.S. patent application Ser. No. 13/575,834, filed on Jul. 27, 2012, which is a U.S. National Stage Filing under 35 U.S.C. 371 from International Application No. PCT/US2011/023030, filed on Jan. 28, 2011, and published as WO 2011/094617 A2 on Aug. 4, 2011, which application claims the benefit of the filing date of U.S. application Ser. No. 61/299,449, filed on Jan. 29, 2010, the disclosures of which are incorporated by reference herein.

BACKGROUND

Peptides capable of binding specific target molecules have been useful for a variety of research and product development work in the biological, medical, and pharmaceutical fields. Typically in these fields, the target molecules have been those of biological significance, such as peptide epitopes of diseased or pathogenic cells, surface receptor proteins, signaling proteins, proteins involved in the etiology of biological responses such as immune T cell and B cell responses, and targets that are useful for biological research, for example, proteins that bind to nucleic acids or other proteins of biological interest, to which a specific binding partner is needed for identification and screening purposes.

The most longstanding tool for obtaining peptides with specific target binding activities has come from exploitation of the immune response, originally by obtaining polyclonal antibodies, such as IgGs and IgMs induced in an animal challenged by injection of the target molecule to obtain a B cell response and the isolation of antibodies from blood. Subsequently, monoclonal antibodies were obtained from clones of hybridoma cells that produce a single species of antibody that binds a specific epitope of a target molecule. Useful antibodies have the ability to bind target molecules with a molar dissociation constant (Kd) typically of $10^{-7}$ M or less and more typically $10^{-8}$ M to $10^{-9}$ M. These technologies relied entirely on exploiting the natural biological immune system that is capable of recombining the coding sequences for the hypervariable domains of antibodies to create an enormous diversity of antibodies and that has the ability to naturally stimulate the propagation of the few that bind to the target molecule of interest. In the case of monoclonal antibodies, the naturally induced propagation was replaced by the human made ability to select and culture clones that express the specific antibodies.

While use of antibodies has proven to be a powerful tool for obtaining peptides that bind to specific target molecules, antibodies have limitations in utility for industrial applications. First, they must be made from whole blood, chicken eggs, or from hybridoma tissue cultures—all of which are expensive and low yield production systems in comparison to what would be needed for industrial scale binding of target molecules. Second, they rely on the three dimensional structure of the binding domain formed in the hypervariable region of the antibody molecule, requiring production of a rather large protein (even in the case a single chain variable fragments) to obtain one molar binding equivalent for the relatively smaller peptide domain needed to bind each mole of target molecule.

A more recent alternative to antibodies for the identification of target binding domains was the development of bacterial protein display systems, most notably phage display systems. These systems display peptides or whole protein sequences as fusions with surface proteins, e.g., with phage display the peptides are expressed as fusions with phage particle proteins.

Phage display is one of the most powerful and well established technologies for exploring the sequence space of combinatorial random peptide libraries. Typically, foreign proteins/peptides are expressed on the surface of M13 bacteriophage as fusions to either the minor coat protein pIII or the major coat protein pVIII. Libraries with a diversity of $10^7$-$10^{11}$ peptides (having 5-40 residues) can be screened against the target molecule (immobilized on beads or adsorbed in microtiter wells) and enriched for specific binders through iterative rounds of binding and infection. Binding of individual clones from enriched pools are detected by ELISA and the amino acid sequence of the binding peptide deciphered by sequencing the DNA in the phage particle. The amino acid sequence of the peptide ligands may then be compared to protein databases to identify potential endogenous interacting proteins in silico.

Phage display technology has been primarily useful for identifying protein-protein, protein-peptide and protein-DNA interactions and as such, has been particularly useful as a research tool to identify target peptides that interact with physiologically important proteins, e.g., antibodies and receptors, or that bind to specific sequences of DNA or to potential drug candidates in order to discover potential physiological target proteins for pharmaceutical applications. Phage display, however, has rarely been used to identify peptides that bind to small molecules of industrial importance, such as contaminants in a processing stream or metal ions. While useful as a research tool, phage display has not been shown to be practical as tool for actual production of peptide domains for commercial deployment in any industrial process or product.

A handful of metal binding peptides, however, have been described. One metal binding motif found in metal binding peptides is a sequence of 6 histidines ("polyhistidine"), which is known to be capable of binding nickel. Expression vectors are available that contain nucleic acid sequences with promoters linked to regions encoding polyhistidine containing peptides to make so called "his-tagged" fusion proteins that can quickly be isolated from a cellular extract by relying on the ability of the polyhistidine domain to bind to nickel immobilized on a column. The bound protein is eluted from the column using an excess of imidazole. The polyhistidine binding domain can be cleaved from the eluted protein with a protease if the cloning vector additionally encodes a protease substrate site in-frame with the fusion protein.

The most well known polyhistidine binding domain is a peptide comprising a core sequence of six histidines, as exemplified by the sequence YSHHHHHHLAGTA (SEQ ID NO:1), which has a molar dissociation constant for nickel of $2.3 \times 10^{-11}$ M. Another known polyhistidine binding domain is a 12 amino acid peptide that is a 6 mer repeat of a histidine-glutamine dipeptide, i.e., $(HQ)_6$ (SEQ ID NO:2), Arginine has also been implicated as an important contributing amino acid residue for nickel binding because the consensus sequence RHXHHR (SEQ ID NO:3), where X is most frequently histidine, was also shown to bind nickel with high affinity (Jie et al., *Chemical Biology & Drug Design* (2006) 68:107-112). Jie et al. identified that sequence by screening peptides form a bacterial library engineered to display proteins on flagella and suggested that bacteria displaying such a sequence might be useful as a biologically derived waste water remediation agent.

Using a similar system, a very different motif for a peptide that binds metal was disclosed by Behnaz et al. (*Iranian Journal of Biotechnology* (2005) 3:180-185), which showed that the cysteine rich peptide GCGCPCGCG (SEQ ID NO:4) displayed on the surface of *E. coli* via a fibrinea fusion protein was capable of binding metals in the relative order lead>cadmium>nickel. Regarding cysteine, *E. coli* that displayed on its surface by fusion to the OmpX membrane protein the cysteine containing peptide LCCYWSYS-RMCKN (SEQ ID NO:5) (which was selected from a library of randomly generated 11-mer with two cysteines separated by seven amino acids and each flanked by two amino acids) was shown to bind gold particles in suspension (Kaviani, *Biological Applications NNIN REU* (2006) *Research Accomplishments*, p 12-13). A proline/hydroxy containing gold binding peptide of the sequence LKAHLPPSRLPS (SEQ ID NO:6) was identified by phage display using M13 (Nam et al. *Science* (2006) 312:885-888). Similarly, but in unrelated work, several hydroxyl rich peptides identified by phage surface display, but having no particular consensus sequence, were shown to bind aluminum, with the peptide VPSSGPQDTRTT (SEQ ID NO:7) showing particularly strong binding (Zao et al., *Appl. Microb. and Biotech.* (2005) 68:505-509). Gold binding peptides have been suggested as potentially useful in the assembly of nanostructures for microelectronics. Others have shown that metal binding peptides displayed on M13 phage libraries could be useful for biotemplating catalysts to improve catalytic activity (Nelner et al., *ACS Nano* (2010) 4:3227-3235).

Despite the suggestions, phage display or other bacterial display systems alone are not suitable for deployment in practical industrial scale processes such as water remediation, recovery of precious metals or removal of contaminants from processing streams. This is because the quantity of binding sites needed to bind target molecules from industrial scale processing streams is extremely large. By way of example, a typical phage titer produced via bacterial cell culture is on the order of $10^{12}$ particles per mL. Even assuming each particle displayed $10^3$ binding proteins, each binding one equivalent of a target molecule, it would require $6.02 \times 10^8$ mL, or 602,000 liters of cell culture to produce enough particles just to bind one mole of a target molecule. One mole of nickel is 60 grams of material and a typical water intensive industrial production process, such as processing corn in a 250,000 bushel per day wet mill facility, which uses hundreds of thousands of liters of water per hour, can extract as much as 6 lbs (2700 grams) of nickel in just a three hour period. Therefore, to use the nickel binding domains expressed on phage particles to bind all the nickel produced in one day from a corn wet mill facility, or other agricultural processes that generate large volumes of waste water that contain extracted metals such as nickel, e.g., soybean processing, may use about 218 million liters of phage culture to produce enough particles. Such large scale production is commercially impractical. Display on bacterial surfaces is even less practical because the total number of displayed molecules per bacterium is about the same as phage, but the maximum titer of bacteria is on the order of $10^9$ cells per mL. Therefore, it would require at least 1000 times the amount of bacterial culture to display enough binding sites on flagella or fibrinea as would be required to display the same on a phage particle.

There is a practical, industrial need for specifically binding small molecules from industrial processing streams that would be useful for water remediation, removal of contaminants from food products, and large scale purification of naturally occurring small molecules.

SUMMARY OF THE INVENTION

The present disclosure describes peptides that bind to molecules of industrial importance with high affinities. In one embodiment, peptides having a plurality of histidine residues, which peptides bind metal ions such as Ni, Cu and Zn, and particularly Ni with higher affinity (lower Kd) than, e.g., SEQ ID NO:1, were identified. In another embodiment, peptides that bind contaminants that disadvantageously affect the color, stability or odor of foods, e.g., carotene, were identified. Carotenes are typically co-extracted when processing palm oil and so carotene binding peptides allow for the removal of carotene from palm oil. In still another embodiment, peptides that bind natural products from agricultural sources like isoflavones from soybeans that are useful as nutraceuticals, such as the isoflavone genistein, were identified. The fact that the identified peptides can bind with high specificity to such diverse types of molecules of industrial importance demonstrates that methods such as peptide display systems can be useful for identifying peptides for use in a wide variety of industrial processes. The identified binding peptides may be employed to remove, isolate (purify) or detect (identify) the target molecules, or structurally related molecules, in complex mixtures.

Thus, the invention provides isolated metal binding peptides and fusions of one or more of those peptides, and optionally fusions with other peptides, such as those useful to bind to other molecules and/or a peptide that is a protease substrate, thereby forming a chimeric polypeptide. In one embodiment, the metal binding peptide or fusion thereof also includes a peptide sequence suitable for purification or isolation, e.g., a glutathione S-transferase (GST) or chitin binding peptide sequence. In one embodiment, the fusion includes concatemers of the metal binding peptides, e.g., the fusion has at least two distinct metal binding peptide sequences or at least two of the same metal binding peptide sequences. In one embodiment, a linker sequence separates adjacent metal binding peptide sequences, e.g., to allow for unhindered binding of metal to adjacent binding sites. In one embodiment, the metal binding peptide is at least 5 to about 30 amino acids in length, e.g., from about 10 to about 30 amino acids (or any integer in between 5 and 30) in length, such as 10 to 15 amino acids in length. Fusions of a plurality of metal binding peptides, including fusions with the same peptide sequence or different peptide sequences, may be of any length. In one embodiment, the fusion is no more than 1000 amino acids in length. In another embodiment, the fusion is no more than 500 amino acids in length. In a further embodiment, the fusion is no more than 100 amino acids in length. In yet another embodiment, the fusion is no more than 50 amino acids in length. A chimeric polypeptide may have at least 2 metal binding peptide domains, which domains may replace one or more domains or sequences in a larger polypeptide sequence, for instance, a naturally occurring polypeptide, or may be inserted into or at one or both ends, or any combination thereof, of a larger polypeptide sequence, e.g., a naturally occurring polypeptide.

The invention also provides isolated polyterpenoid such as carotenoid or xanthophyll binding peptides and fusions of one or more of those peptides, and optionally fusions with other peptides, such as those useful to bind to other molecules and/or a peptide that is a protease substrate, thereby forming a chimeric polypeptide. In one embodiment, the invention provides isolated carotene binding peptides and fusions of one or more of those peptides, and optionally fusions with other peptides, such as those useful to bind to other molecules and/or a peptide that is a protease substrate, thereby forming a chimeric polypeptide. In one embodiment, the polyterpenoid or carotenoid binding peptide, such as a carotene binding peptide or fusion thereof also includes a peptide sequence suitable for purification or isolation, e.g., a GST or chitin binding domain. In one embodiment, the fusion includes concatemers of carotene binding peptides, e.g., the fusion has at least two distinct carotene binding peptide sequences. In one embodiment, a linker sequence separates adjacent carotene binding peptide sequences. In one embodiment, the carotene binding peptide is at least 9 to about 30 amino acids in length, e.g., from about 10 to about 30 amino acids (or any integer in between 9 and 30) in length. Fusions of a plurality of carotene binding peptides, including fusions with the same peptide sequence or different peptide sequences, may be of any length. In one embodiment, the fusion is no more than 1000 amino acids in length. In another embodiment, the fusion is no more than 500 amino acids in length. In a further embodiment, the fusion is no more than 100 amino acids in length. In yet another embodiment, the fusion is no more than 50 amino acids in length. A chimeric polypeptide may have at least 2 carotene binding peptide domains, which domains may replace one or more domains or sequences in a larger polypeptide sequence, for instance, a naturally occurring polypeptide, or may be inserted into or at one or both ends, or any combination thereof, of a larger polypeptide sequence, e.g., a naturally occurring polypeptide.

The invention further provides isolated isoflavone binding peptides and fusions of one or more of those peptides, and optionally fusions with other peptides, such as those useful to bind to other molecules and/or a peptide that is a protease substrate, thereby forming a chimeric polypeptide. In one embodiment, the isoflavone binding peptide or fusion thereof also includes a peptide sequence suitable for purification or isolation, e.g., a GST or chitin binding domain. In one embodiment, the fusion includes concatemers of isoflavone binding peptides, e.g., the fusion has at least two distinct isoflavone binding peptide sequences. In one embodiment, a linker sequence separates adjacent isoflavone binding peptide sequences. In one embodiment, the isoflavone binding peptide is at least 10 to about 40 amino acids in length, e.g., from about 15 to about 35 amino acids (or any integer in between 10 and 40) in length. Fusions of a plurality of isoflavone binding peptides, including fusions with the same peptide sequence or different peptide sequences, may be of any length. In one embodiment, the fusion is no more than 1000 amino acids in length. In another embodiment, the fusion is no more than 500 amino acids in length. In a further embodiment, the fusion is no more than 100 amino acids in length. In yet another embodiment, the fusion is no more than 50 amino acids in length. A chimeric polypeptide may have at least 2 isoflavone binding peptide domains, which domains may replace one or more domains or sequences in a larger polypeptide sequence, e.g., a naturally occurring polypeptide, or may be inserted into or at one or both ends, or any combination thereof, of a larger polypeptide sequence, for instance, a naturally occurring polypeptide.

Also described herein are recombinant nucleic acids (expression cassettes) encoding fusion proteins with one or more peptide binding domains, where at least one is a binding peptide of the invention. In one embodiment, the peptide binding domains are expressed in concatemeric form as an artificial recombinant fusion protein (chimeric polypeptide) containing multiple copies of one or of distinct peptide binding domains. Unlike antibodies, each molecule of the chimeric polypeptide may contain multiple binding domains. Also, bacterial strains can be engineered to overexpress the concatemeric fusion protein in a manner that makes it easy to separate from the bacterial culture or extract of the bacteria. For example, the fusions are either genetically engineered for secretion into the media, or engineered to coalesce into bacterial protein bodies, e.g., inclusion bodies. In another embodiment, the fusion protein may include additional peptide domains that impart easy separation (isolation) from mixtures. Examples of such domains are those that impart differential solubility in a solvent such as alcohol, domains that cause the fusion protein to flocculate, or a second binding domain that imparts a second partner target binding ability so that the fusion protein can be isolated by binding to a substrate containing the second binding partner.

With the methods disclosed herein, it becomes economically practical to make sufficient moles of binding domains to be deployed for industrial applications such as water remediation and product/contaminant separation. Thus, the method provides for the isolation or separation of molecules from complex mixtures using a binding peptide of the invention. In one embodiment, the method provides for the separation of contaminants, such as metals including nickel, from agricultural processing of crop plants. In one embodiment, a binding peptide of the invention is employed to separate enantiomeric molecules. For example, the invention provides a method to separate enantiomers which includes providing a sample suspected of having racemic mixture of a compound; providing a substrate having immobilized thereto a peptide having a binding domain of 13 amino acids or less that preferentially binds one of the enantiomers of the compound with a dissociation constant of at least b $10^{-9}$ M or less; contacting the sample with the substrate; and washing the substrate to remove unbound material including one of the enantiomers. In one embodiment, the bound enantiomer is eluted from the substrate.

The method also provides for detection and optionally quantification of molecules in a sample, e.g., an environmental sample. For instance, a soil sample may be contacted with a sensor having a binding peptide of the invention and the presence of a metal, or the amount of a metal, in the sample detected.

Also described is a generic technique that is widely useful for genetic engineering of multiple copies of binding domains in concatemeric form. The technique includes the intentional selection of different DNA sequences to encode the same peptide domain in a manner that minimizes snap-back formation in ex vivo synthesis and recombination in vivo.

The peptides described herein all bind small molecules and were originally identified using peptide display technology, exemplified with phage display. Accordingly, a method is described of the use of a peptide display system to identify a peptide that binds a nonpeptide, non-nucleic acid target molecule having a molecular weight of less than about 1600 Da, e.g., less than about 1000 Da. The method includes obtaining a library of molecules that display peptide binding domains other than antibody molecules, selecting from the library a subset of molecules having peptide domains that bind the target molecule, and identifying the peptide sequences of the subset.

In one embodiment, the invention provides a method of isolating a target molecule from a sample. The method includes providing a peptide library comprising a plurality of peptide domains displayed on a surface of a biological particle, screening the peptide library to identify peptides that bind the target molecule and determining a nucleic acid sequence that encodes the binding peptide. In one embodiment, the method includes providing an isolated fusion protein having a target binding domain comprising at least one target binding peptide and an isolation domain comprising amino acid residues that bind a ligand, are capable of being cross-linked to a substrate or for flocculation from a solution; contacting the fusion protein with a sample containing a target molecule to bind the target molecule to the target binding domain; and isolating the fusion protein bound to the target molecule using the isolation domain, thereby isolating the target molecule. In one embodiment, the isolation domain binds to a ligand selected from the group consisting of CBD, MBD, and GST. In one embodiment, the fusion protein is isolated by immobilization on a substrate comprising the ligand. In one embodiment, the isolation domain has amino acid residues that can be cross-linked to the substrate and the isolating of the fusion protein includes cross-linking the isolation domain to the substrate before contacting the fusion protein with the sample containing the target molecule. In one embodiment the isolation domain comprises a flocculation domain and isolating the fusion protein includes flocculating the fusion protein after contacting with the sample containing the target molecule and isolating the flocculated fusion protein. Flocculation domains include but are not limited to those disclosed in Suarez et al. (*Biochim Biophys Acta* (1995) 1243:477-481), the disclosure of which is incorporated herein.

In one embodiment, the invention provides a method of detecting the presence of a target molecule of less than 1600 daltons in a sample. In one embodiment, the method includes immobilizing a peptide having a binding domain of 13 amino acids or less that binds the target molecule with a dissociation constant of at least $10^{-9}$ M or less on a substrate; contacting the immobilized peptide with the sample; washing the substrate to remove unbound material; and detecting whether the target molecule is bound to the peptide. The binding may be detected by any method, including but not limited to a surface plasmon resonance detector, a fluorescence detector, a radioisotope detector, or a spectrophotometer. In one embodiment, the binding domain comprises at least one domain within a larger fusion protein, e.g., the fusion protein is comprised of a plurality of the binding domains. In one embodiment, the target molecule is selected from the group consisting of a metal, a carotenoid, and an isoflavanoid.

Also provided is a sensing device comprising an immobilized peptide having a binding domain of 13 amino acids or less that binds a seletected target molecule with a dissociation constant of at least $10^{-9}$ M or less.

BRIEF DESCRIPTION OF THE DRAWINGS

FIG. 5 depicts an example of a nucleic acid sequence (SEQ ID NO:14) and a protein sequence (SEQ ID NO:15) for a fusion protein containing a secondary binding domain (chitin binding domain) and a concatemer of 5 metal binding domains comprised of two different metal binding peptide sequences A15 (SEQ ID NO:9) and B16 (SEQ ID NO:11).

FIG. 6 depicts a set of peptide sequences that exhibit carotene binding (SEQ ID NOs:16-48) as well as a consensus sequence therefore (SEQ ID NO:49).

FIG. 7 depicts a set of core peptide binding domains (SEQ ID NOs:50-71) from a secondary screening that impart carotene binding and have the core motif $X^1X^2GWX^3HyX^4X^5X^6$ (SEQ ID NO:72). In one embodiment, $X^2$ is alanine. In one embodiment, Hy is an aromatic amino acid, e.g., tryptophan. In one embodiment, $X^4$ is tryptophan.

FIG. 8 depicts a set of peptide sequences that exhibit binding to the isoflavone, genistein (SEQ ID NOs:73-94).

FIG. 9 depicts a set of peptide sequence having a core that imparts binding to Ni and other metals (SEQ ID NO:9, SEQ ID NO:11, SEQ ID NO:13, and SEQ ID NOs:95-111).

FIG. 10 depicts a hydropathy comparison and amino acid count of the set of peptide sequences depicted in FIG. 9.

FIGS. 12A-K show exemplary vectors (A-E) and sequences (F-K) therefore (SEQ ID NOs:55 and 143-150). (F) The vector has the following elements: nucleotides 1-303, SUMO; nucleotides 313-333, TEV protease site; nucleotides 352-486, chitin binding domain; nucleotides 523-546, PreScission protease site; nucleotides 562-786, 5× nickel binding peptide and linker (nucleotides encoding distinct peptides are shown by underlining and double underlining); and nucleotides 796-819, FLAG epitope. (G) The vector has the following elements: nucleotides 7-24, His tag; nucleotides 25-324, SUMO; nucleotides 334-354, TEV protease site; nucleotides 373-507, chitin binding domain; nucleotides 544-567, PreScission protease site; nucleotides 577-645, 2× carotene binding peptide and linker (nucleotides encoding each of the carotene peptides are shown by underlining); and nucleotides 655-678, FLAG epitope. (H-I) The vector has the following elements: nucleotides 1-1164, maltose binding protein and enterokinase site; nucleotides 1189-1252, 2× carotene binding peptide and linker (nucleotides encoding each of the carotene peptides are shown by underlining); and nucleotides 1261-1284, FLAG epitope. (J-K) The vector has the following elements: nucleotides 1-1164, maltose binding protein and enterokinase site; nucleotides 1198-1332, chitin binding domain; nucleotides 1369-1392, PreScission protease site; nucleotides 1408-

Figure 1:
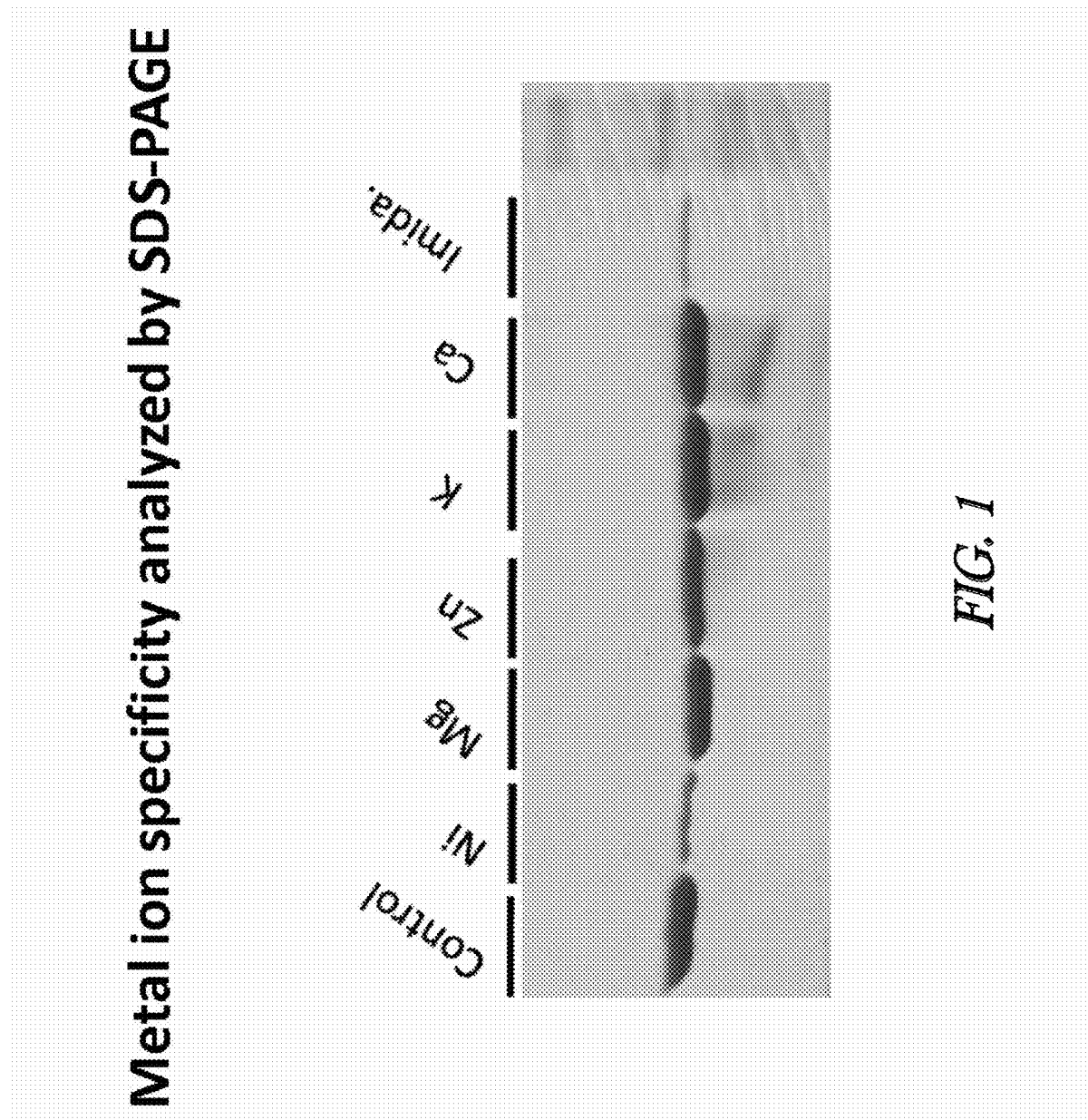
FIG. 1 shows a photograph of a gel that demonstrates the relative specificity of metal ions for a protein with a His containing peptide that ordinarily binds Ni. The lower the amount of protein eluted from the resin, the better the metal initially binds the peptide in the preincubation step.

1470, 2× carotene binding peptide and linker (nucleotides encoding each of the carotene peptides are shown by underlining); and nucleotides 1480-1503, FLAG epitope.

DETAILED DESCRIPTION

Definitions

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide (1) is not associated with proteins found in nature, (2) is free of other proteins from the same source, (3) is expressed by a cell from a different species, or (4) does not occur in nature. Thus, an isolated polypeptide is present in a form or setting that is different from that in which it is found in nature. In contrast, non-isolated polypeptides (e.g., proteins and enzymes) are found in the state they exist in nature. The terms "isolated polypeptide", "isolated peptide" or "isolated protein" include a polypeptide, peptide or protein encoded by cDNA or recombinant RNA including one of synthetic origin, or some combination thereof.

The term "gene" refers to a DNA sequence that comprises coding sequences and optionally control sequences necessary for the production of a polypeptide from the DNA sequence.

The term "wild type" as used herein, refers to a gene or gene product that has the characteristics of that gene or gene product isolated from a naturally occurring source. A wild type gene is that which is most frequently observed in a population and is thus arbitrarily designated the "wild type" form of the gene. In contrast, the term "mutant" refers to a gene or gene product that displays modifications in sequence and/or functional properties (i.e., altered characteristics) when compared to the wild type gene or gene product. It is noted that naturally-occurring mutants can be isolated; these are identified by the fact that they have altered characteristics when compared to the wild type gene or gene product.

The term "recombinant DNA molecule" means a hybrid DNA sequence comprising at least two nucleotide sequences not normally found together in nature. The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The terms "recombinant vector", "expression vector" or "construct" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenylation signal and optionally an enhancer sequence.

A polynucleotide having a nucleotide sequence "encoding a peptide, protein or polypeptide" means a nucleic acid sequence comprising a coding region for the peptide, protein or polypeptide. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

The term "transcription regulatory element" or "transcription regulatory sequence" refers to a genetic element or sequence that controls some aspect of the expression of nucleic acid sequence(s). For example, a promoter is a regulatory element that facilitates the initiation of transcription of an operably linked coding region. Other regulatory elements include, but are not limited to, transcription factor binding sites, splicing signals, polyadenylation signals, termination signals and enhancer elements, and include elements which increase or decrease transcription of linked sequences, e.g., in the presence of trans-acting elements.

Promoters and enhancers consist of short arrays of DNA sequences that interact specifically with cellular proteins involved in transcription. Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site. A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and poly adenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene.

The term "expression system" refers to any assay or system for determining (e.g., detecting) the expression of a gene of interest. Those skilled in the field of molecular biology will understand that any of a wide variety of expression systems may be used.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

The terms "cell," "cell line," "host cell," as used herein, are used interchangeably, and all such designations include progeny or potential progeny of these designations. By "transformed cell" is meant a cell into which (or into an ancestor of which) has been introduced a nucleic acid molecule of the invention. Optionally, a nucleic acid molecule of the invention may be introduced into a suitable cell line so as to create a stably transfected cell line capable of producing the protein or polypeptide encoded by the nucleic acid molecule. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide, or a precursor thereof, e.g., the pre- or prepro- form of the protein or polypeptide, is produced.

A peptide "linker" may include 2 or more amino acid residues, e.g., up to about 50 amino acid residues, or any integer between 2 and 50, which linker sequence may include protease recognition sites. Peptide linkers do not substantially alter the binding properties of adjacent (linked) binding peptides.

Exemplary Embodiments

The peptide sequences shown in FIGS. 6-9, some of which bind to carotene, some to genistein and some to metals, are diverse. The carotene binding peptides may be useful for removing carotene and structurally similar molecules from food processing streams, notably exemplified by palm oil processing streams which tend to have higher carotene content than other vegetable oils, as well as to purify carotene. Genistein is an isoflavone typically isolated from soybean processing streams, and is useful as a natural nutraceutical product, e.g., for the treatment of menopausal symptoms. Thus, the genistein binding peptides are useful for the isolation of genistein and structurally similar isoflavones, e.g., from soybeans. Nickel is a common metal that occurs in all agricultural products, but which can become concentrated above natural levels in the water streams used in industrial settings where agricultural products like corn are processed into food stuffs in large quantities. The nickel binding peptides disclosed herein are useful for removing nickel (or other metals) from such water streams. Those peptides are also useful for purifying fusion proteins expressed in microorganisms by binding the fusion protein to a nickel containing resin.

Despite the diverse structure of the above three targets and the diverse uses of the peptides, each of the peptides described herein was identified by a common methodology that can be applied to identifying other peptides that bind to distinct small molecules of industrial significance. As used herein, a "small molecule of industrial significance" means a non-peptide, non-nucleic acid molecule or atoms or ions, typically having a molecular weight of 1000 Da or less that is produced by, or can be extracted from, processing streams used to make a product.

The common methodology is to select a target of interest, such as a small molecule of industrial significance, obtain a peptide display library such as phage display libraries that display random peptide sequences on the surface of a M13 phage particle, screen or "pan" the library to identify a population of phage particles that bind the target of interest, amplify and isolate clones of the particles that bind, then sequence the phage DNA encoding the peptide libraries to determine the peptide sequence(s) that bind the target of interest. Optionally, the peptides can be further characterized by any number of performance criteria applicable to the target and purpose of interest.

Different methods of panning will be applicable to different types of target molecules. In the present examples, the common methodology for panning was to immobilize the target molecule to a substrate, contact the immobilized target with the phage library, wash away phage particles that do not bind, elute the particles that do bind using a detergent or other protein denaturing agent, amplifying the particles by infecting the host bacterium to get a selected population and repeating the same panning process on the selected population one or more times, optionally using more stringent conditions in subsequent pans if it is desirable to select stronger binding peptides. In a typical practice such as for identifying the metal binding peptides, four rounds of panning were used. Ultimately individual plaques or colonies from panned populations were selected and the phage DNA was sequenced.

Once the DNA is sequenced, the peptide binding domain can be expressed as a fusion protein which is selected to have one or more properties suitable for an intended use or for further characterization of the target binding properties. In the present case, it was useful to fuse the binding domains to a polypeptide that binds a different ligand so that the target binding domain can be immobilized on a substrate linked to the ligand that binds to the fused polypeptide. There are numerous ligand-polypeptide binding pairs known in the art to be useful for making such fusion proteins without altering the property of ligand binding. Strepatavidin has probably most often been used because of its tight binding to biotin, however, strepavidin needs to form into a tetramer for optimal binding. In one example, glutathione S-transferase (GST) was selected as another common fusion protein because of its ability to bind glutathione and high solubility in the cytosol, allowing for high expression in cells. In another example explained in more detail hereafter, the chitin binding domain (CBD) of chitinase A1 from *Bacillus circulans* is used to make a fusion protein because of its relatively small size (45 residues) and ease of immobilizing chitin to a substrate. Kits for making fusions, such as GST or CBD fusions, and columns to which those fusions bind, are known to the art.

Phage library and panning. The phage library, a random 21-amino acid peptide library with a diversity of about 1×10⁹, was constructed in the laboratory of Dr. Rao in the Dept. of Biochemistry, Biophysics & Molecular Biology at Iowa State University. Nickel was immobilized on NTA-Sepharose (IMAC Sepharose, GE-Health Care) as described by the manufacturer. 20 µL Ni-NTA-Sepharose placed in 1.5 mL polypropylene micro centrifuge tubes was blocked by 1.0 mL phosphate buffered saline (PBS)+2% bovine serum albumin (BSA) for 3 hours at room temperature to reduce non specific binding. The matrix was then incubated with the 21 amino acid linear phage pIII peptide library in PBS (+0.2% BSA+0.05% Tween 20) for 3 hours at room temperature. The negative control was NTA-Sepharose that was not charged with nickel. Typical phage panning includes 3 steps—binding, washing and amplification. After incubation of the target with the library, unbound phage were removed by washing with PBS containing 0-0.15% Tween 20 and bound phage eluted with 100 mM HCl. Eluted phage were immediately neutralized by 1 M Tris/HCl pH 8.0. Completely neutralized phage were used to infect host E. coli strain XL1-Blue. Amplified phage were used for the next round phage panning. Phage panning was repeated 4 times after which a number of colonies were selected to produce phage particles to detect specific binders by an ELISA method.

Specifically, phage were incubated with the immobilized target and bound phage detected by anti-M13 phage antibody HRP conjugate. The corresponding phagemids were then sequenced to identify the nature of the peptide sequence. Table 1 shows exemplary sequences from the fourth round of screening.

TABLE 1

Sequences of clones selected after 4th round with primary library

| % in seq. | Displayed sequence (21 random amino acid part) | motif |
|---|---|---|
| (A) 40% | E H G Q L F V S H V S S S R G *H V H* A P M (SEQ ID NO: 113) | HxH |
| (B) 36% | Y *H Y H* P G G V W P M R R P A P P L T T G (SEQ ID NO: 114) | HxH |
| (C) 13% | T H S V Q Y F R L C Q L Q H T K V R H Y W (SEQ ID NO: 115) | none |

Two sequences were in the majority after the 4th round (see above) and both had a HxH motif in the displayed sequence. Two 13-residue secondary phage-peptide libraries that contained the "HxH" motif in different sections of the peptide sequence, e.g., towards the N-terminus (where the two histidines are separated by one amino acid residue and there are two amino acids flanking the N-terminal histidine and eight amino acids flanking the other histidine) and in the center (where the two histidines are separated by one amino acid residue and there are five amino acids flanking each of the histidine residues), were constructed and the panning experiments performed again. After the fourth round of screening, a total of 60 strong binding sequences were identified. Nineteen of these were selected for further experiments and the 13 residue sequences thereof are shown in FIG. 9.

Amongst the selected sequences only one, C26 (SEQ ID NO:13), displayed the six residue polyhistidine sequence well known in the art to bind nickel and commonly used for making his-tagged proteins for purification. This binding motif had a Kd of about 2.3×10⁻¹¹ M. Surprisingly however, numerous other histidine peptides were discovered with even stronger binding (lower Kd) than the six residue polyhistidine motif or other histidine containing nickel binding motifs such as (HQ)₆ (SEQ ID NO:2) While the sequences appear to be dissimilar, all sequences having a lower Kd than the polyhistidine sequences can generically be described as having a core with the structure

H—X—H—(Z')—H—(Z")—H          (SEQ ID NO:116)

where H is histidine, X is a single amino acid selected from the group consisting of arginine, valine, phenylalanine, asparagine, tyrosine, lysine, alanine, glycine, threonine, and isoleucine; Z' is one or two amino acids, at least one selected from the group consisting of glutamine, arginine, valine, methionine, leucine, phenylalanine, alanine, glycine, isoleucine, threonine, tryptophan, tyrosine or histidine; and Z" is one to four amino acids, at least one selected from the group consisting of arginine, valine, phenylalanine, alanine, glycine, isoleucine, threonine, tryptophan or histidine. In one embodiment, X is arginine, valine, asparagine, alanine, glycine, or isoleucine. In one embodiment, X is arginine, valine, phenylalanine, alanine, glycine, threonine or isoleucine. In one embodiment, Z' is two amino acids selected from the group consisting of arginine, glutamine, methionine, phenylalanine, glycine, leucine, tryptophan, or histidine. In one embodiment, Z' is one amino acid selected from the group consisting of glycine, threonine, or tryptophan. In one embodiment, Z' is one or two amino acids, at least one selected from the group consisting of arginine, valine, phenylalanine, alanine, glycine, isoleucine, threonine, tryptophan, tyrosine or histidine. In one embodiment, Z" is one amino acid selected from alanine, arginine, threonine or leucine. In one embodiment, Z" is two to four amino acids, at least one selected from the group consisting of aspartic acid, alanine, lysine, leucine, threonine, or histidine. In one embodiment, metal binding peptides have at least 10 amino acid residues which may include the core sequence described above, e.g., SEQ ID NO: 116, where Z' is one amino acid and Z" is four amino acids or where Z' is two amino acids and Z" is three amino acids. In addition, unlike the other nickel binding histidine containing peptides known in the art, the above-described peptides have no more than 5 histidine residues in the core sequence. Further, these sequences bind the nickel with a dissociation constant of at least about 9.5×10⁻¹¹ M or less, e.g., about 5×10⁻¹² M or less, for instance, about 5×10⁻¹³ M or less.

Other similarities that define certain particular embodiments of these tight binding sequences are as follows: Unlike the (HQ)₆ (SEQ ID NO:6) sequence, the portion of the sequence defined as Z" above does not contain glutamine. In some embodiment, within a larger peptide sequence of at least 12 amino acids inclusive of the core sequence, at least one proline appears outside of the core sequence. In fact, upon analyzing the overall occurrence of each amino acid in all the metal binding sequences as shown by the hydropathy analysis in FIG. 10, it was noted that proline, which is a relatively rare amino acid in a typical natural protein sequence occurs in 59% of the sequences in FIG. 9 and in 70% of the sequences having a dissociation constant of at least about 9.5×10⁻¹¹ M or less.

It was also noted that aside from histidine, these metal binding sequences that had a dissociation constant of at least about 9.5×10⁻¹¹ M or less tended to have few charged amino acids. For example, within a larger peptide sequence of at least 12 amino acids inclusive of the core sequence it is often the case that no more than 2 amino acid residues selected from the group of aspartate (D) and glutamate (E) appear. Also, within a larger peptide sequence of at least 12 amino acids inclusive of the core sequence, in some embodiments, no more than 2 amino acid residues selected from the group of lysine (K) and arginine (R) appear, although arginine itself appears once or twice in almost all the sequences. It is also often the case that within a larger peptide sequence of at least 12 amino acids inclusive of the core sequence contains no more than 4 amino acid residues selected from the group of aspartate (D), glutamate (E), lysine (K) and arginine (R).

Conversely it was also noted that the metal binding peptides contained aromatic amino acids. Thus, in some embodiments, within a larger peptide sequence of at least 12 amino acids inclusive of the core sequence at least one amino acid selected from the group consisting of phenylalanine (F), tyrosine (Y) and tryptophan (W) appears.

Another description common to some, but not all embodiments can be described as a metal binding peptide having a core amino acid sequence of the formula

H—X—H—X—H—X—H (SEQ ID NO:117)

where H is histidine, each X is independently any single amino selected from the group consisting of arginine, valine, phenylalanine, alanine, glycine, threonine, and isoleucine; where the peptide binds the metal with a dissociation constant of at least about $2.0 \times 10^{-12}$ M or less.

Another description common for some, but not all embodiments can be described as a metal binding peptide having a core amino acid sequence of the formula

Z—H—H—H (SEQ ID NO:118)

where H is histidine, Z is a sequence of 3 to 5 amino acids, at least one being selected from the group consisting of arginine, phenylalanine, proline, alanine, glycine and histidine, with the proviso that no more than 5 histidine residues occur within a larger peptide sequence of at least 12 amino acids inclusive of the core sequence; and the peptide binds the metal with a dissociation constant of at least about $2.0 \times 10^{-12}$ M or less In one embodiment, the invention provides a peptide having a core amino acid sequence of the formula H—X—H—(Z')—H—(Z")—H (SEQ ID NO:116), where H is histidine, X is a single amino acid selected from the group consisting of arginine, valine, phenylalanine, alanine, glycine, threonine, and isoleucine; Z' is one or two amino acids, at least one selected from the group consisting of arginine, valine, phenylalanine, alanine, glycine, isoleucine, threonine, tryptophan, tyrosine or histidine; Z" is 1 to 4 amino acids, at least one selected from the group consisting of arginine, valine, phenylalanine, alanine, glycine, methionine, leucine, isoleucine, threonine, tryptophan or histidine, wherein no more than 5 histidine residues occur in the core sequence of SEQ ID NO:116. In one embodiment, the peptide binds a metal with a dissociation constant of at least about $9.0 \times 10^{-11}$ M or less. In one embodiment, Z" does not contain glutamine. In one embodiment, the invention provides a peptide having a core amino acid sequence of the formula H—X—H—X—H—X—H (SEQ ID NO:117), where H is histidine, each X is independently any single amino selected from the group consisting of arginine, valine, phenylalanine, alanine, glycine, threonine, and isoleucine. In one embodiment, the peptide binds a metal with a dissociation constant of at least about $2.0 \times 10^{-12}$ M or less. In one embodiment, the invention provides a peptide having a core amino acid sequence of the formula Z—H—H—H (SEQ ID NO:118) where H is histidine, Z is a sequence of 3 to 5 amino acids, at least one being selected from the group consisting of arginine, phenylalanine, proline, alanine, glycine and histidine, with the proviso that no more than 5 histidine residues occur within a larger peptide sequence of at least 12 amino acids inclusive of the core sequence.

In one embodiment, a fusion polypeptide has (SEQ ID NO:116)$_n$, (SEQ ID NO:117)$_n$, or (SEQ ID NO:118)$_n$, or a combination thereof, where each n is independently 0 to 50 with the proviso that at least one of SEQ ID NOs:116-118 is present in the fusion. In one embodiment, the peptide binds a metal with a dissociation constant of at least about $2.0 \times 10^{-12}$ M or less. In one embodiment, the peptide of any of SEQ ID NOs:116-118 binds a metal selected from the group consisting of nickel, zinc and copper and binds at least one of the selected metals with a dissociation constant of at least about $1.0 \times 10^{-11}$ or less.

The invention also provides an isolated carotene binding peptide comprising a consensus sequence of the formula $X^1X^2GWX^3HyX^4X^5X^6$ (SEQ ID NO:120) where each X is any amino acid and Hy is an aromatic amino acid. In one embodiment, $X^1$ is selected from the group consisting of valine, tryptophan, leucine, glutamine, serine, tyrosine, threonine, isoleucine, alanine, or phenylalanine. In one embodiment, $X^2$ is alanine, glycine, isoleucine or valine. In one embodiment, Hy is tryptophan. In one embodiment, $X^4$ is a tryptophan. In one embodiment, Hy and $X^4$ are each tryptophan. In one embodiment, $X^2$ is alanine and Hy is tryptophan. In one embodiment, $X^2$ is alanine and $X^4$ is tryptophan. In one embodiment, $X^2$ is alanine and each of Hy and $X^4$ is tryptophan. $X^1$ may be a single amino acid selected from alanine, valine, leucine, glutamine, tryptophan, tyrosine, serine, proline, threonine or isoleucine. $X^3$ may be a single amino acid selected from tryptophan, methionine, glycine, proline, leucine, or serine. $X^4$ may be tryptophan, phenylalanine, methionine, glycine, threonine, or histidine. $X^5$ may be glycine, tryptophan, serine, phenylalanine, leucine, glutamine, or alanine. $X^6$ may be threonine, glycine, tryptophan, alanine, methionine, asparagine, or valine.

Further provided is an isolated carotene binding peptide comprising a tetra peptide of the sequence

$X^1WX^2Hy$ (SEQ ID NO:121)

where $X^1$ is selected from the group consisting of glycine, proline and leucine, $X^2$ is any amino acid and Hy is an aromatic amino acid.

Further provided is a peptide domain that binds genistein comprising the sequence:

L—X—L or L—X—X—X—L (SEQ ID NO:122)

where L is leucine and X is any amino acid. In one embodiment, for L—X—L, X is glycine, leucine or serine. In one embodiment, for L—X—X—X—L (SEQ ID NO:122), each X is independently leucine, histidine, glycine, phenylalanine, serine, lysine, aspartate, glutamate or alanine. In one embodiment, the genistein binding domain has

SLGLWHSQRHFDVHREHSRHQT (SEQ ID NO:123).

Further provided are chimeric polypeptides having at least one of SEQ ID NOs:9, 11, 16-48, 50-71, or 73-110, or a variant thereof with one to three amino acid substitutions, or up to 10% of the residues substituted, which variant has the binding properties of SEQ ID NOs:9, 11, 16-48, 50-71, or 73-110.

Also provided is a recombinant nucleic acid encoding a concatemeric repeat of N identical peptide domains of at least 6 amino acids in length within a single polypeptide, wherein N is at least 5, and no more than two of the identical peptides are encoded by the same nucleic acid sequence. In one embodiment, no sequence of 9 contiguous nucleotides is identical between any two sequences encoding an identical binding domain. In one embodiment, there is less identity between two sequences encoding identical peptide domains located distally from one another than to any two sequences encoding the same identical domains located more proximally to one another by comparison.

Also provided is a method of using a peptide display system to identify a peptide that binds a non peptide non nucleic acid target molecule having a molecular weight of less than 1000 Da. The method includes obtaining a non peptide non nucleic acid target molecule having a molecular weight of less than 1000 Da; obtaining a library of molecules that display peptide binding domains other than antibody molecules; selecting from the library, a subset of molecules having peptide domains that bind the target molecule, and identifying the peptide sequence of the selected subset of molecules.

Computational analysis of Nickel-binding peptides. Because of the relatively high number of hydrophobic or neutral residues and relative low number of hydrophilic residues, the peptides were analyzed with regard to their amino acid composition and hydrophobicity using the ExPASy proteomics server at the Swiss Institute of Bioinformatics (http://ca.expasy.org/tools/protparam.html) with the results depicted in FIG. 10. It was noted that in addition to histidine, the amino acids arginine (94%), glycine (82%), alanine (65%) and proline (59%) are present in >50% of the peptides. It was also noted that within a larger peptide sequence of 13 amino acids inclusive of the core, the residues cysteine and generally glutamine are absent and asparagine, glutamate, lysine and methionine are rarely represented. The preferred basic amino acid is almost exclusively arginine. There does not appear to be any correlation between hydrophobicity and binding affinity as measured by the GRAVY value. The most hydrophobic peptide is A12 (GRAVY=–0.215) and the least hydrophobic peptide is B17 (GRAVY=–2.215). The GRAVY value for a peptide or protein is calculated as the sum of hydropathy values of all the amino acids, divided by the number of residues in the sequence. This result is skewed, however, because histidine is a hydrophilic amino acid and appears at least 4 times in every sequence of at least 13 amino acids that binds with Kd of $1.3 \times 10^{-8}$ M or lower. If histidine were eliminated from the hydropathy calculation, the remaining amino acids would typically confer a more hydrophobic character than the GRAVY values show for the entire sequences inclusive of histidine.

Recombinant protein expression and vectors or expression. As mentioned above, some of the peptides were expressed in *E. coli* as a GST-fused protein using a pGEX vector from Amersham and purified by affinity chromatography on a glutathione agarose matrix. These fusion proteins were used to further characterize the metal binding properties of the peptides B16 and A15 in comparison to C26, which was considered an appropriate comparative control because a polyhistidine 6 mer was already known to have strong nickel binding properties.

pGEX vector, pGEX 4T-1 (GE Healthcare), for expression of GST fused proteins, was modified to introduce a Sfi I restriction site. The new vector is designated as pGEX-BS and permits cloning of Sfi-NotI cut fragments from clones obtained through phage-peptide library screening. The relevant base vector sequence and specific fusion sequences are shown below:

```
                                              (SEQ ID NO: 124)
ATCGGATCTGGTTCCGCGTGGATCCCGGGCCCAGCCGGCC

CTGCAGGGATCCCCGGAATTCCCGGGTCG ACTCGAGCGGCCGC

ATCGTGACTGACTGACG---pGEX-4T1 (3')
```

Cloning Ni-binding peptide motifs into pGEX-BS vector (nucleotide sequence in italics)

```
pGEX-A8
(Ni-binding motif-IGGWSHHHLGRTA; SEQ ID NO: 96)
                                              (SEQ ID NO: 125)
5'gst-ATCGGATCTGGTTCCGCGTGGATCCCGGGCCCAGCCGGCC

ATTGTGGTTGGTCTCATCATCATCTTGGTAGGACGGCT

GCGGCCGCATCGTGACTGACTGACG-3' pGEX-A10
(Ni-binding motif-HYHYMHRHSGSSP; SEQ ID NO: 103)
                                              (SEQ ID NO: 126)
5'gst-ATCGGATCTGGTTCCGCGTGGATCCCGGGCCCAGCCGGCC

CATTATCATTATGCATCGTCATTCGGGTTCTAGTCCG

GCGGCCGCATCGTGACTGACTGACG-3' pGEX-A12
(Ni-binding motif-IGHLMHGHRSSVT; SEQ ID NO: 106)
                                              (SEQ ID NO: 127)
5'gst-ATCGGATCTGGTTCCGCGTGGATCCCGGGCCCAGCCGGCC

ATTGGGCATCTGATGCATGGTCATCGTAGTTCTGTTACG

GCGGCCGCATCGTGACTGACTGACG-3' pGEX-A15
(Ni-binding motif-YTRTPHVHWHAHG; SEQ ID NO: 9)
                                              (SEQ ID NO: 128)
5'gst-ATCGGATCTGGTTCCGCGTGGATCCCGGGCCCAGCCGGCC

TATACGAGGACGCCTCATGTGCATTGGCATGCGCATGGT

GCGGCCGCATCGTGACTGACTGACG-3' pGEX-A18
(Ni-binding motif-PHPFRHHHGLRAP; SEQ ID NO: 98)
                                              (SEQ ID NO: 129)
5'gst-ATCGGATCTGGTTCCGCGTGGATCCCGGGCCCAGCCGGCC

CCTCATCCGTTTAGGCATCATCATGGTCTGAGGGCGCCG

GCGGCCGCATCGTGACTGACTGACG-3' pGEX-B4
(Ni-binding motif-HAAGHHHHGWWRP; SEQ ID NO: 99)
                                              (SEQ ID NO: 130)
5'gst-ATCGGATCTGGTTCCGCGTGGATCCCGGGCCCAGCCGGCC

CATGCTGCTGGTCATCATCATCATGGGTGGTGGAGGCCT

GCGGCCGCATCGTGACTGACTGACG-3' pGEX-B6
(Ni-binding motif-LAYRWHHHHWGPA; SEQ ID NO: 107)
                                              (SEQ ID NO: 131)
5'gst-ATCGGATCTGGTTCCGCGTGGATCCCGGGCCCAGCCGGCC

CTTGCTTATAGGTGGCATCATCATCATTGGGGGCCGGCT

GCGGCCGCATCGTGACTGACTGACG-3'
``` pGEX-B16
(Ni-binding motif-WGGWRHVHGHRHP; SEQ ID NO: 11)
(SEQ ID NO: 132)
5'gst-ATCGGATCTGGTTCCGCGTGGATCCC*GGCCCAGCCGGCC*

CTGGGGTGGTTGGCGTCATGTTCATGGTCATCGTCATCCT

*GCGGCCGC*ATCGTGACTGACTGACG-3' pGEX-B17
(Ni-binding motif-HGHWRHTHTGDRG; SEQ ID NO: 102)
(SEQ ID NO: 133)
5'gst-ATCGGATCTGGTTCCGCGTGGATCCC*GGCCCAGCCGGCC*

CCATGGGCATTGGAGGCATACGCATACGGGGGATAGGGGG

*GCGGCCGC*ATCGTGACTGACTGACG-3' pGEX-C10
(Ni-binding motif-EWHRHHRHPEVLA; SEQ ID NO: 97)
(SEQ ID NO: 134)
5'gst-ATCGGATCTGGTTCCGCGTGGATCCC*GGCCCAGCCGGCC*

GAGTGGCATAGGCATCATCGGCATCCGGAGGTGTTGGCG

*GCGGCCGC*ATCGTGACTGACTGACG-3' pGEX-C11
(Ni-binding motif-WGGGKHHHHRGPG; SEQ ID NO: 100)
(SEQ ID NO: 135)
5'gst-ATCGGATCTGGTTCCGCGTGGATCCC*GGCCCAGCCGGCC*

TGGGGGGGGGGGAAGCATCATCATCATCGGGGGCCGGGG

*GCGGCCGC*ATCGTGACTGACTGACG-3' pGEX-C22
(Ni-binding motif-HNHGLHLHGGERG; SEQ ID NO: 105)
(SEQ ID NO: 136)
5'gst-ATCGGATCTGGTTCCGCGTGGATCCC*GGCCCAGCCGGCC*

CATAATCATGGGCTTCATTTGCATGGGGGGAGCGGGGG

*GCGGCCGC*ATCGTGACTGACTGACG-3' pGEX-C26 (Ni-binding motif-YSHHHHHHLAGTA for
6xHis control; SEQ ID NO: 13)
(SEQ ID NO: 137)
5'gst-ATCGGATCTGGTTCCGCGTGGATCCC*GGCCCAGCCGGCC*

TATTCTCATCATCATCATCATCATTTGGCTGGTACGGCG

*GCGGCCGC*ATCGTGACTGACTGACG-3' pGEX-C28
(Ni-binding motif-IRHIHGHDKLTHA; SEQ ID NO: 101)
(SEQ ID NO: 138)
5'gst-ATCGGATCTGGTTCCGCGTGGATCCC*GGCCCAGCCGGCC*

ATTAGGCATATTCATGGTCATGATAAGCTGACGCATGCT

*GCGGCCGC*ATCGTGACTGACTGACG-3' pGEX-C29
(Ni-binding motif-IPHRHQFHHTAHA; SEQ ID NO: 95)
(SEQ ID NO: 139)
5'gst-ATCGGATCTGGTTCCGCGTGGATCCC*GGCCCAGCCGGCC*

ATTCCTCATCGTCATCAGTTTCATCATACGGCTCATGCG

*GCGGCCGC*ATCGTGACTGACTGACG-3' pGEX-C31
(Ni-binding motif-PHHVTHTGARGGG; SEQ ID NO: 104)
(SEQ ID NO: 140)
5'gst-ATCGGATCTGGTTCCGCGTGGATCCC*GGCCCAGCCGGCC*

CCTCATCATGTGCATACGCATGGTGCGCGTGGGGGGGGG

*GCGGCCGC*ATCGTGACTGACTGACG-3' pGEX-C46
(Ni-binding motif-LAIVRHSHSLGIG; SEQ ID NO: 108)
(SEQ ID NO: 141)
5'gst-ATCGGATCTGGTTCCGCGTGGATCCC*GGCCCAGCCGGCC*

CTTGCTATTGTTCGTCATTCGCATTCTCTTGGTATTGGG

*GCGGCCGC*ATCGTGACTGACTGAC-3'

General Protocols for Fused/Tagged Protein Expression/Purification

Materials

LB medium (10 g Trypton, 5 g Yeast extract, 10 g NaCl, 1 L distilled $H_2O$).

1×HBS buffer pH 7.4 (10 mM HEPES, 150 mM NaCl, 0.001% Triton X-100).

1000× Kanamicin (Km) stock (20 mg Km in 1 mL pure $H_2O$).

1000× Ampicillin (Amp) stock (50 mg Amp in 1 mL pure H2O).

Host *E. coli* competent cell—Rosetta2 (DE3)pLysS (Novagen), BL21(DE3)pLys S (Stratagene), 2-4 L baffled flask or several small size baffled flasks, 10-20 mL disposable open column. Chitin Beads (NEB), 1 or 5 mL Ni-NTA super flow FPLC column (Qiagen), Glutathione sepharose 4B (GE health care), Amylose resin (NEB).

*E. coli* Host Cell:

BL21(DE3)pLysS cell for GST fusion protein overexpression.

Rosetta2(DE3)pLysS cell for SUMO, Maltose binding protein (MBP) and Chitin Binding Domain (CBD) fusion protein overexpression.

Transformation was performed by chemical transformation.

Overexpression and Purification Protocol

1. Transfer individual transformed colonies into about 15 mL culture tubes containing 3 mL LB-Km (final concenration 20 μg/mL) or LB-Amp (Final concentration 50 μg/mL). And incubate overnight (8-12 hours) at 37° C. with shaking.

2. Transfer 1 mL over night culture into 1 L LB-Km (in 2-4 L baffled flask) then incubate with vigorous agitation at 37° C. until $OD_{600}$=about 0.4.

3. Change temperature to 20 or 25° C. then incubate 30 minutes with vigorous agitation.

4. Add IPTG at final concentration of 0.5 mM, then continue to incubate, overnight (10 to about 15 hours) with vigorous agitation.

5. Centrifuge cell culture for harvesting (3000-5000×g, 15 minutes, at 4° C.).

6. Re-suspend pellet using 40-50 mL of cold 1×HBS pH 7.4 buffer (after this step, skeep on ice).

7. Lyse the cells using ultra sonic cell disruptor (output power about 25W, 10 seconds on then 50 seconds off, keep on ice (+water) bath, repeat 10-20 times for a total of 100-200 seconds) without frothing.

8. Centrifuge disrupted cells (12000-20000×g, 20 minutes, at 2° C.).

Then transfer supernatant into new tube.

(A) Purification with Ni-NTA Column (for 6xHis Tagged Protein, 6xHis-SUMO etc.)

9. Equilibrate Ni-NTA FPLC column by 5 CV 1×HBS.

10. Load the supernatant (from step 8) on column.

11. Wash out nonspecific protein from resin using 10 CV 1×HBS with 45 mM imidazole (pH 7.4) (CV=Column Volume)

12. Elute protein HBS with 30-300 mM imidazole gradient in 10 CV.
13. Run SDS PAGE for fractions.
(B) Purification with GSH Column (for GST Fused Ni Binding Protein)
9. Equilibrate 1 or 5 mL GST sepharose 4B column by 5 CV 1×HBS(pH7.4).
10. Load the supernatant (from step 8) on column.
11. Wash out nonspecific protein from resin using 15 CV 1×HBS.
12. Elute protein using 1-2 CV of HBS with 20 mM reduced glutathione (pH 7.4-8.0).
13. Run SDS PAGE.
(C) Purification with Amylose Resin (for MBP Fused Beta-carotene Binding Protein)
9. Equilibrate 1 or 5 mL amylose resin with 5× column volume of 1×HBS (pH 7.4).
10. Load the supernatant (from step 8) on column.
11. Wash out nonspecific protein from resin using 15 CV 1×HBS.
12. Elute protein using 1-2 CV of HBS with 20 mM maltose (pH 7.4).
13. Run SDS PAGE.
(D) Purification with Chitin Beads (for SUMO-CBD-Ni and 2× B-carotene Binding Motif etc)
9. Load about 3 mL chitin beads (NEB) in an about 15 mL column and then equilibrate the resin with 9 mL 1×HBS.
10. Load the supernatant (from step 8) on column (at 4° C.)
11. Wash out unbound protein from resin using 18 mL (3 times×6 mL) cold 1×HBS buffer.
12. Take 20 µL resin and mix with 20 µL SDS sample buffer then heat for 5 minutes at 100° C.
13. Run SDS-PAGE.

Precision protease can digest protein between chitin binding domain and target protein.

pE-SUMO *E. coli* over-expression vector (Life Sensors, Inc) was used for the over-expression. Small Ubiquitin-like Modifier (SUMO) is a protein of about 100 amino acids that has been demonstrated to enhance the solubility of proteins when used as a fusion partner for the recombinant expression of proteins (Marblestone et al., *Protein Science* (2006) 15:182-189). The vector has a 6×His tag located at the N-terminal of the SUMO (Smt3, Yeast) for protein purification. A synthetic gene optimized for *E. coli* expression and encoding the chitin binding domain (CBD) from Chitinase A1 (*Bacillus circulans*), a protease cleavage site, two copies of the β-carotene-binding peptide (QAGWGWWWG; SEQ ID NO:55) and the FLAG tag was synthesized by Integrated DNA Technologies, Inc. (Coralville, Iowa). The synthesized DNA was cloned into BsaI restriction enzyme site of pE-SUMO vector and transformed into *E. coli* Rosetta2 (DE3) pLysS cells (Novagen, Inc.). Cells were then incubated with vigorous shaking for 3 hours at 30° C. in LB media after induction with 0.5 mM Isopropyl β-D-1-thiogalactopyranoside (IPTG). Subsequently, cells were re-suspended in 1× Phosphate buffered saline (PBS) with 0.05% Triton X-100 and homogenized by ultrasonic cell disrupter. Soluble fraction containing about 50% of the over-expressed protein was separated by centrifugation (14000×g, 20 minutes) and then purified by passing over chitin beads (New England Bio Labs, Inc.). The yield of purified soluble SUMO-CBD-β-carotene binding protein was ~10 mg/ml as measured by Bio-Rad Protein Assay (BIO-RAD Laboratories, Inc.). (See attached PowerPoint file).

Binding strength measured by surface plasmon resonance (SPR). Affinity experiments were performed on a BIACOR 3000 system using a Sensor Chip NTA. The dissociation and association rate constants and the corresponding Kd values for each peptide is shown in FIG. 9.

Binding to other metal ions. Binding to ions such as Zn, Cu, Mg, Ca, Mg and K was measured by two methods. The first used SDS-PAGE to detect bound ability of the proteins to adhere to a nickel resin after being first contacted by a metal ion. About 50 µL of each GST-fused peptide (10 µg/µL) in PBS containing 100 mM of the specific metal ion was incubated with 20 µl of Ni-NTA resin for 2 hours at 4° C. The sample was centrifuged and washed to remove unbound protein. SDS-sample buffer was added to the resin, boiled and analyzed by SDS-PAGE. A representative gel is shown in FIG. 1. Similar results were obtained with all 19 peptides. Peptides incubated in buffer containing Ni showed much less binding to Ni-NTA (as would be expected). Since other metal ions do not bind to the peptides as well as nickel, they preferentially bound to Ni-NTA agarose and were eluted in SDS sample buffer.

Figure 2:
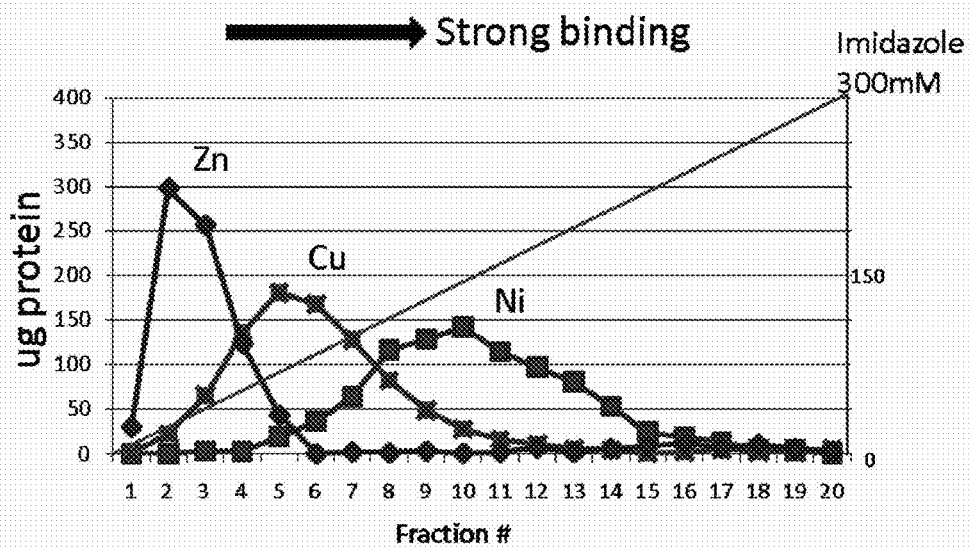
FIG. 2 illustrates relative binding of the metals Ni, Cu and Zn to a fusion protein containing a metal binding His containing peptide according to the present disclosure (GST-A15; A15, YTRTPHVHWHAHG, SEQ ID NO:9). Depicted is a profile of imidazole elution of metals bound to protein immobilized to a column via GST.
Figure 3:
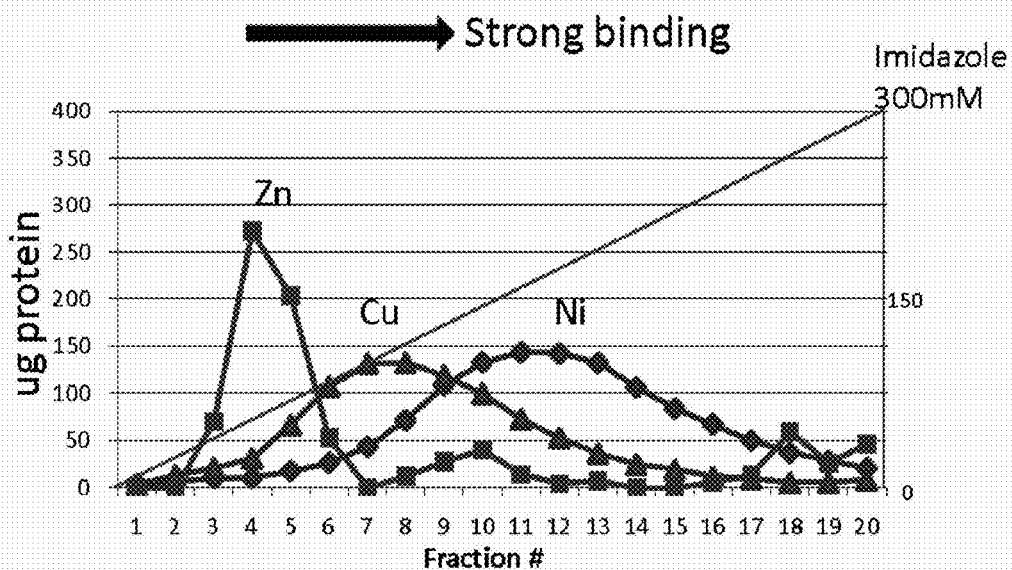
FIG. 3 illustrates relative binding of the metals Ni, Cu and Zn to a fusion protein containing a metal binding His containing peptide according to the present disclosure (GST-B16; B16, WGGWRHVHGHRHP, SEQ ID NO:11).
Figure 4:
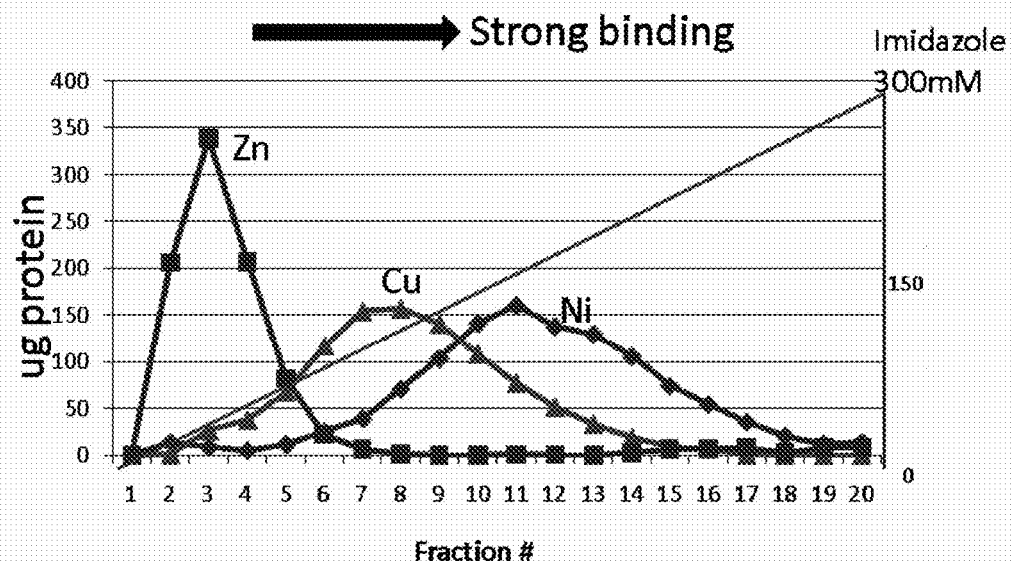
FIG. 4 illustrates relative binding of the metals Ni, Cu and Zn to a fusion protein containing a metal binding $His_6$ peptide (GST-C26; C26, YEHHHHHHLAGTA, SEQ ID NO:13).

Metal binding preference was also analyzed by FPLC. One ml of NTA-agarose column was charged with buffer containing Ni, Cu or Zn and incubated with about 1 mg of purified GST-fused peptide (A15, B16 and C26). Unbound protein was removed by washing with buffer and bound protein eluted with a linear gradient of 0 to 300 mM imidazole. FIGS. 2, 3 and 4 show the FPLC profiles. In each case the strongest binding was observed with Ni (elution at 150-170 mM imidazole), followed by Cu (elution at 75-110 mM imidazole) and Zn (elution at 30-60 mM imidazole).

Concatemers fused to chitin-binding domain (CBD). As disclosed above, one aspect of the teaching provided herein is preparing concatmeric constructs of repeat peptides of multiple histidine binding domains. One example of such a design is the sequence shown in FIG. 5. The concatermeric fusion protein in FIG. 5 has alternating binding domains of peptides A15 and B16 (5 copies) fused to CBD to facilitate large scale purification of metal ions. The construct has the following elements: chitin binding domain (CBD)-Linker (GGSGG; SEQ ID NO:112)-Precision Protease (Pharmacia) cleavage site-A15-Linker(GGS)-B16-Linker(GGS)-A15-Linker(GGS)-B16-Linker(GGS)-A15-FLAG tag-STOP. FLAG tag is an octamer that binds commercially available antibodies and is useful for implementation with techniques such as ELISAs and the like that may include antibody binding as a component.

Binding equivalents. The concatemeric constructs of repeat peptides of alternating metal binding peptides are prepared to increase the relative binding equivalents per molecule of fusion protein with the understand that the increased concentration of binding sites will permit tighter interactions by taking advantage of both high affinity (picomolar dissociation constants) and avidity (multiple repeats of binding peptide).

The core metal binding domains disclosed herein are contained within a 13 residue peptide, the average molecular weight is about 1600 Da. The molecular weight of nickel is 60, so about 27 grams of peptide is needed to bind each gram of nickel. If a set of 5 such peptides are concatenated into a fusion protein without intervening linkers to form a polypeptide with 10 binding equivalents the protein would have a molecular weight of 8,000 Da. Under optimized batch fermentation conditions, a work horse bacterium such as *E. coli* engineered to secrete the fusion protein can secrete approximately 10 to 15 grams of protein per liter, which means it only requires approximately 3.6 to 5.4 liters of fermentation media to produce sufficient protein to bind one gram of nickel or 216 to 320 liters of fermentation to produce one molar equivalent of binding domains, which is vastly superior to the 602,000 liters of phage that would be required to do the same job.

A different method is to overproduce the fusion protein intracellularly. The metal binding peptides described herein are unnatural and may be hydrophobic, hence overproduction of the protein intracellularly may result in the production of inclusion bodies. Bacterial expression hosts specifically engineered for expression of foreign proteins in inclusion bodies are known in the art and capable of yields of as much as 50% of the cell mass. Under ideal fermentation conditions, it is possible to obtain as much as 100 grams of cell mass per liter, which equates to 50 grams of protein which is sufficient to bind 2 grams of nickel, therefore requiring only about 30 liters of cell culture per mole binding equivalent.

Stabilizing genetic concatemers. One of the problems incident to creation of concatermic repeats of peptide coding domains is genetic instability of a repeated coding sequence at the nucleic acid level. It was observed in a first attempt to construct the concatermic fusion peptide of FIG. 5 by DNA synthesis that the occurrence of t repeated units of the same nucleic acid sequence fouled the synthesis operation. In addition, it has been observed that nucleic acid sequences have a tendency to crossover and recombine with homologous genetic sequences of similar primary structure during replication. While such a phenomena is useful for targeting a desired integration event into a particular place in the chromosome of an organism at a desired sequence, the same phenomena is problematic for the intentional creation of concatermic peptides in a single polypeptide chain by fusion of a plurality of repeating coding sequences. Such genetic repeats will cause a higher frequency of crossovers, causing a higher frequency of deletions or other rearrangements of the coding sequence resulting in unpredictable and unstable recombinants.

One aspect of the present teaching is a genetic design method to overcome the problem of genetic instability of repeated coding sequences. The method exploits redundancy in the genetic code caused by codon wobble to design genetic sequences that at the same time encode identical repeated peptides domains while minimizing repeated nucleic acid sequences over the full length of the polypeptide coding sequence. With the exception of tryptophan, the wobble effect typically provides for two to four different codons for each amino acid. The method therefore involves designing the repeated peptide coding sequences for the concatemeric polypeptide to reduce or even mathematically minimize the number of directly repeated coding sequences in the nucleic acid by selecting different cordons for identical amino acids for different sections of the coding sequence. For example, for the nickel binding octapeptide HVHWHAHG (SEQ ID NO:142), tryptophan is the only amino acid encoded by one codon, while histidine can be encoded by 2 codons, and each of the valine, alanine and glycine can by encoded 4 different codons. Thus, for the entire 8 amino acid coding sequence there are 2×4×2×1×4×4 or 256 different coding sequences, therefore for a nucleic acid encoding a concatemer of 10 repeated octapeptides, there are $256^{10}$ possible coding sequences.

Figure 12A:
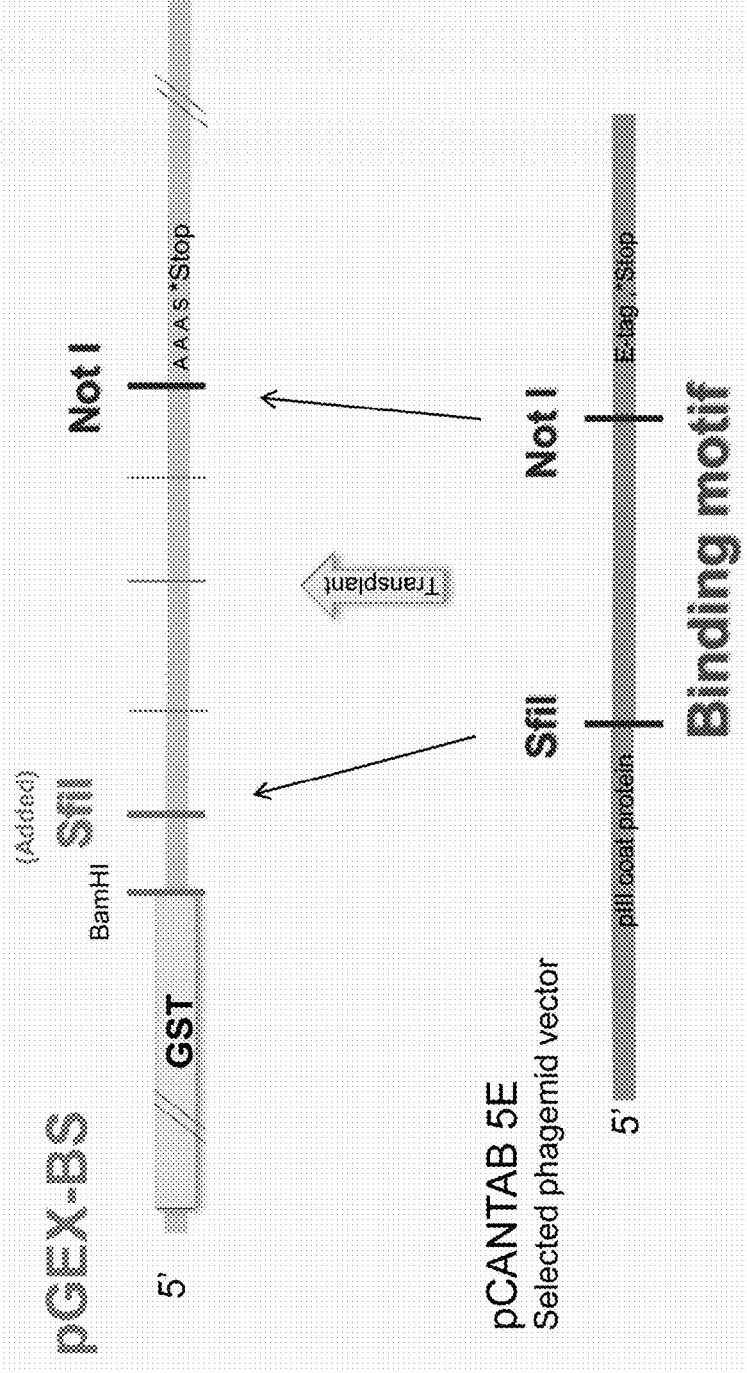
Figure 12B:
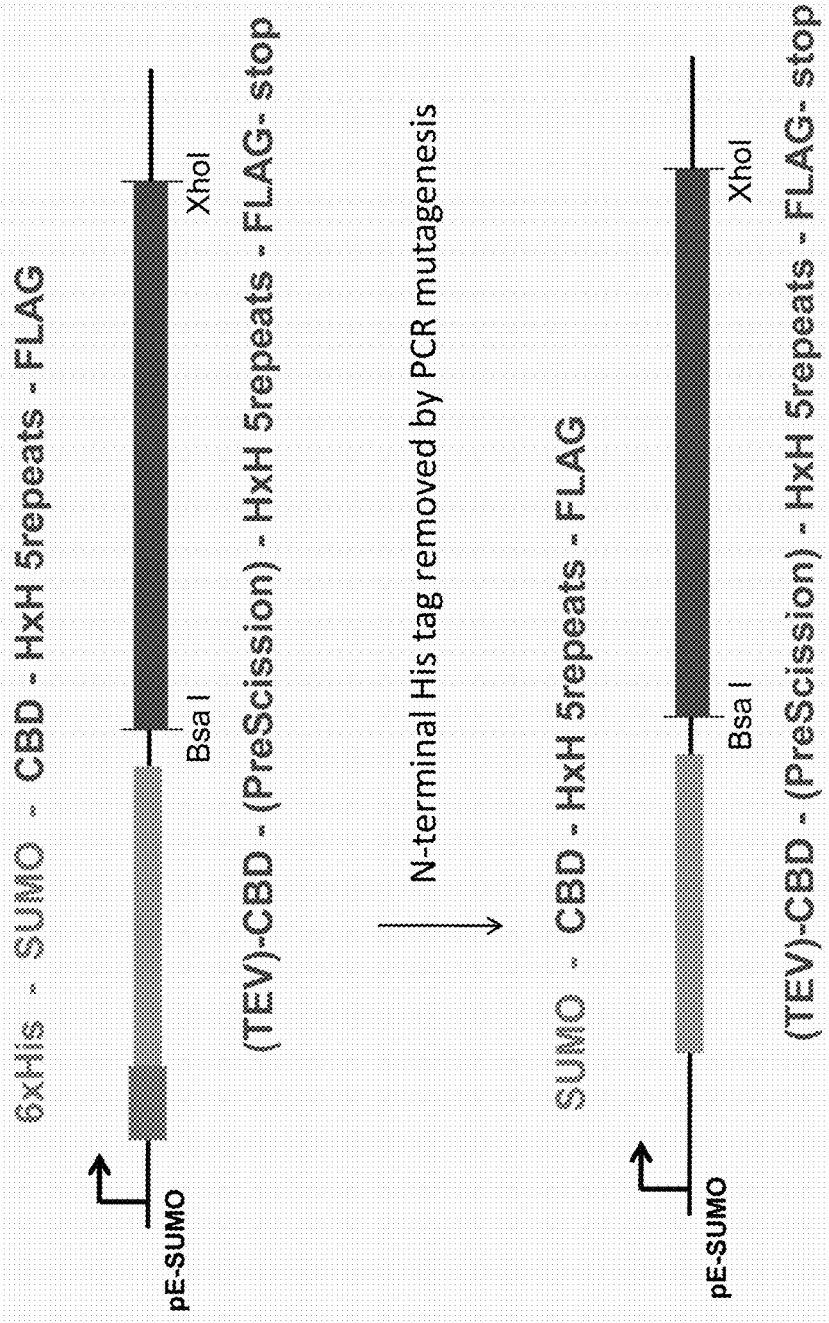
Figure 12C:
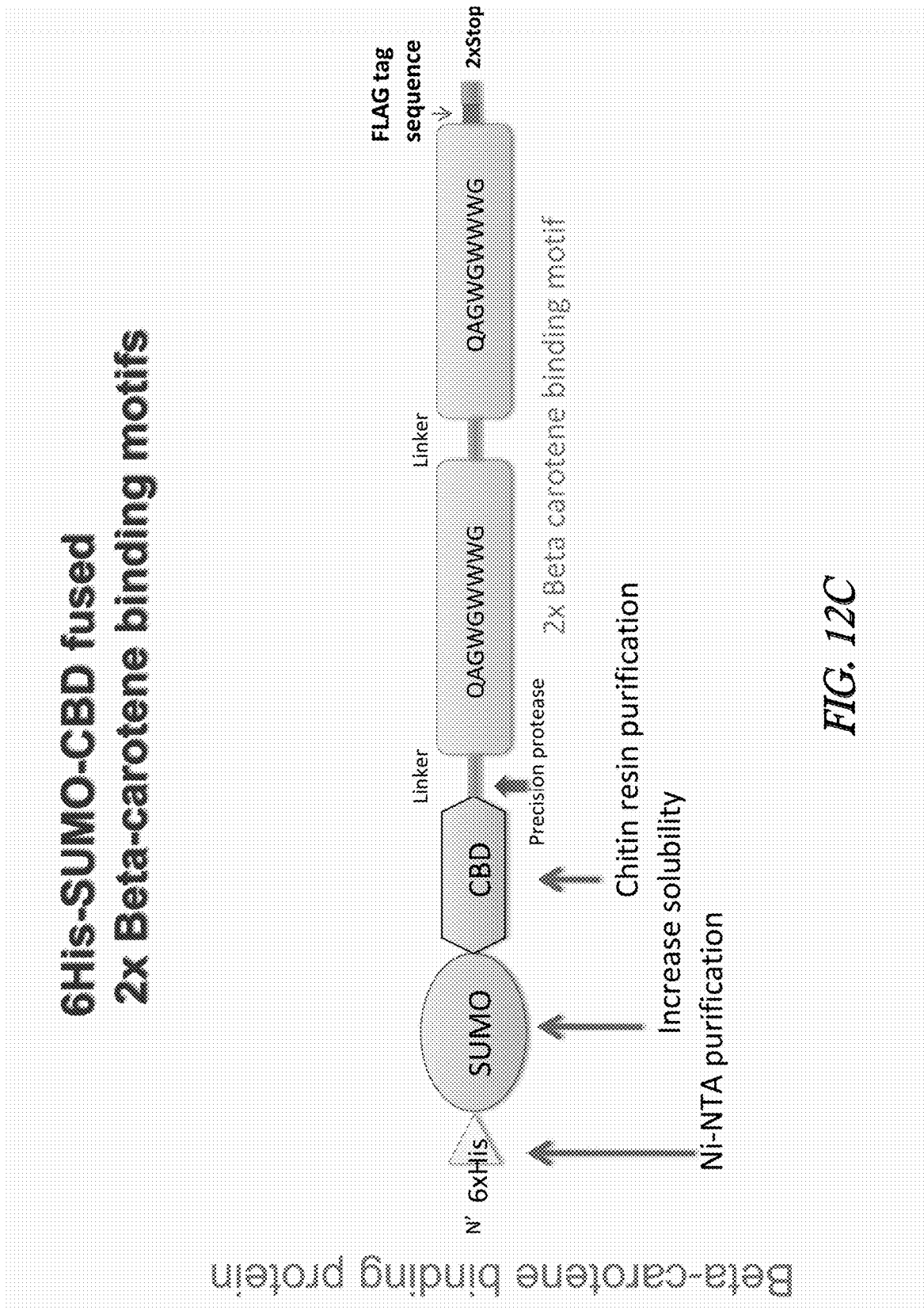
Figure 12D:
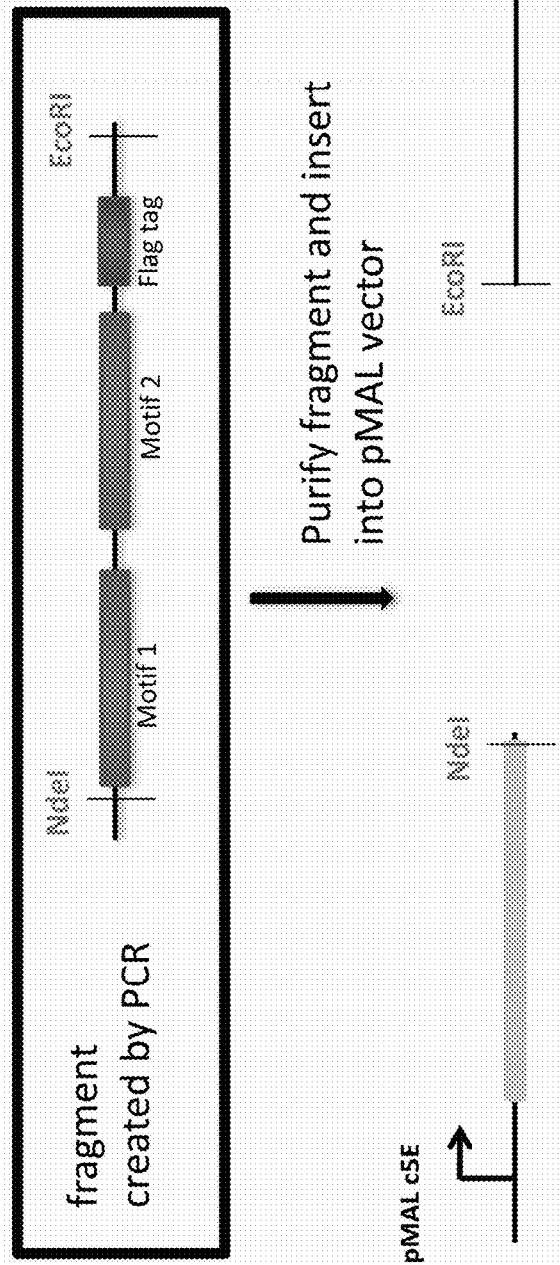
Figure 12E:
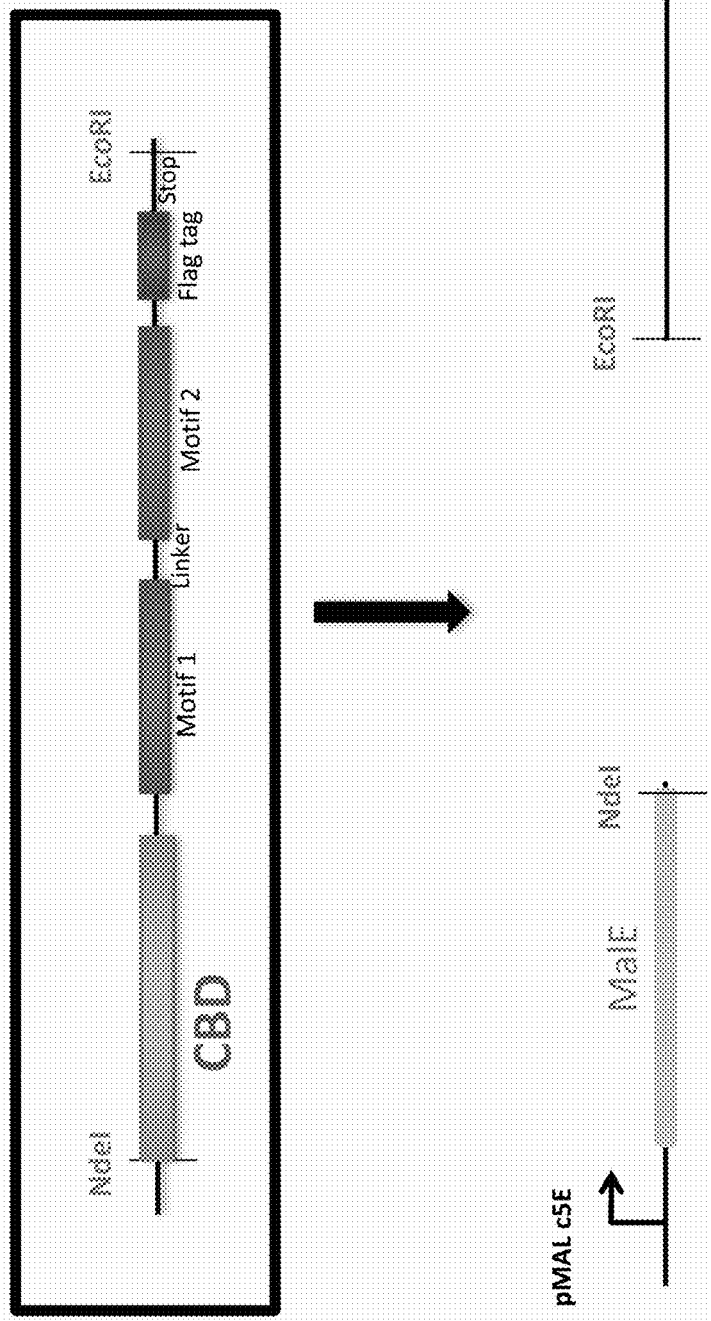

The method provided herein entails selecting amongst the large number of potential coding sequences by taking into consideration each of: (i) the differences between the coding sequences; (ii) the codon bias of the organism in which the sequence will be expressed; and (iii) the distance between the repeats encoded. The principles of design are that the differences between sequences should be maximized, while the use of non preferential codons should be minimized but not necessarily excluded. Moreover, because recombinant crossover events occur with greater frequency between sections of a nucleic acid that are distal to one another in comparison to those that are proximal to one another, the best practice is to design the coding sequence so that repeats occurring further apart from one another are less similar than repeats that are more close to one another. Non preferential codons should preferably not be used at all, but in some cases may be used, but not more than for 2 occurrences of the amino acid to be encoded. Non preferential codons should typically only be used when due to other codon selections, it is necessary to provide an exact repeat of nine or more nucleotides between any two coding domains in the concatemer. An example of a fusion protein containing concatamers of the same metal binding domains encoded by different nucleic acid sequences that was prepared according to these principles is illustrated in FIG. 12F.

Automation or at least assistance in the process can be facilitated by use of bioinformatics software that calculates sequence identity, minimizes sequences identity, and/or that selects codons based upon codon bias. One such publically available software with these functions is Gene Designer™, described by Villalobos et. al. in BMC Bioinformatics 2006, 7:285 and available or downloading from the Internet at http://www.DNA20.com. This software and the article describing it are hereby incorporated by reference to the extent needed to enable one of skill in the art to design nucleic acids encoding concatemers of repeating peptides according to the principles provided herein.

Peptide Sequences that bind β-Carotene Panning experiments were performed essentially as described above except that 30 μL of a solution of β-carotene (10 μg/μL) in 100% chloroform was thinly coated on the inside of a polypropylene microfuge tube ensuring adequate protection from light. After drying with compressed air, it was incubated for 4 hours with 1.5 mL of blocking buffer (PBS containing 3% BSA). The blocking buffer was removed and incubated for 3 hours with 1 mL of phage peptide library (about $1.0\times10^{13}$ pfu) in PBS containing 0.3% BSA and 0.05-0.1% Tween-20. This was followed by 8 steps of washing with PBS containing 0.15% Tween-20. Elution of specifically bound phage was as described above. After four rounds of screening, a number of clones were sequenced and a first consensus tetrapeptide motif [G/P/L—W-x-W/Y/F] (SEQ ID NO:49) was identified (FIG. 6). A secondary 9-amino acid library, x-x-G—W-x-Hy-x-x-x (SEQ ID NO:72) was then constructed with a diversity of >$10^6$ (where x is any amino acid and Hy encodes residues Cys, Phe, Trp, Tyr and Leu but not Val or Ile). This library maintains the above-mentioned core tetrapeptide motif identified from the primary library screening. Repeat panning experiments were performed with the secondary library and sequencing of a number of clones resulted in the further consensus sequence [x-A—G—W-x-W—W—G/W-x] (SEQ ID NO:119) (see FIG. 7).

Based on these results, in addition to the motifs mentioned above, one can describe various embodiments of motifs for carotene binding peptides in several ways. One embodiment may described as peptide comprising a consensus sequence of the formula

 (SEQ ID NO:120)

Where X is any amino acid and Hy is an aromatic amino acid. In several embodiments $X^2$ is alanine. In some embodiments Hy is tryptophan. In some embodiments, $X^4$ is a tryptophan. And in some embodiments, Hy and $X^4$ are each tryptophan. In several embodiments $X^2$ is alanine and Hy is tryptophan. In others $X^2$ is alanine and $X^4$ is tryptophan and in many $X^2$ is alanine and each of Hy and $X^4$ is tryptophan.

Yet another description is a carotene binding peptide comprising a tetra peptide of the sequence of the formula:

$X^1WX^2Hy$ (SEQ ID NO:121)

where $X^1$ is selected from the group consisting of glycine, prolamine and leucine, $X^2$ is any amino acid and Hy is an aromatic amino acid. In many embodiments $X^1$ is glycine.

Figure 11A:
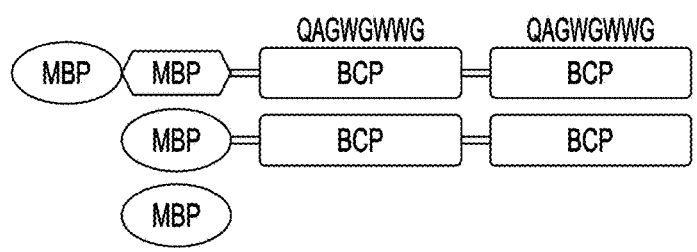
FIGS. 11A-B shows a schematic of fusion proteins with beta-carotene binding domains (SEQ ID NO:55) (A) and absorbance spectra for samples in microfuge tubes coated with beta-carotene and then exposed to fusion proteins with beta-carotene binding domains (B). Samples 1 and 2 lack beta-carotene, while samples 3-7 contained beta-carotene. Sample 3 was exposed to maltose binding protein (MBP), sample 4 was exposed to a MBP-CRK1 fusion, samples 5 and 6 were exposed to a MBP-carotene binding peptide fusion, and sample 7 was exposed to a MBP-CBD-carotene binding peptide fusion.

Two recombinant DNA constructs encoding fusion proteins containing a repeating concatemer of the carotene binding peptide QAGWGWWWG (SEQ ID NO:55) fused to either the maltose-binding protein (MBP) alone, or to the chitin binding domain (CBD) in turn fused to MBP, were constructed, which are illustrated in FIG. 11A. These constructs were cloned into an expression vector containing a promoter for overexpression in *E. coli*. One control construct expressing only the MBP and a second control containing only the MBP fused to a non-specific protein CRK1 each lacking the β-carotene binding domains were also prepared. The MBP protein and fusion proteins containing the MBP could be purified by binding and elution from a column containing immobilized maltose. The fusion proteins were expressed in *E. coli*, purified and analyzed for carotene binding.

An ELISA assay performed in 1.5 mL microfuge tubes that were either coated with β-carotene in a solution with BSA or did not contain β-carotene and were simply blocked with a BSA. In the reactions with β-carotene, 30 μL of a solution of β-carotene (10 μg/μL) in 100% chloroform was thinly coated on the inside of the polypropylene microfuge tube ensuring adequate protection from light. After drying with compressed air, it was incubated for 4 hours with 1.5 mL of blocking buffer (PBS containing 3% BSA). The blocking buffer was removed and incubated for 3 hours with 1 mL of 25 μg/mL of one of the aforementioned fusion proteins containing the β-carotene binding domain concatemers or the control containing the MBP-each with 0.1% BSA as a carrier. Subsequently, the tubes were washed 10 times with PBST and incubated with 1 mL of anti-MBP antibody and incubated for 60 minutes at room temperature. It was then washed 5 times with PBST and incubated with goat anti-rabbit IgG antibody conjugated to alkaline phosphatase for 60 minutes at room temperature, washed 5 times with PBST and color was developed with the appropriate colorimetric substrates for alkaline phosphatase. The solution was then transferred to a 96 well plate for absorbance measurement at 405 nm. The reactions without β-carotene were carried out as above except that the tube add only been blocked with the solution of 3% BSA.

Figure 11B:
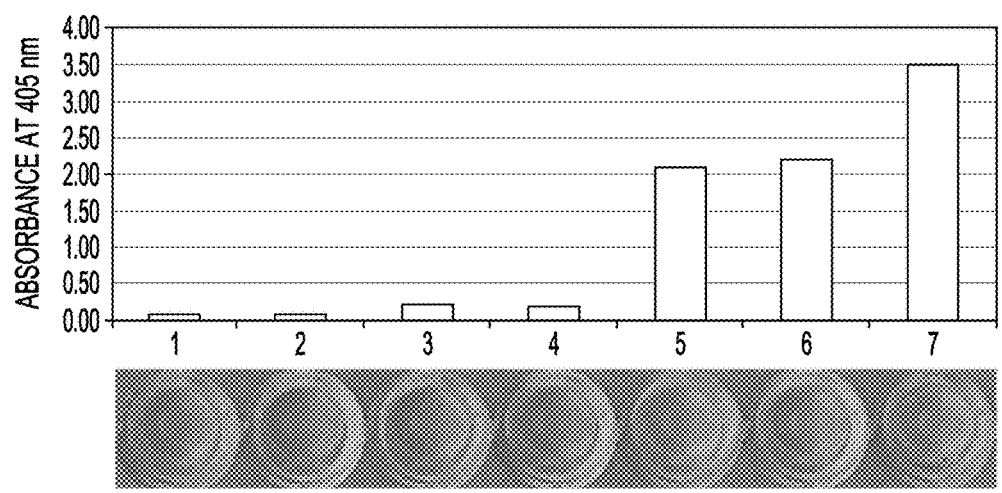

As shown in FIG. 11B, no color was observed when the recombinant fusion protein was incubated in tubes lacking β-carotene indicating that there was no non-specific binding to the microfuge tube surface (samples 1 and 2). No color was observed when the tubes were incubated with the MBP alone (sample 3) or the MBP fused to CRK1 alone (sample 4), indicating that that MBP itself or fused in-frame with a non-specific protein sequence would bind the tubes. However, color was observed when each constructs bearing the β-carotene binding domains fused to MBP alone (samples 5 and 6) or to MBP fused to CBD (sample 7) indicating these binding domains retained the ability to specifically bind β-carotene when present as domains within larger fusion proteins. A similar experiment with similar results was obtained with a MBP-CBD construct fused to the β-carotene binding domain VAGWWWWGA (SEQ ID NO:53).

One embodiment of use of the carotene binding peptides to remove β-carotene from palm oil may employ the amphiphilic characteristic of a fusion protein having a hydrophilic terminus disposed at one end of the protein (e.g., the CBD or MBD such as in FIG. 11) and one or more of the hydrophobic carotene binding peptides distally disposed toward the other end. Palm oil containing β-carotene is mixed with an appropriate amount of polar solvent (e.g., polar organic solvents, water and/or mixtures thereof) and agitated in the presence of the fusion protein to form an emulsion. The emulsion may be comprised of micelles or reverse micelles depending on the amount and type of polar solvent used, with β-carotene bound to the carotene binding domains disposed on one side of the micelle, and the hydrophilic terminus disposed on the other. In the case of conventional micelles, the β-carotene:carotene binding domains are on the interior and the hydrophilic terminus is disposed on the exterior surface of the micelle. In the case of a reverse micelle, the hydrophilic ends are disposed on the interior with the β-carotene:carotene binding domains disposed on the exterior surface. Such micelles are in the form of an aggregate structure with a high molecular weight relative to the triglycerides and fatty acids present in palm oil, and may be separated from the palm oil by filtration over an appropriate molecular weight cutoff membrane. Such a system has been employed for separating lecithin in micellar form from triglycerides in soybean oil processing, see for example U.S. Pat. No. 6,140,519, which is incorporated herein by reference. The β-carotene containing micelles retained on the membrane are dissolved in an appropriate solvent to extract the β-carotene from the micelles and the β-carotene is recovered by evaporation of the solvent from the extract.

In an alternative embodiment, one could immobilize the fusion protein with the binding peptide on a silica gel similarly to the way lipases are immobilized, which leaves the active sites available for interesterification reactions which are performed in a triglyceride media. In the present case the terminus of the fusion protein may be immobilized by cross linking through the CBD or MBD end of the fusion protein thereby displaying the carotene binding peptides on the surface. Palm oil passed over the gel with the immobilized peptide binds the β-carotene and may be concentrated on the solid support relative to the liquid triglyceride phase of the palm oil. The β-carotene bound to the gel may be recovered by elution with an appropriate detergent or solvent and solid gel washed and regenerated for reuse.

Genistein Binding Peptides: Genistein (IUPAC name 5,7-Dihydroxy-3-(4-hydroxyphenyl)chromen-4-one) is a member of a class of molecules referred to as isoflavones. It is found in soybean and a number of other plants and exerts a wide variety of pharmacological effects in animal cells. It is a phytoestrogen, e.g., it interacts with animal and human estrogen receptors causing biological effects similar to those caused by the native estrogen. Isoflavones such as genistein have been implicated as protective agents in hormone-related diseases (menopause), cardiovascular diseases and breast cancer. The biochemical basis of genistein function has been the subject of numerous studies. Amongst the more well known functions of genistein are its ability to inhibit tyrosine kinases and the mammalian hexose transporter GLUT1. Although well known as an inhibitor of tyrosine kinase, it is clear from recent literature that there are other protein targets such as the K-channel protein (Choi et al., 2006, *Korean Journal Physiol Pharmacol*, 10:71-77), cardiac calcium channel protein (Belevych et al., 2002, *Molecular Pharmacology*, 62:554-565) and aldo-keto reductase (Ishikura et al., 2005, *Biol. Pharm. Bull.* 28:1075-1078). In a more recent study, Lavigne et al. (*Breast Cancer Res Treat.* 2008, 110:85-98) have looked at the effects of genistein in global gene expression in MCF-7 breast cancer cell lines using an oligonucleotide microarray system and identified a number of different proteins that are differentially regulated.

Phage panning. In this case panning was performed using a separate phage-peptide library of 22 amino acids from the one used in the above embodiments for metal binding and carotene binding. Genistein (10 µg/mL in ethanol) was coated in a microtiter well and panning performed as described except that in the fourth round, specifically bound phage were released with sequential elutions at pH 4.0, 3.0 and 1.0 and the sequence of the binding peptides was deduced and is shown in FIG. 8.

The sequence motif L-x-L or L-x-x-x-L appears to be present in peptides eluted at pH 4.0 and 3.0. A majority of the clones eluting at pH 4.0 harbored a binding peptide with the sequence SLGLWHSQRHFDVHREHSRHQT (SEQ ID NO:123). A search of this sequence against the non-redundant protein database using the BLASTP program identified a number of proteins that contained a portion of the sequence. A majority of these proteins belonged to the class of glutamyl-tRNA synthetases and aldo-ketoreductases. The latter finding is particularly significant since this class of enzymes has already been implicated in the molecular function of genistein. Importantly, the approach herein using a random phage-displayed library identifies the same class of molecules and, in addition, suggests that the glutamyl-tRNA synthetases may also be hitherto undiscovered target molecules with pharmacological importance.

General Utilities The peptide binding domains disclosed herein for particular targets (e.g., Ni, β-carotene, genestein) are useful in a variety of applications.

One general utility is as component in an assay process. For example, the Ni binding peptides may be used to detect and/or monitor the presence of Ni in a waste water effluent stream. In an exemplary embodiment, a fusion protein carrying one or more of the Ni binding domains exemplified by A15 and B16 fused to CBD illustrated in FIG. 5, could be immobilized on a chitin containing substrate. A control sample of pure water containing a dopant of Ni tagged with a signaling moiety, such as a fluorescent tag, or radioactive Ni, is incubated with the substrate containing the immobilized Ni binding domains and the amount of signal retained after washing is measured. The same is done with pure water containing the same amount of tagged Ni with known concentrations of untagged Ni and the amount of signal retained is used to construct a standard curve. The water sample with unknown amounts Ni is then used in the exact same manner, and the amount of signal retained after washing is compared against the standard curve to determine the amount of Ni in the waste sample. In another example, the fusion protein shown in FIG. 5 carrying the FLAG tag (which binds to antibodies) could be utilized in a similar type of competition assay in ELISA format, whereby the signaling moiety would be the antibody linked to horseradish peroxidase and the amount of Ni determined by the amount of peroxidase activity detected in comparison to a standard curve using known amounts of Ni. This type of general utility is suitable for any peptide binding domain binding any type of target.

As demonstrated by the surface plasmon resonance detection of Ni using the Biocor 3000 Sensor Chip™ with immobilized nickel binding domains (which was used to calculate the dissociation constants for Ni binding), the binding of target molecules of less than 1600 Daltons to peptides immobilized on a substrate may be detected, e.g., by electronic means with extreme sensitivity. This is especially true given that these peptides bind target molecules with a dissociation constant that is $10^{-9}$ M or less. This provides a general method for deployment of peptide binding domains as biosensors for monitoring and detecting the presence of contaminants or dangerous substances, such as explosives or poisons. In one embodiment, a surface plasmon resonance detector is employed as a direct detection method. Other direct detection methods may employ electronic means for detecting fluorescence or spectral properties where the target molecule has a distinctive spectral pattern (such as in the case of β-carotene) or an inherent fluorescent properly (such as in the case of an isothiocyanate). Competition binding may also be employed as a direct method using radioactive or fluorescently labeled targets of known concentration to compete with binding of a target molecule that is present in a sample at unknown concentrations. Indirect methods of detection using fluorescent or spectral detectors may also be employed. For example, in a sandwich type detection assay, an antibody that binds a target molecule and that is also conjugated to a fluorescent moiety or a radioactive tag, may be used to detect and quantify the presence of the target molecule. After contacting the immobilized substrate with a sample containing the target molecule and washing to remove unbound material, the substrate is then contacted with the labeled antibody, which also binds the target molecule. Detection of a signal associated with the label on the antibody, e.g., a fluorescent signal, after washing away unbound antibody allows for quantification of the amount of target molecule bound to the substrate via the peptide binding domain.

Another exemplary utility for the Ni binding peptides is as a waste water treatment reagent. A fusion protein such as illustrated in FIG. 5 containing a total of 10 Ni binding domains in concatemeric arrangement with the linker region and/or substrate binding domain (e.g., CBD) is overexpressed in *E. coli* and purified by binding to the appropriate substrate. The isolated fusion protein is bound via chitin or chemically cross-linked via the linker to a substrate such as a polystyrene resin in a column. The waste water stream is passed over the column for a time sufficient to saturate the column with Ni. The Ni is eluted with an appropriate detergent or denaturant (e.g., imidazole) and the column is regenerated with water and placed back into operation.

In a similar manner, a fusion protein containing a concatmeric arrangement β-carotene binding domains as illustrated for example by FIG. 11, can be used to isolate and recover β-carotene from palm oil processing streams. A column containing the fusion immobilized to a substrate is prepared and the palm oil stream from a processing plant is passed over the column. It may be that in certain embodiments, the palm oil stream needs to be admixed with a portion of water to form an emulsion or micellar suspension for optimal binding because the palm oil will be a hydrophobic solute and the β-carotene binding might work optimally in the presence of some water. In any case, whatever β-carotene binds to the column can be eluted by denaturation or with a hydrophobic solvent, such as hexane, and the column regenerated for further use. The depleted palm oil will have higher value due to the removal of the β-carotene which causes undesirable color, while the recovered β-carotene can be used in a high value product, such as a nutraceutical or antioxidant supplement In analogous fashion, the genistein binding peptides disclosed herein can be used to isolate genistein from soybean processing streams. Genistein is one of the isoflavones present in soybean extracts, and is employed for the treatment of menopause symptoms. Isolation and recovery of purified genistein would produce a high value purified isoflavone useful as a nutraceutical.

Still another general utility for peptide binding domains and concatemeric constructs thereof made with the direction provided herein is for separation of enantiomeric compounds from synthetic manufacturing streams. Often, in the case of pharmaceuticals, the L form of a drug (or just the nucleus of the drug) is biologically more active than the D form. Using the L form of the drug, or a precursor used in the manufacture of the nucleus, as the target for panning phage libraries will result in protein binding domains that preferentially bind the L form of the drug or precursor. Columns having such binding domains immobilized on a substrate can be used to purify the L form of the drug from synthetic processing streams, which typically produce enantiomeric mixtures.

High Throughput Membrane Based Phage Panning The binding domains described herein were obtained by panning phage libraries by sequential binding of whole libraries to a substrate containing the target molecule of interest, washing out unbound phage particles to obtain a subset of the library that bound the phage. Eluting the bound phage and repeating the process three of four times before isolating individual plaques of phage representing clones of the same displayed peptide.

An alternative for high throughput panning is to directly screen for individual phage plaques within the whole library by transferring a whole library from an agar plate onto a membrane, contacting the plaques lifted onto the membrane with the target molecule that itself emits a signal, e.g., due to a radioisotope labeling, or that is linked to a signaling moiety, washing the membrane to remove non specific binding, and detecting plaques that emit the appropriate signal. In the case of very small inorganic targets or elements such as metals, the most direct method may be use of radioisotopes of the metal whose signal can be readily detected by exposure to X-ray film or a CCD imaging apparatus capable of detecting radioactive emissions. Radioactive isotopes for many elements and many organic molecules synthesized with radioactive isotopes are available on the market from suppliers such as PerkinElmer (Waltham, Mass.) which also offers custom synthesis services.

For larger target molecules where steric hindrance is less likely to be a factor affecting binding, one alternative type of signaling moeity can be fluorescent labels tethered to the target molecule. Typical fluorescent labels include isothiocyanates such as FITC and TRTC which are cyanate derivatives of fluorescein and rhodamine, respectively. Others include succinimidyl ester and sulfhdyrl reactive maleimides of fluorescein These labels can be chemically linked directly, or through spacer arms, to a variety of functional groups that may be available on the target molecule of interest and can be obtained from a variety of suppliers that provide kits for chemical cross linking of the labels to various functional groups.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

SEQUENCE LISTING

```
<160> NUMBER OF SEQ ID NOS: 150

<210> SEQ ID NO 1
<211> LENGTH: 13
<212> TYPE: PRT
<213> ORGANISM: Artificial Sequence
<220> FEATURE:
<223> OTHER INFORMATION: A synthetic peptide

<400> SEQUENCE: 1

Tyr Ser His His His His His His Leu Ala Gly Thr Ala
1               5                   10

<210> SEQ ID NO 2
<211> LENGTH: 12
<212> TYPE: PRT
<213> ORGANISM: Artificial Sequence
<220> FEATURE:
<223> OTHER INFORMATION: A synthetic peptide

<400> SEQUENCE: 2

His Gln His Gln His Gln His Gln His Gln His Gln
1               5                   10

<210> SEQ ID NO 3
<211> LENGTH: 6
<212> TYPE: PRT
<213> ORGANISM: Artificial Sequence
<220> FEATURE:
<223> OTHER INFORMATION: A synthetic peptide
<220> FEATURE:
```

```
<221> NAME/KEY: SITE
<222> LOCATION: 3
<223> OTHER INFORMATION: Xaa is any amino acid

<400> SEQUENCE: 3

Arg His Xaa His His Arg
 1               5

<210> SEQ ID NO 4
<211> LENGTH: 9
<212> TYPE: PRT
<213> ORGANISM: Artificial Sequence
<220> FEATURE:
<223> OTHER INFORMATION: A synthetic peptide

<400> SEQUENCE: 4

Gly Cys Gly Cys Pro Cys Gly Cys Gly
 1               5

<210> SEQ ID NO 5
<211> LENGTH: 13
<212> TYPE: PRT
<213> ORGANISM: Artificial Sequence
<220> FEATURE:
<223> OTHER INFORMATION: A synthetic peptide

<400> SEQUENCE: 5

Leu Cys Cys Tyr Trp Ser Tyr Ser Arg Met Cys Lys Ala
 1               5                   10

<210> SEQ ID NO 6
<211> LENGTH: 12
<212> TYPE: PRT
<213> ORGANISM: Artificial Sequence
<220> FEATURE:
<223> OTHER INFORMATION: A synthetic peptide

<400> SEQUENCE: 6

Leu Lys Ala His Leu Pro Pro Ser Arg Leu Pro Ser
 1               5                   10

<210> SEQ ID NO 7
<211> LENGTH: 12
<212> TYPE: PRT
<213> ORGANISM: Artificial Sequence
<220> FEATURE:
<223> OTHER INFORMATION: A synthetic peptide

<400> SEQUENCE: 7

Val Pro Ser Ser Gly Pro Gln Asp Thr Arg Thr Thr
 1               5                   10

<210> SEQ ID NO 8

<400> SEQUENCE: 8

000

<210> SEQ ID NO 9
<211> LENGTH: 13
<212> TYPE: PRT
<213> ORGANISM: Artificial Sequence
<220> FEATURE:
<223> OTHER INFORMATION: A synthetic peptide

<400> SEQUENCE: 9

Tyr Thr Arg Thr Pro His Val His Trp His Ala His Gly
```

<210> SEQ ID NO 10

<400> SEQUENCE: 10

000

<210> SEQ ID NO 11
<211> LENGTH: 13
<212> TYPE: PRT
<213> ORGANISM: Artificial Sequence
<220> FEATURE:
<223> OTHER INFORMATION: A synthetic peptide

<400> SEQUENCE: 11

Trp Gly Gly Trp Arg His Val His Gly His Arg His Pro
 1               5                  10

<210> SEQ ID NO 12

<400> SEQUENCE: 12

000

<210> SEQ ID NO 13
<211> LENGTH: 13
<212> TYPE: PRT
<213> ORGANISM: Artificial Sequence
<220> FEATURE:
<223> OTHER INFORMATION: A synthetic peptide

<400> SEQUENCE: 13

Tyr Glu His His His His His His Leu Ala Gly Thr Ala
 1               5                  10

<210> SEQ ID NO 14
<211> LENGTH: 542
<212> TYPE: DNA
<213> ORGANISM: Artificial Sequence
<220> FEATURE:
<223> OTHER INFORMATION: A synthetic oligonucleotide

<400> SEQUENCE: 14

```
gaattccccg ggtttaagaa ggagatatac atatgggtct gaactcaggc ctcacgacaa      60
atcctggtgt atccgcttgg caggtcaaca cagcttatac tgcgggacaa ttggtcacat     120
ataacggcaa gacgtataaa tgtttgcagc cccacacctc cttggcagga tgggaaccat     180
ccaacgttcc tgccttgtgg cagcttcaag gtggctctgg tggcctggaa gttctgttcc     240
aggggcccgg cccagccggc cgttatacgc gtacacctca tgtgcactgg catgcgcacg     300
gcggttcttg gggcggatgg cgacacgtac acggtcatcg tcatcccgga ggatcataca     360
cccggactcc gcacgtacat tggcacgcac atggaggctc gtggggtggg tggcgccatg     420
tccatggcca ccgacaccct gggggatcct acacacgcac gccacatgtc cattggcacg     480
ctcacggggg cggccgcgac tacaaggatg acgatgacaa gtaatagaag cttgagctcg     540
ag                                                                   542
```

<210> SEQ ID NO 15
<211> LENGTH: 163
<212> TYPE: PRT
<213> ORGANISM: Artificial Sequence
<220> FEATURE:
<223> OTHER INFORMATION: A synthetic peptide

<400> SEQUENCE: 15

Met Gly Leu Asn Ser Gly Leu Thr Thr Asn Pro Gly Val Ser Ala Trp
1               5                   10                  15

Gln Val Asn Thr Ala Tyr Thr Ala Gly Gln Leu Val Thr Tyr Asn Gly
            20                  25                  30

Lys Thr Tyr Lys Cys Leu Gln Pro His Thr Ser Leu Ala Gly Trp Glu
        35                  40                  45

Pro Ser Asn Val Pro Ala Leu Trp Gln Leu Gln Gly Ser Gly Gly
    50                  55                  60

Leu Glu Val Leu Phe Gln Gly Pro Gly Pro Ala Gly Arg Tyr Thr Arg
65              70                  75                  80

Thr Pro His Val His Trp His Ala His Gly Gly Ser Trp Gly Gly Trp
                85                  90                  95

Arg His Val His Gly His Arg His Pro Gly Gly Ser Tyr Thr Arg Thr
                100                 105                 110

Pro His Val His Trp His Ala His Gly Gly Ser Trp Gly Gly Trp Arg
                115                 120                 125

His Val His Gly His Arg His Pro Gly Gly Ser Tyr Thr Arg Thr Pro
            130                 135                 140

His Val His Trp His Ala His Gly Gly Gly Arg Asp Tyr Lys Asp Asp
145                 150                 155                 160

Asp Asp Lys

<210> SEQ ID NO 16
<211> LENGTH: 21
<212> TYPE: PRT
<213> ORGANISM: Artificial Sequence
<220> FEATURE:
<223> OTHER INFORMATION: A synthetic peptide

<400> SEQUENCE: 16

Val Ser His Tyr Ile Pro Arg Phe Arg Ile Leu His Gly Pro Phe Ser
1               5                   10                  15

Gly Val Gly Trp Ser
            20

<210> SEQ ID NO 17
<211> LENGTH: 20
<212> TYPE: PRT
<213> ORGANISM: Artificial Sequence
<220> FEATURE:
<223> OTHER INFORMATION: A synthetic peptide

<400> SEQUENCE: 17

Val Ser Tyr Glu Glu Thr Leu Phe Tyr Ser Gly Trp Pro Trp Tyr Val
1               5                   10                  15

Asp Met Pro Arg
            20

<210> SEQ ID NO 18
<211> LENGTH: 21
<212> TYPE: PRT
<213> ORGANISM: Artificial Sequence
<220> FEATURE:
<223> OTHER INFORMATION: A synthetic peptide

<400> SEQUENCE: 18

Trp Ser Tyr Trp Leu Tyr Pro Phe Gly Gly Phe Trp Phe Ser Ser Thr
1               5                   10                  15

```
Asn Asp Leu His Ala
            20

<210> SEQ ID NO 19
<211> LENGTH: 21
<212> TYPE: PRT
<213> ORGANISM: Artificial Sequence
<220> FEATURE:
<223> OTHER INFORMATION: A synthetic peptide

<400> SEQUENCE: 19

Phe Gly Ser Tyr Tyr Gly Trp Trp Ser Trp Asp Leu Ser Pro Arg Met
 1               5                  10                  15

Arg Glu His Ile Ala
            20

<210> SEQ ID NO 20
<211> LENGTH: 21
<212> TYPE: PRT
<213> ORGANISM: Artificial Sequence
<220> FEATURE:
<223> OTHER INFORMATION: A synthetic peptide

<400> SEQUENCE: 20

Ser Asn Asn His Leu His Arg Asp Asp Leu Ser Leu Leu Ala Thr Gly
 1               5                  10                  15

Trp Val His Ser Met
            20

<210> SEQ ID NO 21
<211> LENGTH: 21
<212> TYPE: PRT
<213> ORGANISM: Artificial Sequence
<220> FEATURE:
<223> OTHER INFORMATION: A synthetic peptide

<400> SEQUENCE: 21

Tyr Gly Trp Met Val Ser Trp Ile Thr Cys Leu Val Ser Pro Asn Cys
 1               5                  10                  15

Thr Glu Gln Thr Ser
            20

<210> SEQ ID NO 22
<211> LENGTH: 19
<212> TYPE: PRT
<213> ORGANISM: Artificial Sequence
<220> FEATURE:
<223> OTHER INFORMATION: A synthetic peptide

<400> SEQUENCE: 22

Trp Thr Ser Thr Ala Phe Met Ser Val Leu Gly Trp Val Tyr Val Ile
 1               5                  10                  15

Val Val Leu

<210> SEQ ID NO 23
<211> LENGTH: 21
<212> TYPE: PRT
<213> ORGANISM: Artificial Sequence
<220> FEATURE:
<223> OTHER INFORMATION: A synthetic peptide

<400> SEQUENCE: 23

Leu Phe Gly Trp Gln Phe Pro Leu Ser His Val Asp Glu Ser Ser Gly
 1               5                  10                  15
```

Arg Gly Ser Glu Ser
        20

<210> SEQ ID NO 24
<211> LENGTH: 21
<212> TYPE: PRT
<213> ORGANISM: Artificial Sequence
<220> FEATURE:
<223> OTHER INFORMATION: A synthetic peptide

<400> SEQUENCE: 24

Ile Lys Trp Val His His Leu Met Gly Trp Ser His Trp Leu Gly Asn
1               5                   10                  15

Gln Ile Phe Gln Ala
        20

<210> SEQ ID NO 25
<211> LENGTH: 21
<212> TYPE: PRT
<213> ORGANISM: Artificial Sequence
<220> FEATURE:
<223> OTHER INFORMATION: A synthetic peptide

<400> SEQUENCE: 25

Leu Thr Trp Gly Thr Leu Phe Leu Cys Leu Arg Gly Trp Ser Val Ile
1               5                   10                  15

Tyr Ala Cys Asn Tyr
        20

<210> SEQ ID NO 26
<211> LENGTH: 21
<212> TYPE: PRT
<213> ORGANISM: Artificial Sequence
<220> FEATURE:
<223> OTHER INFORMATION: A synthetic peptide

<400> SEQUENCE: 26

Ile Thr Phe Ile Leu Asn Met Val Thr Ser Phe Asn Pro Trp Ser Val
1               5                   10                  15

Asp Thr Val Arg Val
        20

<210> SEQ ID NO 27
<211> LENGTH: 21
<212> TYPE: PRT
<213> ORGANISM: Artificial Sequence
<220> FEATURE:
<223> OTHER INFORMATION: A synthetic peptide

<400> SEQUENCE: 27

Leu Ser Lys His Gly Gln Met Ile Leu Ser Val Pro Trp His Trp Trp
1               5                   10                  15

Asn Ile Phe Pro Trp
        20

<210> SEQ ID NO 28
<211> LENGTH: 21
<212> TYPE: PRT
<213> ORGANISM: Artificial Sequence
<220> FEATURE:
<223> OTHER INFORMATION: A synthetic peptide

<400> SEQUENCE: 28

Trp Ser Tyr Trp Leu Tyr Pro Phe Gly Gly Phe Trp Phe Ser Ser Thr

Asn Asp Leu His Ala
            20

<210> SEQ ID NO 29
<211> LENGTH: 21
<212> TYPE: PRT
<213> ORGANISM: Artificial Sequence
<220> FEATURE:
<223> OTHER INFORMATION: A synthetic peptide

<400> SEQUENCE: 29

Thr Val Phe Arg Tyr Pro Ala Leu Pro Asn Leu Trp Ser Phe Leu Asn
1               5                   10                  15

Val Phe Asn Gly Leu
            20

<210> SEQ ID NO 30
<211> LENGTH: 20
<212> TYPE: PRT
<213> ORGANISM: Artificial Sequence
<220> FEATURE:
<223> OTHER INFORMATION: A synthetic peptide

<400> SEQUENCE: 30

Thr Val Ser Leu Trp Phe Leu Gly Thr Ile Val Asn Met Val Thr Phe
1               5                   10                  15

Ile Leu Gly Leu
            20

<210> SEQ ID NO 31
<211> LENGTH: 21
<212> TYPE: PRT
<213> ORGANISM: Artificial Sequence
<220> FEATURE:
<223> OTHER INFORMATION: A synthetic peptide

<400> SEQUENCE: 31

Ser Val Leu Asp Phe Arg Asp Leu Leu Gln Trp Phe Ala Gly Gly Arg
1               5                   10                  15

Trp Gly Asp Phe Gly
            20

<210> SEQ ID NO 32
<211> LENGTH: 21
<212> TYPE: PRT
<213> ORGANISM: Artificial Sequence
<220> FEATURE:
<223> OTHER INFORMATION: A synthetic peptide

<400> SEQUENCE: 32

Met Ala Phe Asp Pro Tyr Tyr Ile Leu Lys Pro Ser Tyr Trp Phe His
1               5                   10                  15

Gly Thr Gly Leu Thr
            20

<210> SEQ ID NO 33
<211> LENGTH: 21
<212> TYPE: PRT
<213> ORGANISM: Artificial Sequence
<220> FEATURE:
<223> OTHER INFORMATION: A synthetic peptide

<400> SEQUENCE: 33

```
Ile Pro Gly Thr Asp Asp Val Arg Gly Ser Leu Trp Phe Leu Pro Ser
1               5                   10                  15

Ser Pro Glu Arg Tyr
            20

<210> SEQ ID NO 34
<211> LENGTH: 21
<212> TYPE: PRT
<213> ORGANISM: Artificial Sequence
<220> FEATURE:
<223> OTHER INFORMATION: A synthetic peptide

<400> SEQUENCE: 34

Ser His Gly Asp Pro Trp Asn Thr Leu Trp Phe Trp Pro Leu Gln Leu
1               5                   10                  15

Arg Ser Phe Trp His
            20

<210> SEQ ID NO 35
<211> LENGTH: 20
<212> TYPE: PRT
<213> ORGANISM: Artificial Sequence
<220> FEATURE:
<223> OTHER INFORMATION: A synthetic peptide

<400> SEQUENCE: 35

Thr Ala Ala Leu Trp His Leu Trp Pro Trp Asn Phe Met Arg Thr Lys
1               5                   10                  15

Thr Gln Tyr His
            20

<210> SEQ ID NO 36
<211> LENGTH: 21
<212> TYPE: PRT
<213> ORGANISM: Artificial Sequence
<220> FEATURE:
<223> OTHER INFORMATION: A synthetic peptide

<400> SEQUENCE: 36

Leu Gly Leu Pro Asn Phe Trp Val Trp Asp Phe Trp Gln Lys Trp Ile
1               5                   10                  15

Gly Asn Ala Gly Gly
            20

<210> SEQ ID NO 37
<211> LENGTH: 21
<212> TYPE: PRT
<213> ORGANISM: Artificial Sequence
<220> FEATURE:
<223> OTHER INFORMATION: A synthetic peptide

<400> SEQUENCE: 37

Tyr Gln Leu Val Trp Pro Tyr Leu Val Tyr Asp Gly Gly Gly Met Ala
1               5                   10                  15

Thr Asn Thr Pro Gln
            20

<210> SEQ ID NO 38
<211> LENGTH: 20
<212> TYPE: PRT
<213> ORGANISM: Artificial Sequence
<220> FEATURE:
<223> OTHER INFORMATION: A synthetic peptide

<400> SEQUENCE: 38
```

```
Gln Arg Thr Met Trp Pro Tyr Leu Ser Gly Phe Leu Lys His Tyr Val
1               5                   10                  15

Leu Gly Thr Trp
            20

<210> SEQ ID NO 39
<211> LENGTH: 21
<212> TYPE: PRT
<213> ORGANISM: Artificial Sequence
<220> FEATURE:
<223> OTHER INFORMATION: A synthetic peptide

<400> SEQUENCE: 39

Tyr Asp Trp Leu Tyr Ala Tyr Glu Thr Phe Met Glu Asp Leu Ile Ser
1               5                   10                  15

Arg Ala His Gly Ile
            20

<210> SEQ ID NO 40
<211> LENGTH: 20
<212> TYPE: PRT
<213> ORGANISM: Artificial Sequence
<220> FEATURE:
<223> OTHER INFORMATION: A synthetic peptide

<400> SEQUENCE: 40

Trp Leu Phe Asn Gly Phe Arg Thr Pro Ser Asn Ile Gly Asp Gly Tyr
1               5                   10                  15

Lys Met Arg Phe
            20

<210> SEQ ID NO 41
<211> LENGTH: 21
<212> TYPE: PRT
<213> ORGANISM: Artificial Sequence
<220> FEATURE:
<223> OTHER INFORMATION: A synthetic peptide

<400> SEQUENCE: 41

Arg Glu Ala Trp Thr Lys Val Leu Asp Trp Leu Asn Ser Pro Met Asn
1               5                   10                  15

Leu Gly Thr Ser Gly
            20

<210> SEQ ID NO 42
<211> LENGTH: 21
<212> TYPE: PRT
<213> ORGANISM: Artificial Sequence
<220> FEATURE:
<223> OTHER INFORMATION: A synthetic peptide

<400> SEQUENCE: 42

Ala Ile Leu Ser Gly Gly Met Val Trp Leu Val Gln Gln Gly Arg Ala
1               5                   10                  15

Leu Val His Trp Ser
            20

<210> SEQ ID NO 43
<211> LENGTH: 21
<212> TYPE: PRT
<213> ORGANISM: Artificial Sequence
<220> FEATURE:
<223> OTHER INFORMATION: A synthetic peptide
```

```
<400> SEQUENCE: 43

Trp Tyr Leu Arg Phe Thr Val Leu Phe Asn His Leu Phe Thr Pro Leu
1               5                   10                  15

Ala Thr Ile Phe Ala
            20

<210> SEQ ID NO 44
<211> LENGTH: 21
<212> TYPE: PRT
<213> ORGANISM: Artificial Sequence
<220> FEATURE:
<223> OTHER INFORMATION: A synthetic peptide

<400> SEQUENCE: 44

Ile Thr Trp Tyr Glu Ala Leu Val Asn Arg Tyr Lys Gly Met Leu Ala
1               5                   10                  15

Asn Lys Thr Pro Ser
            20

<210> SEQ ID NO 45
<211> LENGTH: 21
<212> TYPE: PRT
<213> ORGANISM: Artificial Sequence
<220> FEATURE:
<223> OTHER INFORMATION: A synthetic peptide

<400> SEQUENCE: 45

Phe Ser Phe Met Ser Trp Met Gln Phe Met Gly Phe Thr Arg Val Leu
1               5                   10                  15

Thr Val Asp Ile Gly
            20

<210> SEQ ID NO 46
<211> LENGTH: 20
<212> TYPE: PRT
<213> ORGANISM: Artificial Sequence
<220> FEATURE:
<223> OTHER INFORMATION: A synthetic peptide

<400> SEQUENCE: 46

Trp Gly Val Tyr Ile Leu Pro Asn Ser Ile Glu Met Leu Ser Ala Leu
1               5                   10                  15

Ala Ile Gly Leu
            20

<210> SEQ ID NO 47
<211> LENGTH: 20
<212> TYPE: PRT
<213> ORGANISM: Artificial Sequence
<220> FEATURE:
<223> OTHER INFORMATION: A synthetic peptide

<400> SEQUENCE: 47

Trp Lys Asn Phe Asp Ser Phe Val Phe Thr Arg Asp Tyr Val Arg Asp
1               5                   10                  15

Val Val Leu His
            20

<210> SEQ ID NO 48
<211> LENGTH: 20
<212> TYPE: PRT
<213> ORGANISM: Artificial Sequence
<220> FEATURE:
<223> OTHER INFORMATION: A synthetic peptide
```

```
<400> SEQUENCE: 48

Lys Ala Val Ser Ser Pro Trp Asn Phe Ile Cys Trp Met Gln Lys Pro
1               5                   10                  15

Ser Gly Cys His
            20

<210> SEQ ID NO 49
<211> LENGTH: 4
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: (1)...(4)
<223> OTHER INFORMATION: Xaa is any amino acid

<400> SEQUENCE: 49

Xaa Trp Xaa Xaa
1

<210> SEQ ID NO 50
<211> LENGTH: 9
<212> TYPE: PRT
<213> ORGANISM: Artificial Sequence
<220> FEATURE:
<223> OTHER INFORMATION: A synthetic peptide

<400> SEQUENCE: 50

Val Ala Gly Trp Trp Trp Trp Gly Thr
1               5

<210> SEQ ID NO 51
<211> LENGTH: 9
<212> TYPE: PRT
<213> ORGANISM: Artificial Sequence
<220> FEATURE:
<223> OTHER INFORMATION: A synthetic peptide

<400> SEQUENCE: 51

Trp Ala Gly Trp Met Trp Trp Trp Gly
1               5

<210> SEQ ID NO 52
<211> LENGTH: 9
<212> TYPE: PRT
<213> ORGANISM: Artificial Sequence
<220> FEATURE:
<223> OTHER INFORMATION: A synthetic peptide

<400> SEQUENCE: 52

Leu Ala Gly Trp Gly Trp Trp Gly Trp
1               5

<210> SEQ ID NO 53
<211> LENGTH: 9
<212> TYPE: PRT
<213> ORGANISM: Artificial Sequence
<220> FEATURE:
<223> OTHER INFORMATION: A synthetic peptide

<400> SEQUENCE: 53

Val Ala Gly Trp Trp Trp Trp Gly Ala
1               5
```

```
<210> SEQ ID NO 54
<211> LENGTH: 9
<212> TYPE: PRT
<213> ORGANISM: Artificial Sequence
<220> FEATURE:
<223> OTHER INFORMATION: A synthetic peptide

<400> SEQUENCE: 54

Trp Ala Gly Trp Gly Trp Trp Ser Trp
1               5

<210> SEQ ID NO 55
<211> LENGTH: 9
<212> TYPE: PRT
<213> ORGANISM: Artificial Sequence
<220> FEATURE:
<223> OTHER INFORMATION: A synthetic peptide

<400> SEQUENCE: 55

Gln Ala Gly Trp Gly Trp Trp Trp Gly
1               5

<210> SEQ ID NO 56
<211> LENGTH: 9
<212> TYPE: PRT
<213> ORGANISM: Artificial Sequence
<220> FEATURE:
<223> OTHER INFORMATION: A synthetic peptide

<400> SEQUENCE: 56

Ser Ala Gly Trp Gly Trp Met Trp Trp
1               5

<210> SEQ ID NO 57
<211> LENGTH: 9
<212> TYPE: PRT
<213> ORGANISM: Artificial Sequence
<220> FEATURE:
<223> OTHER INFORMATION: A synthetic peptide

<400> SEQUENCE: 57

Trp Gly Gly Trp Gly Trp Trp Trp Gly
1               5

<210> SEQ ID NO 58
<211> LENGTH: 9
<212> TYPE: PRT
<213> ORGANISM: Artificial Sequence
<220> FEATURE:
<223> OTHER INFORMATION: A synthetic peptide

<400> SEQUENCE: 58

Trp Cys Gly Trp Trp Trp Trp Gly Trp
1               5

<210> SEQ ID NO 59
<211> LENGTH: 9
<212> TYPE: PRT
<213> ORGANISM: Artificial Sequence
<220> FEATURE:
<223> OTHER INFORMATION: A synthetic peptide

<400> SEQUENCE: 59

Tyr Ala Gly Trp Phe Trp Gly Trp Met
1               5

<210> SEQ ID NO 60
```

```
<211> LENGTH: 9
<212> TYPE: PRT
<213> ORGANISM: Artificial Sequence
<220> FEATURE:
<223> OTHER INFORMATION: A synthetic peptide

<400> SEQUENCE: 60

Leu Ala Gly Trp Leu Trp Trp Trp Gly
 1               5

<210> SEQ ID NO 61
<211> LENGTH: 9
<212> TYPE: PRT
<213> ORGANISM: Artificial Sequence
<220> FEATURE:
<223> OTHER INFORMATION: A synthetic peptide

<400> SEQUENCE: 61

Phe Ala Gly Trp Phe Trp Trp Gly Thr
 1               5

<210> SEQ ID NO 62
<211> LENGTH: 9
<212> TYPE: PRT
<213> ORGANISM: Artificial Sequence
<220> FEATURE:
<223> OTHER INFORMATION: A synthetic peptide

<400> SEQUENCE: 62

Thr Ala Gly Trp Trp Trp Gly Pro Trp
 1               5

<210> SEQ ID NO 63
<211> LENGTH: 9
<212> TYPE: PRT
<213> ORGANISM: Artificial Sequence
<220> FEATURE:
<223> OTHER INFORMATION: A synthetic peptide

<400> SEQUENCE: 63

Ala Cys Gly Trp Tyr Phe Pro Ser Asn
 1               5

<210> SEQ ID NO 64
<211> LENGTH: 9
<212> TYPE: PRT
<213> ORGANISM: Artificial Sequence
<220> FEATURE:
<223> OTHER INFORMATION: A synthetic peptide

<400> SEQUENCE: 64

Phe Gly Gly Trp Trp Trp Thr Trp Trp
 1               5

<210> SEQ ID NO 65
<211> LENGTH: 9
<212> TYPE: PRT
<213> ORGANISM: Artificial Sequence
<220> FEATURE:
<223> OTHER INFORMATION: A synthetic peptide

<400> SEQUENCE: 65

Ala Ile Gly Trp Pro Trp Trp Leu Val
 1               5

<210> SEQ ID NO 66
<211> LENGTH: 9
```

```
<212> TYPE: PRT
<213> ORGANISM: Artificial Sequence
<220> FEATURE:
<223> OTHER INFORMATION: A synthetic peptide

<400> SEQUENCE: 66

Ile Ala Gly Trp Leu Tyr Trp Trp Ala
 1               5

<210> SEQ ID NO 67
<211> LENGTH: 9
<212> TYPE: PRT
<213> ORGANISM: Artificial Sequence
<220> FEATURE:
<223> OTHER INFORMATION: A synthetic peptide

<400> SEQUENCE: 67

Trp Trp Gly Trp Gly Trp Gly Gln Trp
 1               5

<210> SEQ ID NO 68
<211> LENGTH: 9
<212> TYPE: PRT
<213> ORGANISM: Artificial Sequence
<220> FEATURE:
<223> OTHER INFORMATION: A synthetic peptide

<400> SEQUENCE: 68

Leu Gly Gly Trp Ser Trp His Ala Gly
 1               5

<210> SEQ ID NO 69
<211> LENGTH: 9
<212> TYPE: PRT
<213> ORGANISM: Artificial Sequence
<220> FEATURE:
<223> OTHER INFORMATION: A synthetic peptide

<400> SEQUENCE: 69

Thr Ala Gly Trp Trp Trp Gly Pro Trp
 1               5

<210> SEQ ID NO 70
<211> LENGTH: 9
<212> TYPE: PRT
<213> ORGANISM: Artificial Sequence
<220> FEATURE:
<223> OTHER INFORMATION: A synthetic peptide

<400> SEQUENCE: 70

Phe Cys Gly Trp Leu Trp Pro Trp Trp
 1               5

<210> SEQ ID NO 71
<211> LENGTH: 9
<212> TYPE: PRT
<213> ORGANISM: Artificial Sequence
<220> FEATURE:
<223> OTHER INFORMATION: A synthetic peptide

<400> SEQUENCE: 71

Ala Val Gly Trp Gly Trp Trp Trp Gly
 1               5

<210> SEQ ID NO 72
<211> LENGTH: 9
<212> TYPE: PRT
```

```
<213> ORGANISM: Artificial Sequence
<220> FEATURE:
<223> OTHER INFORMATION: A synthetic peptide
<220> FEATURE:
<221> NAME/KEY: SITE
<222> LOCATION: 1, 2, 5, 7, 8, 9
<223> OTHER INFORMATION: Xaa is any amino acid
<220> FEATURE:
<221> NAME/KEY: SITE
<222> LOCATION: 6
<223> OTHER INFORMATION: Xaa is an aromatic amino acid

<400> SEQUENCE: 72

Xaa Xaa Gly Trp Xaa Xaa Xaa Xaa Xaa
 1               5

<210> SEQ ID NO 73
<211> LENGTH: 22
<212> TYPE: PRT
<213> ORGANISM: Artificial Sequence
<220> FEATURE:
<223> OTHER INFORMATION: A synthetic peptide

<400> SEQUENCE: 73

Ser Leu Gly Leu Trp His Ser Gln Arg His Phe Asp Val His Arg Glu
 1               5                  10                  15

His Ser Arg His Gln Thr
             20

<210> SEQ ID NO 74
<211> LENGTH: 22
<212> TYPE: PRT
<213> ORGANISM: Artificial Sequence
<220> FEATURE:
<223> OTHER INFORMATION: A synthetic peptide

<400> SEQUENCE: 74

Glu Phe Ala Ala Ala Ile Asp Arg Val Arg Leu Phe Val Asp Lys Leu
 1               5                  10                  15

Asp Asn Ile Ala Gln Val
             20

<210> SEQ ID NO 75
<211> LENGTH: 22
<212> TYPE: PRT
<213> ORGANISM: Artificial Sequence
<220> FEATURE:
<223> OTHER INFORMATION: A synthetic peptide

<400> SEQUENCE: 75

Phe His Ile Gly Lys Leu Val Ser Gly Val Ala Glu Leu Leu Leu Asp
 1               5                  10                  15

Ser Gly Ala Arg Trp His
             20

<210> SEQ ID NO 76
<211> LENGTH: 22
<212> TYPE: PRT
<213> ORGANISM: Artificial Sequence
<220> FEATURE:
<223> OTHER INFORMATION: A synthetic peptide

<400> SEQUENCE: 76

Gln Arg Leu Pro Trp Gly Glu Trp Leu Gly Lys Val Leu Ser Leu Ser
 1               5                  10                  15

Glu Ser Pro Trp His His
             20
```

```
<210> SEQ ID NO 77
<211> LENGTH: 22
<212> TYPE: PRT
<213> ORGANISM: Artificial Sequence
<220> FEATURE:
<223> OTHER INFORMATION: A synthetic peptide

<400> SEQUENCE: 77

Asp Ser Arg Val Gln Gly Leu Gly Leu Ala Ser Phe Trp Thr Asp Gly
 1               5                  10                  15

Val Phe Val Gly Thr Ala
            20

<210> SEQ ID NO 78
<211> LENGTH: 22
<212> TYPE: PRT
<213> ORGANISM: Artificial Sequence
<220> FEATURE:
<223> OTHER INFORMATION: A synthetic peptide

<400> SEQUENCE: 78

Pro Ala Ser Leu Ser Ser Pro Ala Ile Thr Pro Leu Lys Ser Ser Trp
 1               5                  10                  15

Trp Ser Thr Ile Gly Ala
            20

<210> SEQ ID NO 79
<211> LENGTH: 22
<212> TYPE: PRT
<213> ORGANISM: Artificial Sequence
<220> FEATURE:
<223> OTHER INFORMATION: A synthetic peptide

<400> SEQUENCE: 79

Thr Ala Gly Val Ser Tyr Phe Arg Glu Pro Val Met Leu Thr Thr Trp
 1               5                  10                  15

Val Leu Arg Ala Trp Ala
            20

<210> SEQ ID NO 80
<211> LENGTH: 22
<212> TYPE: PRT
<213> ORGANISM: Artificial Sequence
<220> FEATURE:
<223> OTHER INFORMATION: A synthetic peptide

<400> SEQUENCE: 80

Thr Thr Gly Gly Leu Gly Gly Pro Ile Gly His Ser Leu His Gln His
 1               5                  10                  15

Gly Leu Lys Phe Arg Ala
            20

<210> SEQ ID NO 81
<211> LENGTH: 22
<212> TYPE: PRT
<213> ORGANISM: Artificial Sequence
<220> FEATURE:
<223> OTHER INFORMATION: A synthetic peptide

<400> SEQUENCE: 81

Met Arg His Gln Arg Val Thr Phe Pro Ala His Ile Cys Tyr Ile Cys
 1               5                  10                  15
```

```
Ala Phe Trp Gln Pro Ala
            20

<210> SEQ ID NO 82
<211> LENGTH: 22
<212> TYPE: PRT
<213> ORGANISM: Artificial Sequence
<220> FEATURE:
<223> OTHER INFORMATION: A synthetic peptide

<400> SEQUENCE: 82

Ile Thr Phe Phe Pro Tyr Lys Leu Leu His Gly Leu Thr Asn Tyr Val
1               5                   10                  15

Ile Gly Leu Gln Arg Asn
            20

<210> SEQ ID NO 83
<211> LENGTH: 22
<212> TYPE: PRT
<213> ORGANISM: Artificial Sequence
<220> FEATURE:
<223> OTHER INFORMATION: A synthetic peptide

<400> SEQUENCE: 83

His Leu Val Arg Val Gly Met Glu Asn Leu His Ala Ala Ser Asn Phe
1               5                   10                  15

Leu Phe Gly Ser Leu Phe
            20

<210> SEQ ID NO 84
<211> LENGTH: 22
<212> TYPE: PRT
<213> ORGANISM: Artificial Sequence
<220> FEATURE:
<223> OTHER INFORMATION: A synthetic peptide

<400> SEQUENCE: 84

His Val Ala Ser His Pro Phe Gly Ala Leu Ser Arg Val Met Leu Phe
1               5                   10                  15

Leu Leu Asp Lys Leu Asn
            20

<210> SEQ ID NO 85
<211> LENGTH: 22
<212> TYPE: PRT
<213> ORGANISM: Artificial Sequence
<220> FEATURE:
<223> OTHER INFORMATION: A synthetic peptide

<400> SEQUENCE: 85

Asn Glu Ala Tyr Asn Glu Lys Ala Asn Glu Thr Pro Thr Leu Asn Gly
1               5                   10                  15

Lys Val Asp Lys Cys Pro
            20

<210> SEQ ID NO 86
<211> LENGTH: 22
<212> TYPE: PRT
<213> ORGANISM: Artificial Sequence
<220> FEATURE:
<223> OTHER INFORMATION: A synthetic peptide

<400> SEQUENCE: 86

Ile Pro Leu Gly Leu Ala Phe Ala Ala Met Pro Gly Thr Leu Ala Asp
1               5                   10                  15
```

```
Gln Ile Leu Arg His His
            20

<210> SEQ ID NO 87
<211> LENGTH: 22
<212> TYPE: PRT
<213> ORGANISM: Artificial Sequence
<220> FEATURE:
<223> OTHER INFORMATION: A synthetic peptide

<400> SEQUENCE: 87

Leu Asp Tyr Met Leu Glu Ala Leu Leu His Tyr Thr Phe Pro Arg Ala
 1               5                  10                  15

Thr Gln His Pro His Ile
            20

<210> SEQ ID NO 88
<211> LENGTH: 22
<212> TYPE: PRT
<213> ORGANISM: Artificial Sequence
<220> FEATURE:
<223> OTHER INFORMATION: A synthetic peptide

<400> SEQUENCE: 88

Arg Pro Leu Met Phe Thr Pro Pro Ser Ala Ile Ser Arg Leu Met His
 1               5                  10                  15

His Gly Asn His Met Ser
            20

<210> SEQ ID NO 89
<211> LENGTH: 22
<212> TYPE: PRT
<213> ORGANISM: Artificial Sequence
<220> FEATURE:
<223> OTHER INFORMATION: A synthetic peptide

<400> SEQUENCE: 89

Lys Val Phe Pro Phe Val Asn His Val Val Asp Thr Ala Gly Trp Phe
 1               5                  10                  15

Ile Thr Leu Phe Lys Tyr
            20

<210> SEQ ID NO 90
<211> LENGTH: 22
<212> TYPE: PRT
<213> ORGANISM: Artificial Sequence
<220> FEATURE:
<223> OTHER INFORMATION: A synthetic peptide

<400> SEQUENCE: 90

Thr Asn Gly Leu Ala Gln Leu Leu Asn Leu Ser Phe Leu Thr Asn Phe
 1               5                  10                  15

Ile Thr Leu Leu Arg Ser
            20

<210> SEQ ID NO 91
<211> LENGTH: 22
<212> TYPE: PRT
<213> ORGANISM: Artificial Sequence
<220> FEATURE:
<223> OTHER INFORMATION: A synthetic peptide

<400> SEQUENCE: 91

Arg Asp Leu Cys Ser Ser Ile Ser His Ser Asp Arg Val Lys Gly Cys
```

```
                1               5                   10                  15
Ile Arg Pro Leu Ser Pro
            20

<210> SEQ ID NO 92
<211> LENGTH: 22
<212> TYPE: PRT
<213> ORGANISM: Artificial Sequence
<220> FEATURE:
<223> OTHER INFORMATION: A synthetic peptide

<400> SEQUENCE: 92

Tyr Gln Trp Leu Ile Leu Ser Met Lys Ser Ile Ala Pro Asn Ile Ala
1               5                   10                  15

Pro Ser Lys Gln His Ser
            20

<210> SEQ ID NO 93
<211> LENGTH: 22
<212> TYPE: PRT
<213> ORGANISM: Artificial Sequence
<220> FEATURE:
<223> OTHER INFORMATION: A synthetic peptide

<400> SEQUENCE: 93

Asp Val Asn Asp Glu Phe Val Trp Arg Phe Arg Ser Tyr Ile His Pro
1               5                   10                  15

Ile Val Ala Asn Phe Leu
            20

<210> SEQ ID NO 94
<211> LENGTH: 22
<212> TYPE: PRT
<213> ORGANISM: Artificial Sequence
<220> FEATURE:
<223> OTHER INFORMATION: A synthetic peptide

<400> SEQUENCE: 94

Ile Leu Pro Gly Phe His Gly Leu Ile Gln Asn Leu Thr His Tyr Leu
1               5                   10                  15

Trp Lys Thr Ile Gly Phe
            20

<210> SEQ ID NO 95
<211> LENGTH: 13
<212> TYPE: PRT
<213> ORGANISM: Artificial Sequence
<220> FEATURE:
<223> OTHER INFORMATION: A synthetic peptide

<400> SEQUENCE: 95

Ile Pro His Arg His Gln Phe His His Thr Ala His Ala
1               5                   10

<210> SEQ ID NO 96
<211> LENGTH: 13
<212> TYPE: PRT
<213> ORGANISM: Artificial Sequence
<220> FEATURE:
<223> OTHER INFORMATION: A synthetic peptide

<400> SEQUENCE: 96

Ile Gly Gly Trp Ser His His His Leu Gly Arg Thr Ala
1               5                   10
```

```
<210> SEQ ID NO 97
<211> LENGTH: 13
<212> TYPE: PRT
<213> ORGANISM: Artificial Sequence
<220> FEATURE:
<223> OTHER INFORMATION: A synthetic peptide

<400> SEQUENCE: 97

Glu Trp His Arg His His Arg His Pro Glu Val Leu Ala
 1               5                  10

<210> SEQ ID NO 98
<211> LENGTH: 13
<212> TYPE: PRT
<213> ORGANISM: Artificial Sequence
<220> FEATURE:
<223> OTHER INFORMATION: A synthetic peptide

<400> SEQUENCE: 98

Pro His Pro Phe Arg His His His Gly Leu Arg Ala Pro
 1               5                  10

<210> SEQ ID NO 99
<211> LENGTH: 13
<212> TYPE: PRT
<213> ORGANISM: Artificial Sequence
<220> FEATURE:
<223> OTHER INFORMATION: A synthetic peptide

<400> SEQUENCE: 99

His Ala Ala Gly His His His His Gly Trp Trp Arg Pro
 1               5                  10

<210> SEQ ID NO 100
<211> LENGTH: 13
<212> TYPE: PRT
<213> ORGANISM: Artificial Sequence
<220> FEATURE:
<223> OTHER INFORMATION: A synthetic peptide

<400> SEQUENCE: 100

Trp Gly Gly Gly Lys His His His His Arg Gly Pro Gly
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: A synthetic peptide

<400> SEQUENCE: 101

Ile Arg His Ile His Gly His Asp Lys Leu Thr His Ala
 1               5                  10

<210> SEQ ID NO 102
<211> LENGTH: 13
<212> TYPE: PRT
<213> ORGANISM: Artificial Sequence
<220> FEATURE:
<223> OTHER INFORMATION: A synthetic peptide

<400> SEQUENCE: 102

His Gly His Trp Arg His Thr His Thr Gly Asp Arg Gly
 1               5                  10
```

```
<210> SEQ ID NO 103
<211> LENGTH: 13
<212> TYPE: PRT
<213> ORGANISM: Artificial Sequence
<220> FEATURE:
<223> OTHER INFORMATION: A synthetic peptide

<400> SEQUENCE: 103

Tyr Ser His His His His His His Leu Ala Gly Thr Ala
1               5                   10

<210> SEQ ID NO 104
<211> LENGTH: 13
<212> TYPE: PRT
<213> ORGANISM: Artificial Sequence
<220> FEATURE:
<223> OTHER INFORMATION: A synthetic peptide

<400> SEQUENCE: 104

His Tyr His Tyr Met His Arg His Ser Gly Ser Ser Pro
1               5                   10

<210> SEQ ID NO 105
<211> LENGTH: 13
<212> TYPE: PRT
<213> ORGANISM: Artificial Sequence
<220> FEATURE:
<223> OTHER INFORMATION: A synthetic peptide

<400> SEQUENCE: 105

Pro His His Val His Thr His Gly Ala Arg Gly Gly Gly
1               5                   10

<210> SEQ ID NO 106
<211> LENGTH: 13
<212> TYPE: PRT
<213> ORGANISM: Artificial Sequence
<220> FEATURE:
<223> OTHER INFORMATION: A synthetic peptide

<400> SEQUENCE: 106

His Asn His Gly Leu His Leu His Gly Gly Glu Arg Gly
1               5                   10

<210> SEQ ID NO 107
<211> LENGTH: 13
<212> TYPE: PRT
<213> ORGANISM: Artificial Sequence
<220> FEATURE:
<223> OTHER INFORMATION: A synthetic peptide

<400> SEQUENCE: 107

Ile Gly His Leu Met His Gly His Arg Ser Ser Val Thr
1               5                   10

<210> SEQ ID NO 108
<211> LENGTH: 13
<212> TYPE: PRT
<213> ORGANISM: Artificial Sequence
<220> FEATURE:
<223> OTHER INFORMATION: A synthetic peptide

<400> SEQUENCE: 108

Leu Ala Tyr Arg Trp His His His His Trp Gly Pro Ala
1               5                   10

<210> SEQ ID NO 109
```

-continued

```
<211> LENGTH: 13
<212> TYPE: PRT
<213> ORGANISM: Artificial Sequence
<220> FEATURE:
<223> OTHER INFORMATION: A synthetic peptide

<400> SEQUENCE: 109

Leu Ala Ile Val Arg His Ser His Ser Leu Gly Ile Gly
 1               5                  10

<210> SEQ ID NO 110
<211> LENGTH: 13
<212> TYPE: PRT
<213> ORGANISM: Artificial Sequence
<220> FEATURE:
<223> OTHER INFORMATION: A synthetic peptide

<400> SEQUENCE: 110

Thr Val Val His Lys His Gly His His Val Arg Gly Gly
 1               5                  10

<210> SEQ ID NO 111
<211> LENGTH: 13
<212> TYPE: PRT
<213> ORGANISM: Artificial Sequence
<220> FEATURE:
<223> OTHER INFORMATION: A synthetic peptide

<400> SEQUENCE: 111

Arg His His His His Asp Pro Arg Gly Gly Gly Trp Pro
 1               5                  10

<210> SEQ ID NO 112
<211> LENGTH: 5
<212> TYPE: PRT
<213> ORGANISM: Artificial Sequence
<220> FEATURE:
<223> OTHER INFORMATION: A synthetic peptide

<400> SEQUENCE: 112

Gly Gly Ser Gly Gly
 1               5

<210> SEQ ID NO 113
<211> LENGTH: 21
<212> TYPE: PRT
<213> ORGANISM: Artificial Sequence
<220> FEATURE:
<223> OTHER INFORMATION: A synthetic peptide

<400> SEQUENCE: 113

Glu His Gly Gln Leu Phe Val Ser His Val Ser Ser Ser Arg Gly His
 1               5                  10                  15

Val His Ala Pro Met
            20

<210> SEQ ID NO 114
<211> LENGTH: 21
<212> TYPE: PRT
<213> ORGANISM: Artificial Sequence
<220> FEATURE:
<223> OTHER INFORMATION: A synthetic peptide

<400> SEQUENCE: 114

Tyr His Tyr His Pro Gly Gly Val Trp Pro Met Arg Arg Pro Ala Pro
 1               5                  10                  15
```

Pro Leu Thr Thr Gly
            20

<210> SEQ ID NO 115
<211> LENGTH: 21
<212> TYPE: PRT
<213> ORGANISM: Artificial Sequence
<220> FEATURE:
<223> OTHER INFORMATION: A synthetic peptide

<400> SEQUENCE: 115

Thr His Ser Val Gln Tyr Phe Arg Leu Cys Gln Leu Gln His Thr Lys
1               5                   10                  15

Val Arg His Tyr Trp
            20

<210> SEQ ID NO 116
<211> LENGTH: 11
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 2
<223> OTHER INFORMATION: Xaa is Arg, Val, Phe, Asn, Tyr, Lys, Ala, Gly,
      Thr, or Ile
<220> FEATURE:
<221> NAME/KEY: SITE
<222> LOCATION: 4, 7, 8, 9
<223> OTHER INFORMATION: Xaa can be absent or any amino acid
<220> FEATURE:
<221> NAME/KEY: SITE
<222> LOCATION: 5, 10
<223> OTHER INFORMATION: Xaa can be any amino acid

<400> SEQUENCE: 116

His Xaa His Xaa Xaa His Xaa Xaa Xaa Xaa His
1               5                   10

<210> SEQ ID NO 117
<211> LENGTH: 7
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 2, 4, 6
<223> OTHER INFORMATION: Xaa can be Arg, Val, Phe, Ala, Gly, Thr, or Ile

<400> SEQUENCE: 117

His Xaa His Xaa His Xaa His
1               5

<210> SEQ ID NO 118
<211> LENGTH: 8
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1, 2
<223> OTHER INFORMATION: Xaa can be absent or any amino acid
<220> FEATURE:
<221> NAME/KEY: SITE
<222> LOCATION: 3, 4, 5
<223> OTHER INFORMATION: Xaa can be any amino acid

<400> SEQUENCE: 118

```
Xaa Xaa Xaa Xaa Xaa His His His
 1               5

<210> SEQ ID NO 119
<211> LENGTH: 9
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1, 5, 9
<223> OTHER INFORMATION: Xaa can be any amino acid
<220> FEATURE:
<221> NAME/KEY: SITE
<222> LOCATION: 8
<223> OTHER INFORMATION: Xaa can be Gly or Trp

<400> SEQUENCE: 119

Xaa Ala Gly Trp Xaa Trp Trp Xaa Xaa
 1               5

<210> SEQ ID NO 120
<211> LENGTH: 9
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1, 2, 5, 7, 8, 9
<223> OTHER INFORMATION: Xaa can be any amino acid
<220> FEATURE:
<221> NAME/KEY: SITE
<222> LOCATION: 6
<223> OTHER INFORMATION: Xaa can be an aromatic amino acid

<400> SEQUENCE: 120

Xaa Xaa Gly Trp Xaa Xaa Xaa Xaa Xaa
 1               5

<210> SEQ ID NO 121
<211> LENGTH: 4
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Xaa can be Gly, Pro or Leu
<220> FEATURE:
<221> NAME/KEY: SITE
<222> LOCATION: 3
<223> OTHER INFORMATION: Xaa can be any amino acid
<220> FEATURE:
<221> NAME/KEY: SITE
<222> LOCATION: 4
<223> OTHER INFORMATION: Xaa can be an aromatic amino acid

<400> SEQUENCE: 121

Xaa Trp Xaa Xaa
 1

<210> SEQ ID NO 122
<211> LENGTH: 5
<212> TYPE: PRT
<213> ORGANISM: Artificial Sequence
<220> FEATURE:
<223> OTHER INFORMATION: A synthetic peptide
<220> FEATURE:
```

```
<221> NAME/KEY: SITE
<222> LOCATION: (2)...(4)
<223> OTHER INFORMATION: Xaa can be any amino acid

<400> SEQUENCE: 122

Leu Xaa Xaa Xaa Leu
 1               5

<210> SEQ ID NO 123
<211> LENGTH: 22
<212> TYPE: PRT
<213> ORGANISM: Artificial Sequence
<220> FEATURE:
<223> OTHER INFORMATION: A synthetic peptide

<400> SEQUENCE: 123

Ser Leu Gly Leu Trp His Ser Gln Arg His Phe Asp Val His Arg Glu
 1               5                  10                  15

His Ser Arg His Gln Thr
            20

<210> SEQ ID NO 124
<211> LENGTH: 100
<212> TYPE: DNA
<213> ORGANISM: Artificial Sequence
<220> FEATURE:
<223> OTHER INFORMATION: A synthetic oligonucleotide

<400> SEQUENCE: 124
atcggatctg gttccgcgtg gatcccgggc ccagccggcc ctgcagggat ccccggaatt      60
cccgggtcga ctcgagcggc cgcatcgtga ctgactgacg                          100

<210> SEQ ID NO 125
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 125
atcggatctg gttccgcgtg gatcccgggc ccagccggcc attggtggtt ggtctcatca      60
tcatcttggt aggacggctg cggccgcatc gtgactgact gacg                    104

<210> SEQ ID NO 126
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 126
atcggatctg gttccgcgtg gatcccgggc ccagccggcc cattatcatt atatgcatcg      60
tcattcgggt tctagtccgg cggccgcatc gtgactgact gacg                    104

<210> SEQ ID NO 127
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 127
atcggatctg gttccgcgtg gatcccgggc ccagccggcc attgggcatc tgatgcatgg      60
```
tcatcgtagt tctgttacgg cggccgcatc gtgactgact gacg    104

<210> SEQ ID NO 128
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 128
atcggatctg gttccgcgtg gatcccgggc ccagccggcc tatacgagga cgcctcatgt    60
gcattggcat gcgcatggtg cggccgcatc gtgactgact gacg    104

<210> SEQ ID NO 129
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 129
atcggatctg gttccgcgtg gatcccgggc ccagccggcc cctcatccgt ttaggcatca    60
tcatggtctg agggcgccgg cggccgcatc gtgactgact gacg    104

<210> SEQ ID NO 130
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 130
atcggatctg gttccgcgtg gatcccgggc ccagccggcc catgctgctg gtcatcatca    60
tcatgggtgg tggaggcctg cggccgcatc gtgactgact gacg    104

<210> SEQ ID NO 131
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 131
atcggatctg gttccgcgtg gatcccgggc ccagccggcc cttgcttata ggtggcatca    60
tcatcattgg gggccggctg cggccgcatc gtgactgact gacg    104

<210> SEQ ID NO 132
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 132
atcggatctg gttccgcgtg gatcccgggc ccagccggcc tggggtggtt ggcgtcatgt    60
tcatggtcat cgtcatcctg cggccgcatc gtgactgact gacg    104

<210> SEQ ID NO 133
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 133
atcggatctg gttccgcgtg gatcccgggc ccagccggcc catgggcatt ggaggcatac    60
gcatacgggg gatagggggg cggccgcatc gtgactgact gacg                    104

<210> SEQ ID NO 134
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 134
atcggatctg gttccgcgtg gatcccgggc ccagccggcc gagtggcata ggcatcatcg    60
gcatccggag gtgttggcgg cggccgcatc gtgactgact gacg                    104

<210> SEQ ID NO 135
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 135
atcggatctg gttccgcgtg gatcccgggc ccagccggcc tgggggggg ggaagcatca    60 tcatcatcgg gggccggggg cggccgcatc gtgactgact gacg                    104

<210> SEQ ID NO 136
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 136
atcggatctg gttccgcgtg gatcccgggc ccagccggcc cataatcatg ggcttcattt    60 gcatggggg gagcgggggg cggccgcatc gtgactgact gacg                     104

<210> SEQ ID NO 137
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 137
atcggatctg gttccgcgtg gatcccgggc ccagccggcc tattctcatc atcatcatca    60
tcatttggct ggtacggcgg cggccgcatc gtgactgact gacg                    104

<210> SEQ ID NO 138
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 138
atcggatctg gttccgcgtg gatcccgggc ccagccggcc attaggcata ttcatggtca    60
tgataagctg acgcatgctg cggccgcatc gtgactgact gacg                    104

<210> SEQ ID NO 139

<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 139
atcggatctg gttccgcgtg gatcccgggc ccagccggcc attcctcatc gtcatcagtt    60
tcatcatacg gctcatgcgg cggccgcatc gtgactgact gacg                     104

<210> SEQ ID NO 140
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 140
atcggatctg gttccgcgtg gatcccgggc ccagccggcc cctcatcatg tgcatacgca    60
tggtgcgcgt gggggggggg cggccgcatc gtgactgact gacg                     104

<210> SEQ ID NO 141
<211> LENGTH: 104
<212> TYPE: DNA
<213> ORGANISM: Artificial Sequence
<220> FEATURE:
<223> OTHER INFORMATION: A synthetic oligonucleotide

<400> SEQUENCE: 141
atcggatctg gttccgcgtg gatcccgggc ccagccggcc cttgctattg ttcgtcattc    60
gcattctctt ggtattgggg cggccgcatc gtgactgact gacg                     104

<210> SEQ ID NO 142
<211> LENGTH: 8
<212> TYPE: PRT
<213> ORGANISM: Artificial Sequence
<220> FEATURE:
<223> OTHER INFORMATION: A synthetic peptide

<400> SEQUENCE: 142

His Val His Trp His Ala His Gly
  1               5

<210> SEQ ID NO 143
<211> LENGTH: 825
<212> TYPE: DNA
<213> ORGANISM: Artificial Sequence
<220> FEATURE:
<223> OTHER INFORMATION: A synthetic oligonucleotide

<400> SEQUENCE: 143
atggggtccc tgcaggactc agaagtcaat caagaagcta agccagaggt caagccagaa    60
gtcaagcctg agactcacat caatttaaag gtgtccgatg gatcttcaga gatcttcttc    120
aagatcaaaa agaccactcc tttaagaagg ctgatggaag cgttcgctaa aagacagggt    180
aaggaaatgg actccttaag attcttgtac gacggtatta gaattcaagc tgatcaggcc    240
cctgaagatt tggacatgga ggataacgat attattgagg ctcaccgcga acagattgga    300
ggtggagacc gcgagaacct gtactttcag ggcggtctga actcaggcct cacgacaaat    360
cctggtgtat ccgcttggca ggtcaacaca gcttatactg cgggacaatt ggtcacatat    420
aacggcaaga cgtataaatg tttgcagccc cacacctcct ggcaggatgg gaaccatcc    480

| | | |
|---|---|---|
| aacgttcctg ccttgtggca gcttcaaggt ggctctggtg gcctggaagt tctgttccag | 540 |
| gggcccggcc cagccggccg ttatacgcgt acacctcatg tgcactggca tgcgcacggc | 600 |
| ggttcttggg gcggatggcg acacgtacac ggtcatcgtc atcccggagg atcatacacc | 660 |
| cggactccgc acgtacattg gcacgcacat ggaggctcgt ggggtgggtg cgccatgtc | 720 |
| catggccacc gacaccctgg gggttcctac acacgcacgc cacatgtcca ttggcacgct | 780 |
| cacgggggcg gccgcgacta caaggatgac gatgacaagt aatag | 825 |

<210> SEQ ID NO 144
<211> LENGTH: 273
<212> TYPE: PRT
<213> ORGANISM: Artificial Sequence
<220> FEATURE:
<223> OTHER INFORMATION: A synthetic peptide

<400> SEQUENCE: 144

Met Gly Ser Leu Gln Asp Ser Glu Val Asn Gln Glu Ala Lys Pro Glu
1               5                   10                  15

Val Lys Pro Glu Val Lys Pro Glu Thr His Ile Asn Leu Lys Val Ser
            20                  25                  30

Asp Gly Ser Ser Glu Ile Phe Phe Lys Ile Lys Lys Thr Thr Pro Leu
        35                  40                  45

Arg Arg Leu Met Glu Ala Phe Ala Lys Arg Gln Gly Lys Glu Met Asp
    50                  55                  60

Ser Leu Arg Phe Leu Tyr Asp Gly Ile Arg Ile Gln Ala Asp Gln Ala
65                  70                  75                  80

Pro Glu Asp Leu Asp Met Glu Asp Asn Asp Ile Ile Glu Ala His Arg
                85                  90                  95

Glu Gln Ile Gly Gly Gly Asp Arg Glu Asn Leu Tyr Phe Gln Gly Gly
            100                 105                 110

Leu Asn Ser Gly Leu Thr Thr Asn Pro Gly Val Ser Ala Trp Gln Val
        115                 120                 125

Asn Thr Ala Tyr Thr Ala Gly Gln Leu Val Thr Tyr Asn Gly Lys Thr
    130                 135                 140

Tyr Lys Cys Leu Gln Pro His Thr Ser Leu Ala Gly Trp Glu Pro Ser
145                 150                 155                 160

Asn Val Pro Ala Leu Trp Gln Leu Gln Gly Gly Ser Gly Gly Leu Glu
                165                 170                 175

Val Leu Phe Gln Gly Pro Gly Pro Ala Gly Arg Tyr Thr Arg Thr Pro
            180                 185                 190

His Val His Trp His Ala His Gly Gly Ser Trp Gly Gly Trp Arg His
        195                 200                 205

Val His Gly His Arg His Pro Gly Gly Ser Tyr Thr Arg Thr Pro His
    210                 215                 220

Val His Trp His Ala His Gly Gly Ser Trp Gly Gly Trp Arg His Val
225                 230                 235                 240

His Gly His Arg His Pro Gly Gly Ser Tyr Thr Arg Thr Pro His Val
                245                 250                 255

His Trp His Ala His Gly Gly Gly Arg Asp Tyr Lys Asp Asp Asp Asp
            260                 265                 270

Lys

<210> SEQ ID NO 145
<211> LENGTH: 684
<212> TYPE: DNA

<213> ORGANISM: Artificial Sequence
<220> FEATURE:
<223> OTHER INFORMATION: A synthetic oligonucleotide

<400> SEQUENCE: 145

```
atgggtcatc accatcatca tcacgggtcc ctgcaggact cagaagtcaa tcaagaagct    60
aagccagagg tcaagccaga agtcaagcct gagactcaca tcaatttaaa ggtgtccgat   120
ggatcttcag agatcttctt caagatcaaa aagaccactc ctttaagaag gctgatggaa   180
gcgttcgcta aaagacaggg taaggaaatg gactccttaa gattcttgta cgacggtatt   240
agaattcaag ctgatcaggc ccctgaagat ttggacatgg aggataacga tattattgag   300
gctcaccgcg aacagattgg aggtggagac cgcgagaacc tgtactttca gggcggtctg   360
aactcaggcc tcacgacaaa tcctggtgta tccgcttggc aggtcaacac agcttatact   420
gcgggacaat tggtcacata taacggcaag acgtataaat gtttgcagcc ccacacctcc   480
ttggcaggat gggaaccatc caacgttcct gccttgtggc agcttcaagg tggctctggt   540
ggcctggaag ttctgttcca ggggcccggc ccagccggcc aacaggcggg ctggggttgg   600
tggtggggtg gtagcggcca ggcgggctgg ggttggtggt ggggtggcgg ccgcgactac   660
aaggatgacg atgacaagta atag                                          684
```

<210> SEQ ID NO 146
<211> LENGTH: 228
<212> TYPE: PRT
<213> ORGANISM: Artificial Sequence
<220> FEATURE:
<223> OTHER INFORMATION: A synthetic peptide

<400> SEQUENCE: 146

```
Ala Ser Met Gly His His His His His Gly Ser Leu Gln Asp Ser
 1               5                  10                  15

Glu Val Asn Gln Glu Ala Lys Pro Glu Val Lys Pro Glu Val Lys Pro
                20                  25                  30

Glu Thr His Ile Asn Leu Lys Val Ser Asp Gly Ser Ser Glu Ile Phe
            35                  40                  45

Phe Lys Ile Lys Lys Thr Thr Pro Leu Arg Arg Leu Met Glu Ala Phe
     50                  55                  60

Ala Lys Arg Gln Gly Lys Glu Met Asp Ser Leu Arg Phe Leu Tyr Asp
 65                  70                  75                  80

Gly Ile Arg Ile Gln Ala Asp Gln Ala Pro Glu Asp Leu Asp Met Glu
                 85                  90                  95

Asp Asn Asp Ile Ile Glu Ala His Arg Glu Gln Ile Gly Gly Gly Asp
            100                 105                 110

Arg Glu Asn Leu Tyr Phe Gln Gly Gly Leu Asn Ser Gly Leu Thr Thr
        115                 120                 125

Asn Pro Gly Val Ser Ala Trp Gln Val Asn Thr Ala Tyr Thr Ala Gly
    130                 135                 140

Gln Leu Val Thr Tyr Asn Gly Lys Thr Tyr Lys Cys Leu Gln Pro His
145                 150                 155                 160

Thr Ser Leu Ala Gly Trp Glu Pro Ser Asn Val Pro Ala Leu Trp Gln
                165                 170                 175

Leu Gln Gly Gly Ser Gly Gly Leu Glu Val Leu Phe Gln Gly Pro Gly
            180                 185                 190

Pro Ala Gly Gln Gln Ala Gly Trp Gly Trp Trp Trp Gly Gly Ser Gly
        195                 200                 205
```

Gln Ala Gly Trp Gly Trp Trp Trp Gly Gly Arg Asp Tyr Lys Asp
    210                 215                 220

Asp Asp Asp Lys
225

<210> SEQ ID NO 147
<211> LENGTH: 1296
<212> TYPE: DNA
<213> ORGANISM: Artificial Sequence
<220> FEATURE:
<223> OTHER INFORMATION: A synthetic oligonucleotide

<400> SEQUENCE: 147

```
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt tatcgctgat ttataacaaa     360
gatctgctgc cgaacccgcc aaaaacctgg gaagagatcc cggcgctgga taagaactg      420
aaagcgaaag gtaagagcgc gctgatgttc aacctgcaag aaccgtactt cacctggccg     480
ctgattgctg ctgacggggg ttatgcgttc aagtatgaaa cggcaagta cgacattaaa      540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc aaaagagttc     840
ctcgaaaact atctgctgac tgatgaaggt ctggaagcgg ttaataaaga caaaccgctg     900
ggtgccgtag cgctgaagtc ttacgaggaa gagttggtga agatccgcg tattgccgcc      960
actatggaaa acgcccagaa aggtgaaatc atgccgaaca tcccgcagat gtccgctttc    1020
tggtatgccg tgcgtactgc ggtgatcaac gccgccagcg gtcgtcagac tgtcgatgaa    1080
gccctgaaag acgcgcagac taattcgagc tcgaacaaca caacaataa caataacaac    1140
aacctcgggg atgacgatga caaggtaccg catatgccag ccggccaaca ggcgggctgg    1200
ggttggtggt ggggtggtag cggccaggcg ggctggggtt ggtggtgggg tggcggccgc    1260
gactacaagg atgacgatga caagtaatag aagctt                              1296
```

<210> SEQ ID NO 148
<211> LENGTH: 428
<212> TYPE: PRT
<213> ORGANISM: Artificial Sequence
<220> FEATURE:
<223> OTHER INFORMATION: A synthetic peptide

<400> SEQUENCE: 148

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

```
Pro Gln Val Ala Ala Thr Gly Asp Gly Pro Asp Ile Ile Phe Trp Ala
 50                  55                  60
His Asp Arg Phe Gly Gly Tyr Ala Gln Ser Gly Leu Leu Ala Glu Ile
 65                  70                  75                  80
Thr Pro Asp Lys Ala Phe Gln Asp Lys Leu Tyr Pro Phe Thr Trp Asp
                 85                  90                  95
Ala Val Arg Tyr Asn Gly Lys Leu Ile Ala Tyr Pro Ile Ala Val Glu
                100                 105                 110
Ala Leu Ser Leu Ile Tyr Asn Lys Asp Leu Leu Pro Asn Pro Pro Lys
            115                 120                 125
Thr Trp Glu Glu Ile Pro Ala Leu Asp Lys Glu Leu Lys Ala Lys Gly
130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
                180                 185                 190
Leu Thr Phe Leu Val Asp Leu Ile Lys Asn Lys His Met Asn Ala Asp
            195                 200                 205
Thr Asp Tyr Ser Ile Ala Glu Ala Ala Phe Asn Lys Gly Glu Thr Ala
210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
                260                 265                 270
Asn Lys Glu Leu Ala Lys Glu Phe Leu Glu Asn Tyr Leu Leu Thr Asp
            275                 280                 285
Glu Gly Leu Glu Ala Val Asn Lys Asp Lys Pro Leu Gly Ala Val Ala
290                 295                 300
Leu Lys Ser Tyr Glu Glu Glu Leu Val Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Asn
            355                 360                 365
Ser Ser Ser Asn Asn Asn Asn Asn Asn Asn Asn Asn Asn Leu Gly Asp
370                 375                 380
Asp Asp Asp Lys Val Pro His Met Pro Ala Gly Gln Gln Ala Gly Trp
385                 390                 395                 400
Gly Trp Trp Trp Gly Ser Gly Gln Ala Gly Trp Gly Trp Trp Trp
                405                 410                 415
Gly Gly Gly Arg Asp Tyr Lys Asp Asp Asp Lys
                420                 425

<210> SEQ ID NO 149
<211> LENGTH: 1509
<212> TYPE: DNA
<213> ORGANISM: Artificial Sequence
<220> FEATURE:
<223> OTHER INFORMATION: A synthetic oligonucleotide
```

<400> SEQUENCE: 149

```
atgaaaatcg aagaaggtaa actggtaatc tggattaacg gcgataaagg ctataacggt    60
ctcgctgaag tcggtaagaa attcgagaaa gataccggaa ttaaagtcac cgttgagcat   120
ccggataaac tggaagagaa attcccacag gttgcggcaa ctggcgatgg ccctgacatt   180
atcttctggg cacacgaccg ctttggtggc tacgctcaat ctggcctgtt ggctgaaatc   240
accccggaca aagcgttcca ggacaagctg tatccgttta cctgggatgc cgtacgttac   300
aacggcaagc tgattgctta cccgatcgct gttgaagcgt atcgctgat ttataacaaa    360
gatctgctgc cgaacccgcc aaaaacctgg gaagagatcc cggcgctgga taagaactg   420
aaagcgaaag gtaagagcgc gctgatgttc aacctgcaag aaccgtactt cacctggccg   480
ctgattgctg ctgacggggg ttatgcgttc aagtatgaaa acggcaagta cgacattaaa   540
gacgtgggcg tggataacgc tggcgcgaaa gcgggtctga ccttcctggt tgacctgatt   600
aaaaacaaac acatgaatgc agacaccgat tactccatcg cagaagctgc ctttaataaa   660
ggcgaaacag cgatgaccat caacggcccg tgggcatggt ccaacatcga caccagcaaa   720
gtgaattatg gtgtaacggt actgccgacc ttcaagggtc aaccatccaa accgttcgtt   780
ggcgtgctga gcgcaggtat taacgccgcc agtccgaaca aagagctggc aaaagagttc   840
ctcgaaaact atctgctgac tgatgaaggt ctggaagcgg ttaataaaga caaaccgctg   900
ggtgccgtag cgctgaagtc ttacgaggaa gagttggtga agatccgcg tattgccgcc   960
actatggaaa acgcccagaa aggtgaaatc atgccgaaca tcccgcagat gtccgctttc  1020
tggtatgccg tgcgtactgc ggtgatcaac gccgccagcg tcgtcagac tgtcgatgaa  1080
gccctgaaag acgcgcagac taattcgagc tcgaacaaca acaacaataa caataacaac  1140
aacctcgggg atgacgatga caaggtaccg catatgggcg gtctgaactc aggcctcacg  1200
acaaatcctg gtgtatccgc ttggcaggtc aacacagctt atactgcggg acaattggtc  1260
acatataacg gcaagacgta taatgtttg cagccccaca cctccttggc aggatgggaa  1320
ccatccaacg ttcctgcctt gtggcagctt caaggtggct ctggtggcct ggaagttctg  1380
ttccaggggc ccggcccagc cggccaacag gcgggctggg gttggtggtg ggtggtagc  1440
ggccaggcgg gctggggttg gtggtggggt ggcggccgcg actacaagga tgacgatgac  1500
aagtaatag                                                         1509
```

<210> SEQ ID NO 150
<211> LENGTH: 501
<212> TYPE: PRT
<213> ORGANISM: Artificial Sequence
<220> FEATURE:
<223> OTHER INFORMATION: A synthetic peptide

<400> SEQUENCE: 150

```
Met Lys Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
     50                  55                  60
```

```
His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Asp
370                 375                 380

Asp Asp Asp Lys Val Pro His Met Gly Gly Leu Asn Ser Gly Leu Thr
385                 390                 395                 400

Thr Asn Pro Gly Val Ser Ala Trp Gln Val Asn Thr Ala Tyr Thr Ala
                405                 410                 415

Gly Gln Leu Val Thr Tyr Asn Gly Lys Thr Tyr Lys Cys Leu Gln Pro
            420                 425                 430

His Thr Ser Leu Ala Gly Trp Glu Pro Ser Asn Val Pro Ala Leu Trp
            435                 440                 445
```

```
Gln Leu Gln Gly Gly Ser Gly Gly Leu Glu Val Leu Phe Gln Gly Pro
    450             455             460
Gly Pro Ala Gly Gln Gln Ala Gly Trp Gly Trp Trp Trp Gly Gly Ser
465             470             475             480
Gly Gln Ala Gly Trp Gly Trp Trp Trp Gly Gly Arg Asp Tyr Lys
                485             490             495
Asp Asp Asp Asp Lys
            500
```

What is claimed is:

1. An isolated non-naturally occurring fusion polypeptide or isolated non-naturally occurring fusion peptide comprising a carotenoid binding peptide comprising a sequence of the formula $X^1X^2GWX^3HyX^4X^5X^6$ (SEQ ID NO:120)

Wherein Hy is an aromatic amino acid; $X^1$ is alanine, valine, leucine, glutamine, tryptophan, tyrosine, serine, proline, threonine or isoleucine; $X^2$ is alanine, glycine, isoleucine or valine; $X^3$ is tryptophan, methionine, glycine, proline, leucine, or serine; $X^4$ is tryptophan, phenylalanine, methionine, glycine, threonine, or histidine; $X^5$ is glycine, tryptophan, serine, phenylalanine, leucine, glutamine, or alanine; and $X^6$ is threonine, glycine, tryptophan, alanine, methionine, asparagine, or valine.

2. The isolated polypeptide or peptide of claim 1 wherein $X^2$ is alanine.

3. The isolated polypeptide or peptide of claim 1 wherein Hy is tryptophan.

4. The isolated polypeptide or peptide of claim 1 wherein $X^4$ is a tryptophan.

5. An isolated non-naturally occurring fusion polypeptide or isolated non-naturally occurring fusion peptide comprising a carotenoid binding peptide comprising a sequence $X^1WX^2Hy$ (SEQ ID NO:121)

where Hy is an aromatic amino acid; $X^2$ is any amino acid; and $X^1$ is a single amino acid selected from glycine, proline or leucine.

6. The isolated polypeptide or peptide of claim 5 wherein $X^1$ is glycine.

* * * * *